US009562036B2

(12) United States Patent
Reich et al.

(10) Patent No.: US 9,562,036 B2
(45) Date of Patent: Feb. 7, 2017

(54) FLUOROMETHYL-SUBSTITUTED PYRROLE CARBOXAMIDES AS CAV2.2 CALCIUM CHANNEL BLOCKERS

(71) Applicant: GRÜNENTHAL GMBH, Aachen (DE)

(72) Inventors: Melanie Reich, Aachen (DE); Stefan Schunk, Aachen (DE); Florian Jakob, Aachen (DE); Henning Steinhagen, Schwalbach (DE); Nils Damann, Hürth (DE); Michael Haurand, Aachen (DE); Marc Rogers, Cambridgeshire (GB); Kathy MacKenzie, Hertfordshire (GB)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 15/185,124

(22) Filed: Jun. 17, 2016

(65) Prior Publication Data

US 2016/0289214 A1 Oct. 6, 2016

Related U.S. Application Data

(63) Continuation of application No. PCT/EP2014/003430, filed on Dec. 18, 2014.

(30) Foreign Application Priority Data

Dec. 19, 2013 (EP) .................................... 13005933

(51) Int. Cl.
| | | |
|---|---|---|
| *C07D 403/04* | (2006.01) | |
| *C07D 401/04* | (2006.01) | |
| *C07D 409/04* | (2006.01) | |
| *C07D 413/04* | (2006.01) | |
| *C07D 403/14* | (2006.01) | |
| *C07D 413/14* | (2006.01) | |

(52) U.S. Cl.
CPC ........... *C07D 403/04* (2013.01); *C07D 401/04* (2013.01); *C07D 403/14* (2013.01); *C07D 409/04* (2013.01); *C07D 413/04* (2013.01); *C07D 413/14* (2013.01)

(58) Field of Classification Search
CPC ... C07D 403/04; C07D 403/14; C07D 401/04; C07D 409/04; C07D 413/04; C07D 413/14
USPC ........................................................ 514/227.8
See application file for complete search history.

(56) References Cited

U.S. PATENT DOCUMENTS

| | | |
|---|---|---|
| 7,968,591 B2 | 6/2011 | Oberboersch et al. |
| 9,115,132 B2 | 8/2015 | Beswick et al. |
| 9,302,988 B2 | 4/2016 | Schunk et al. |
| 2009/0137573 A1 | 5/2009 | Oberboersch et al. |
| 2013/0029962 A1 | 1/2013 | Frank et al. |
| 2013/0210796 A1 | 8/2013 | Beswick et al. |
| 2014/0066426 A1* | 3/2014 | Schunk ................ C07D 403/12 514/210.18 |
| 2016/0015687 A1 | 1/2016 | Beswick et al. |

FOREIGN PATENT DOCUMENTS

| | | |
|---|---|---|
| WO | 2007141039 A1 | 12/2007 |
| WO | 2012004604 A1 | 1/2012 |
| WO | 2014032801 A1 | 3/2014 |
| WO | 2015090599 A1 | 6/2015 |
| WO | 2015090603 A1 | 6/2015 |

OTHER PUBLICATIONS

A.R. Disanto, "Bioavailability and Bioequivalency Testing", Chapter 77, Gennaro (Ed), Remington's Pharmaceutical Sciences, 17th Ed., 1985.
A.M. Knevel, "Separation", Chapter 78, Gennaro (Ed), Remington's Pharmaceutical Sciences, 17th Ed., 1985.
G.B. Phillips, "Sterilization", Chapter 79, Gennaro (Ed), Remington's Pharmaceutical Sciences, 17th Ed., 1985.
F.P. Siegel, "Tonicity, Osmoticity, Osmolality, and Osmolarity", Chapter 80, Gennaro (Ed), Remington's Pharmaceutical Sciences, 17th Ed., 1985.
R.L. Giles, et al., "Plastic Packaging Materials", Chapter 81, Gennaro (Ed), Remington's Pharmaceutical Sciences, 17th Ed., 1985.
C.J. Lintner, "Stability of Pharmaceutical Products", Chapter 82, Gennaro (Ed), Remington's Pharmaceutical Sciences, 17th Ed., 1985.
C.R. Erskine, "Quality Assurance and Control", Chapter 83, Gennaro (Ed), Remington's Pharmaceutical Sciences, 17th Ed., 1985.
J.G. Nairn, "Solutions, Emulsions, Suspensions and Extractives", Chapter 84, Gennaro (Ed), Remington's Pharmaceutical Sciences, 17th Ed., 1985.
K.E. Avis, "Parenteral Preparations", Chapter 85, Gennaro (Ed), Remington's Pharmaceutical Sciences, 17th Ed., 1985.
S.J. Turco, et al., "Intravenous Admixtures", Chapter 86, Gennaro (Ed), Remington's Pharmaceutical Sciences, 17th Ed., 1985.
J.D. Mullins, "Ophthalmic Preparations", Chapter 87, Gennaro (Ed), Remington's Pharmaceutical Sciences, 17th Ed., 1985.
L.H. Block, "Medicated Applications", Chapter 88, Gennaro (Ed), Remington's Pharmaceutical Sciences, 17th Ed., 1985.
E.G. Ripple, "Powders", Chapter 89, Gennaro (Ed), Remington's Pharmaceutical Sciences, 17th Ed., 1985.
R.E. King, et al., "Oral Solid Dosage Forms", Chapter 90, Gennaro (Ed), Remington's Pharmaceutical Sciences, 17th Ed., 1985.
S.C. Porter, "Coating of Pharmaceutical Dosage Forms", Chapter 91, Gennaro (Ed), Remington's Pharmaceutical Sciences, 17th Ed., 1985.

(Continued)

*Primary Examiner* — Yong Chu
(74) *Attorney, Agent, or Firm* — Norris McLaughlin & Marcus, P.A.

(57) ABSTRACT

The invention relates to pyrrole carboxamides bearing a fluoromethyl-moiety as voltage gated calcium channel blockers, to pharmaceutical compositions containing these compounds and also to these compounds for use in the treatment and/or prophylaxis of pain and further diseases and/or disorders.

15 Claims, No Drawings

(56) References Cited

OTHER PUBLICATIONS

M.A. Longer, et al., "Sustained-Release Drug Delivery Systems", Chapter 92, Gennaro (Ed), Remington's Pharmaceutical Sciences, 17th Ed., 1985.
J.J.Sclarro, et al., "Aerosols", Chapter 93, Gennaro (Ed), Remington's Pharmaceutical Sciences, 17th Ed., 1985.
L.J. Ravin, "Prefomulation", Chapter 76, Gennaro (Ed), Remington's Pharmaceutical Sciences, 17th Ed., 1985.
International Search Report and Written Opinion of the international Searching Authority for corresponding application PCT/EP2014/003429 dated Feb. 12, 2015.
G. J. Bennett, et al., "A peripheral mononeuropathy in rat that produces disorders of pain sensation like those seen in man", Elsevier Science Publishers B.V., Pain vol. 33, pp. 87-107, 1988.
F. E. D'Amour, et al., "A Method for Determining Loss of Pain Sensation", Biologic Research Laboratory, Denver, pp. 74-79, 1941.
D. Dubuisson, et al., "The Formalin Test: A Quantitative Study of the Analgesic Effects of Morphine, Meperidine, and Brain Stem Stimulation in Rats and Cats", Elsevier/North-Holland Biomedical Press, Pain vol. 4, pp. 161-174, 1977.
S. H. Kim, et al., "An Experimental model for peripheral neuropathy produced by the segmental spinal nerve ligation in the rat", Elsevier Science Publishers B.V., Pain vol. 50, pp. 355-363, 1992.
G.P. Miljanich, "Ziconotide: Neuronal Calcium Channel Blocker for Treating Severe Chronic Pain", Current Medicinal Chemistry, vol. 11, No. 23, pp. 3029-3040, 2004.
R. L. Rauck, MD., et al., "Intrathecal Ziconotide for Neuropathic Pain: A Review", World Institute of Pain, Pain Practice, vol. 9, Issue 5, pp. 327-337, 2009.
P. S. Staats, et al., "Intrathecal Ziconotide in the Treatment of Refractory Pain in Patients with Cancer or AIDS, A Randomized Controlled Trial", American Medical Association, JAMA vol. 291, No. 1, pp. 63-70, 2004.
S. Tyagarajan, et al., "A potent and selective indole N-type calcium channel (Cav2.2) blocker for the treatment of pain", Bioorganic & Medicinal Chemistry Letters, vol. 21, pp. 869-873, 2011.
International Search Report for corresponding application PCT/EP2014/003435 dated Feb. 12, 2015.

* cited by examiner

FLUOROMETHYL-SUBSTITUTED PYRROLE CARBOXAMIDES AS CAV2.2 CALCIUM CHANNEL BLOCKERS

PRIORITY

This application is a continuation of International Patent Application No. PCT/EP2014/003430, filed Dec. 18, 2014, which claims priority of European Patent Application 13005933.0, filed Dec. 19, 2013, the disclosures of which patent applications are incorporated herein by reference.

FIELD OF THE INVENTION

The invention relates to substituted pyrrole-2-yl-carboxamides bearing a fluorinated methyl moiety in 5-position as voltage gated Ca-channel (CaV) blockers, to pharmaceutical compositions containing these compounds and also to these compounds for use in the treatment and/or prophylaxis of pain and further diseases and/or disorders.

BACKGROUND OF THE INVENTION

Ion channels are proteins that form pores in membranes of biological cells and control the flow of ions down their electrochemical gradient. They are involved in the regulation of a wide range of cellular functions in both excitable and nonexcitable cells and provide attractive therapeutic targets for the treatment of various diseases.

In the somatosensory context, CaV2.2 channels, specific cellular plasma membrane calcium channels that belong to a diverse superfamily of voltage-gated calcium channels (VGCCs), were demonstrated to play an important role in spinal nociceptive processing.

The critical role of CaV2.2 in pain processing was underlined by the clinical efficacy of the intrathecally delivered, selective CaV2.2 channel antagonist Ziconotide (SNX-111; Prialt™), a synthetic peptide derived from a ω-(omega)-conotoxin peptide (Miljanich, 2004, Curr. Med. Chem., 11(23), p. 3029-40; Staats et al., 2004, JAMA, 291(1), p. 63-70). Inthrathecal administration of Ziconotide is required in order to reach the ion channel in presynaptic terminals of sensory neurons in the spinal cord. Common side effects of Ziconotide include memory impairment, dizziness, nystagmus, speech disorder, nervousness, somnolence and abnormal gait (Rauck et al., 2009, Pain Pract., 9, p. 327-37), which have been attributed to the inhibition of CaV2.2 channels in the brain by Ziconotide.

Therefore, a demand remains for the development of orally available CaV2.2 calcium channel blockers that show the desired qualities and effectively block CaV2.2 calcium channels in the nociceptive signaling pathway.

1,4-disubstituted pyrrol-2-yl carboxylic acid amides are known from WO2007/141039 A1.

SUMMARY OF THE INVENTION

The present invention describes small molecule CaV2.2 channel blockers.

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by CaV2.2 calcium channels.

This object is achieved by the subject matter described herein.

It has surprisingly been found that the compounds of general formula (I), as given below, display outstanding affinity to CaV2.2 calcium channels and are therefore particularly suitable for the prophylaxis and/or treatment of disorders or diseases which are at least partially mediated by CaV2.2 calcium channels.

The present invention therefore relates to a compound of general formula (I),

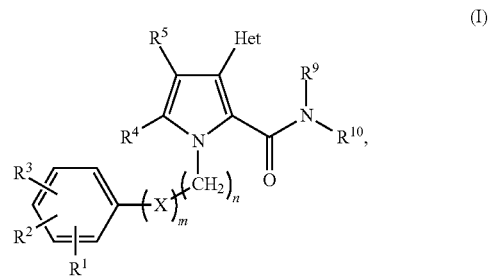

n represents 0, 1 or 2;
m represents 0 or 1 with the proviso that n≥m;
X is selected from the group consisting of O, S, NH and N—$C_{1-6}$-alkyl;
$R^1$, $R^2$ and $R^3$, are each independently of one another selected from the group consisting of H; F; Cl; Br; I; $NO_2$; CN; $C_{1-6}$-alkyl; $CF_3$; $CF_2H$; $CFH_2$; $CF_2Cl$; $CFCl_2$; C(=O)—H; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—$NH_2$; O—S(=O)$_2$—N(H)($C_{1-6}$-alkyl); O—S(=O)$_2$—N($C_{1-6}$-alkyl)$_2$; $NH_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—$NH_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—$NH_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—$NH_2$; N(H)—S(=O)$_2$—N(H)($C_{1-6}$-alkyl); N(H)—S(=O)$_2$N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—$NH_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$; $C_{3-6}$-cycloalkyl; 3 to 7 membered heterocyclyl; O—$C_{3-6}$-cycloalkyl or O-(3 to 7 membered heterocyclyl);
$R^4$ represents $CH_2F$; $CHF_2$, or $CF_3$;
$R^5$ represents H, $C_{1-6}$-alkyl, branched or unbranched, unsubstituted or mono- or poly-substituted, a $C_{3-6}$-cycloalkyl or a 3 to 7 membered heterocyclyl, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl); Het represents 5-, 6-, 8-, 9- or 10-membered heteroaryl, each substituted by zero or one or two or three substituents of the group consisting of $R^6$, $R^7$ and $R^8$, wherein $R^6$, $R^7$ and $R^8$, are each independently of one another selected from the group consisting of F; Cl; Br; I; $NO_2$; CN; $C_{1-6}$-alkyl; $CF_3$; $CF_2H$; $CFH_2$; $CF_2Cl$; $CFCl_2$; C(=O)—H; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—$NH_2$; O—S(=O)$_2$—N(H)($C_{1-6}$-alkyl); O—S(=O)$_2$—N($C_{1-6}$-alkyl)$_2$; $NH_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—$NH_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—$NH_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—$NH_2$; N(H)—S(=O)$_2$—N(H)($C_{1-6}$-alkyl); N(H)—S(=O)$_2$—N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—$NH_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); or S(=O)$_2$—N($C_{1-6}$-alkyl)$_2$; $C_{3-6}$-cycloalkyl; 3 to 7 membered heterocyclyl; O—$C_{3-6}$-cycloalkyl or O-(3 to 7 membered heterocyclyl);

$R^9$ represents H, $C_{1-10}$-alkyl, branched or unbranched, unsubstituted or mono- or poly-substituted; $C_{3-10}$-cycloalkyl or 3 to 10 membered heterocyclyl, in each case unsubstituted or mono- or poly-substituted and in each case optionally connected via a $C_{1-8}$-alkylene group, branched or unbranched, which in turn may be unsubstituted or mono- or polysubstituted;

$R^{10}$ represents H, $C_{1-10}$-alkyl; $C_{3-10}$-cycloalkyl, 3 to 10 membered heterocyclyl or heteroaryl, optionally connected via a $C_{1-8}$-alkylene group, branched or unbranched, which in turn may be unsubstituted or mono- or polysubstituted; or $R^9$ and $R^{10}$ together with the nitrogen atom connecting them form a 3 to 10 membered heterocyclyl;

wherein in each case said $C_{1-6}$-alkyl and $C_{1-10}$-alkyl may be branched or unbranched; unsubstituted or mono- or polysubstituted; and wherein in each case said $C_{3-6}$-cycloalkyl, 3 to 7 membered heterocyclyl, $C_{3-10}$-cycloalkyl, 3 to 10 membered heterocyclyl or heteroaryl may be unsubstituted or mono- or polysubstituted;

optionally in the form of a single stereoisomer or a mixture of stereoisomers, in the form of the free compound and/or a physiologically acceptable salt and/or a physiologically acceptable solvate thereof.

DETAILED DESCRIPTION

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio.

The term "physiologically acceptable salt" preferably comprises in the sense of this invention a salt of at least one compound according to the present invention and at least one physiologically acceptable acid or base.

A physiologically acceptable salt of at least one compound according to the present invention and at least one physiologically acceptable acid preferably refers in the sense of this invention to a salt of at least one compound according to the present invention with at least one inorganic or organic acid which is physiologically acceptable—in particular when used in human beings and/or other mammals.

A physiologically acceptable salt of at least one compound according to the present invention and at least one physiologically acceptable base preferably refers in the sense of this invention to a salt of at least one compound according to the present invention as an anion with at least one preferably inorganic cation, which is physiologically acceptable—in particular when used in human beings and/or other mammals.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents. Examples of physiologically acceptable solvents are water, alkanols, esters, ethers or ketones.

The terms "$C_{1-6}$-alkyl" and "$C_{1-10}$-alkyl" preferably comprise in the sense of this invention acyclic saturated aliphatic hydrocarbon residues, which can be respectively branched or unbranched and can be unsubstituted or can be mono- or polysubstituted, e.g. mono-, di- or trisubstituted, and which contain 1 to 6 carbon atoms, i.e. 1, 2, 3, 4, 5 or 6 carbon atoms, or 1 to 10, i.e. 1, 2, 3, 4, 5, 6, 7, 8, 9 or 10 carbon atoms, respectively, i.e. $C_{1-6}$ alkyl and $C_{1-10}$ alkyl. Preferred $C_{1-6}$-alkyl groups are selected from the group consisting of methyl, ethyl, n-propyl, 2-propyl, n-butyl, isobutyl, sec.-butyl, tert.-butyl, n-pentyl, isopentyl, neopentyl, and n-hexyl. Preferred $C_{1-10}$-alkyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl, n-decanyl and isooctyl.

In relation to the terms "$C_{1-4}$-alkyl" and "$C_{1-10}$-alkyl", the term "monosubstituted" or "polysubstituted" such as di- or tri-substituted refers in the sense of this invention, with respect to the corresponding groups, to the single substitution or multiple substitution, e.g. disubstitution or trisubstitution, of one or more hydrogen atoms each independently of one another by at least one substituent. The term "polysubstituted" such as di- or tri-substituted with respect to polysubstituted groups such as di- or tri-substituted groups includes the polysubstitution of these groups either on different or on the same atoms, for example trisubstituted on the same carbon atom, as in the case of $CF_3$ or $CH_2CF_3$ or at various points, as in the case of CH(OH)—$CH_2CH_2$—$CHCl_2$. The multiple substitution can be carried out using the same or using different substituents.

The term "$C_{3-6}$-cycloalkyl" and "$C_{3-10}$-cycloalkyl" mean for the purposes of this invention cyclic aliphatic hydrocarbons containing 3, 4, 5 or 6 carbon atoms and 3, 4, 5, 6, 7, 8, 9 or 10 carbon atoms, respectively, wherein the hydrocarbons in each case can be saturated or unsaturated (but not aromatic), unsubstituted or mono- or polysubstituted. The cycloalkyl group can be bound to the respective superordinate general structure via any desired and possible ring member of the cycloalkyl group. The cycloalkyl group can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or polysubstituted. $C_{3-10}$-cycloalkyls can furthermore be singly or multiply bridged such as, for example, in the case of adamantyl, bicycle-[2.2.1]heptyl or bicyclo[2.2.2]octyl. Preferred $C_{3-10}$-cycloalkyl groups are selected from the group consisting of cyclopropyl, cyclobutyl, cyclopentyl, cyclohexyl, cycloheptyl, cyclooctyl, cyclononyl, cyclodecyl, adamantly, cyclopentenyl, cyclohexenyl, cycloheptenyl, cyclooctenyl,

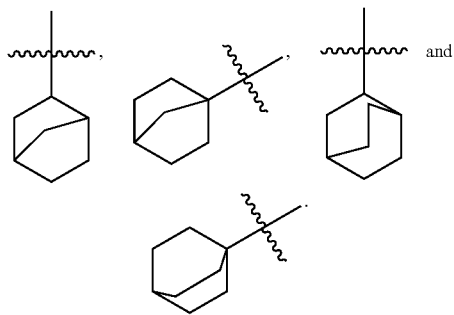

Preferred $C_{3-6}$-cycloalkyl groups are selected from the group consisting of cyclopropyl, cyclobutyl, cyclopentyl, cyclohexyl, cyclopentenyl and cyclohexenyl. Particularly preferred $C_{3-10}$-cycloalkyl groups and $C_{3-6}$-cycloalkyl groups are $C_{3-6}$-cycloalkyl groups such as cyclopropyl, cyclobutyl, cyclopentyl, cyclohexyl, cyclopentenyl and cyclohexenyl, in particular cyclopropyl.

The terms "3 to 7-membered heterocyclyl" and "3 to 10-membered heterocyclyl" mean for the purposes of this invention heterocycloaliphatic saturated or unsaturated (but not aromatic) residues having 3 to 7, i.e. 3, 4, 5, 6 or 7 ring members, and 3 to 10, i.e. 3, 4, 5, 6, 7, 8, 9 or 10 ring members, respectively, in which in each case at least one, if appropriate also two or three carbon atoms are replaced by a heteroatom or a heteroatom group each selected independently of one another from the group consisting of O, S, S(=O), S(=O)$_2$, N, NH and N($C_{1-6}$-alkyl) such as N(CH$_3$), wherein the ring members can be unsubstituted or mono- or polysubstituted. The cycloalkyl groups can also be condensed with further saturated or (partially) unsaturated cycloalkyl or heterocyclyl, aromatic or heteroaromatic ring systems, which in each case can in turn be unsubstituted or mono- or polysubstituted. The heterocyclyl group can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated or (partially) unsaturated cycloalkyl or heterocyclyl, aromatic or heteroaromatic ring systems, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5-, 6-, 8-, 9- or 10-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 10 ring members, wherein the ring system can be formed with further saturated or (partially) unsaturated cycloalkyl or heterocyclyl, aromatic or heteroaromatic ring systems, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

The term "$C_{1-8}$-alkylene" means in the sense of this invention a bivalent acyclic saturated, aliphatic hydrocarbon residue, which can be branched or unbranched and also unsubstituted or mono- or polysubstituted, which contain 1 to 8 carbon atoms respectively. Preferred $C_{1-8}$-alkylene groups are selected from the group consisting of CH$_2$, CH$_2$CH$_2$, CH(CH$_3$), CH$_2$CH$_2$CH$_2$, CH(CH$_3$)CH$_2$, CH(CH$_2$CH$_3$), CH$_2$(CH$_2$)$_2$CH$_2$, CH(CH$_3$)CH$_2$CH$_2$, CH$_2$CH(CH$_3$)CH$_2$, CH(CH$_3$)CH(CH$_3$), CH(CH$_2$CH$_3$)CH$_2$, C(CH$_3$)$_2$CH$_2$, CH(CH$_2$CH$_2$CH$_3$) and C(CH$_3$)(CH$_2$CH$_3$).

In relation to the terms "$C_{1-6}$-alkyl", "$C_{1-10}$-alkyl", "$C_{1-6}$-alkylene", "$C_{3-6}$-cycloalkyl", "$C_{3-10}$-cycloalkyl", "3 to 7-membered heterocyclyl" and "3 to 10-membered heterocyclyl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; I; NO$_2$; CN; =O; =NH; =N(OH); =N(O—$C_{1-6}$-alkyl); CF$_3$; CF$_2$H; CFH$_2$; CF$_2$Cl; CFCl$_2$; $C_{1-6}$-alkyl; ($C_{1-8}$-alkylene)-OH; C(=O)—H; C(=O)—$C_{1-6}$-alkyl; C(=O)—OH; C(=O)—O—$C_{1-6}$-alkyl; C(=O)—N(H)(OH); C(=O)—NH$_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; OCF$_3$; OCF$_2$H; OCFH$_2$; OCF$_2$Cl; OCFCl$_2$; O—$C_{1-6}$- alkyl; O—(C$_{1-8}$-alkylene)-OH; O—(C$_{1-8}$-alkylene)-O—C$_{1-6}$-alkyl; O—C(=O)—C$_{1-6}$-alkyl; O—C(=O)—O—C$_{1-6}$-alkyl; O—(C=O)—N(H)(C$_{1-6}$-alkyl); O—S(=O)—N(C$_{1-6}$-alkyl)$_2$; O—S(=O)$_2$—C$_{1-6}$-alkyl; O—S(=O)$_2$—OH; O—S(=O)$_2$—O—C$_{1-6}$-alkyl; O—S(=O)$_2$—NH$_2$; O—S(=O)$_2$—N(H)(C$_{1-6}$-alkyl); O—S(=O)$_2$—N(C$_{1-6}$-alkyl)$_2$; NH$_2$; N(H)(C$_{1-6}$-alkyl); N(C$_{1-6}$-alkyl)$_2$; N(H)—C(=O)—C$_{1-6}$-alkyl; N(H)—C(=O)—O—C$_{1-6}$-alkyl; N(H)—C(=O)—NH$_2$; N(H)—C(=O)—N(H)(C$_{1-6}$-alkyl); N(H)—C(=O)—N(C$_{1-6}$-alkyl)$_2$; N(C$_{1-6}$-alkyl)-C(=O)—C$_{1-6}$-alkyl; N(C$_{1-6}$-alkyl)-C(=O)—O—C$_{1-6}$-alkyl; N(C$_{1-6}$-alkyl)-C(=O)—NH$_2$; N(C$_{1-6}$-alkyl)-C(=O)—N(H)(C$_{1-6}$-alkyl); N(C$_{1-6}$-alkyl)-C(=O)—N(C$_{1-6}$-alkyl)$_2$; N(H)—S(=O)$_2$—OH; N(H)—S(=O)$_2$—C$_{1-6}$-alkyl; N(H)—S(=O)$_2$—O—C$_{1-6}$-alkyl; N(H)—S(=O)$_2$—NH$_2$; N(H)—S(=O)$_2$—N(H)(C$_{1-6}$-alkyl); N(H)—S(=O)$_2$—N(C$_{1-6}$-alkyl)$_2$; N(C$_{1-6}$-alkyl)-S(=O)$_2$—OH; N(C$_{1-6}$-alkyl)-S(=O)$_2$—C$_{1-6}$-alkyl; N(C$_{1-6}$-alkyl)-S(=O)$_2$—O—C$_{1-6}$-alkyl; N(C$_{1-6}$-alkyl)-S(=O)$_2$—NH$_2$; N(C$_{1-6}$-alkyl)-S(=O)$_2$—N(H)(C$_{1-6}$-alkyl); N(C$_{1-6}$-alkyl)-S(=O)$_2$—N(C$_{1-6}$-alkyl)$_2$; SH; SCF$_3$; SCF$_2$H; SCFH$_2$; SCF$_2$Cl; SCFCl$_2$; S—C$_{1-6}$-alkyl; S(=O)—C$_{1-6}$-alkyl; S(=O)$_2$—C$_{1-6}$-alkyl; S(=O)$_2$—OH; S(=O)$_2$—O—C$_{1-6}$-alkyl; S(=O)$_2$—NH$_2$; S(=O)$_2$—N(H)(C$_{1-6}$-alkyl); S(=O)$_2$—N(C$_{1-6}$-alkyl)$_2$; C$_{3-6}$-cycloalkyl or 3 to 7 membered heterocyclyl. The term "polysubstituted" with respect to polysubstituted residues and groups includes the polysubstitution of these residues and groups either on different or on the same atoms, for example trisubstituted on the same carbon atom, as in the case of CF$_3$, CH$_2$CF$_3$ or 1,1-difluorocyclohexyl, or at various points, as in the case of CH(OH)—CHCl$_2$ or 1-chloro-3-fluorocyclohexyl. A substituent can if appropriate for its part in turn be mono- or polysubstituted. The multiple substitution can be carried out using the same or using different substituents.

Preferred substituents of "C$_{1-6}$-alkyl", "C$_{1-10}$-alkyl" and "C$_{1-6}$-alkylene" are selected from the group consisting of F; Cl; Br; I; NO$_2$; CF$_3$; CN; =O; =NH; C$_{1-6}$-alkyl; (C$_{1-8}$-alkylene)-OH; C(=O)—H; C(=O)—C$_{1-6}$-alkyl; C(=O)—OH; C(=O)—O—C$_{1-6}$-alkyl; C(=O)—NH$_2$; C(=O)—N(H)(C$_{1-6}$-alkyl); C(=O)—N(C$_{1-6}$-alkyl)$_2$; OH; O—C$_{1-6}$-alkyl; O—C(=O)—C$_{1-6}$-alkyl; O—(C$_{1-8}$-alkylene)-OH; O—(C$_{1-8}$-alkylene)-O—C$_{1-6}$-alkyl; OCF$_3$; NH$_2$; N(H)(C$_{1-6}$-alkyl); N(C$_{1-6}$-alkyl)$_2$; N(H)—C(=O)—C$_{1-6}$-alkyl; N(H)—S(=O)$_2$—C$_{1-6}$-alkyl; N(C$_{1-6}$-alkyl)-S(=O)$_2$—C$_{1-6}$-alkyl; N(H)—C(=O)—NH$_2$; N(H)—C(=O)—N(H)(C$_{1-6}$-alkyl); N(H)—C(=O)—N(C$_{1-6}$-alkyl)$_2$; N(H)—S(=O)$_2$—NH$_2$; N(H)—S(=O)$_2$—N(H)(C$_{1-6}$-alkyl); N(H)—S(=O)$_2$—N(C$_{1-6}$-alkyl)$_2$; N(C$_{1-6}$-alkyl)-S(=O)$_2$—NH$_2$; N(C$_{1-6}$-alkyl)-S(=O)$_2$—N(H)(C$_{1-6}$-alkyl); N(C$_{1-6}$-alkyl)-S(=O)$_2$—N(C$_{1-6}$-alkyl)$_2$; SH; SCF$_3$; S—C$_{1-6}$-alkyl; S(=O)$_2$C$_{1-6}$-alkyl; S(=O)$_2$OH; S(=O)$_2$O—C$_{1-6}$-alkyl and S(=O)$_2$—NH$_2$; S(=O)$_2$—N(H)(C$_{1-6}$-alkyl); and S(=O)$_2$—N(C$_{1-6}$-alkyl)$_2$.

Particularly preferred substituents of "C$_{1-6}$-alkyl", "C$_{1-10}$-alkyl" and "C$_{1-6}$-alkylene" are selected from the group consisting of F; Cl; Br; I; CF$_3$; C(=O)—NH$_2$; C(=O)—N(H)(C$_{1-6}$-alkyl); C(=O)—N(C$_{1-6}$-alkyl)$_2$; OH; O—C$_{1-6}$-alkyl; O—(C$_{1-8}$-alkylene)-OH; O—(C$_{1-8}$-alkylene)-O—C$_{1-6}$-alkyl; NH$_2$; N(H)(C$_{1-6}$-alkyl); N(C$_{1-6}$-alkyl)$_2$; N(H)—C(=O)—C$_{1-6}$-alkyl; N(H)—S(=O)$_2$—C$_{1-6}$-alkyl; N(C$_{1-6}$-alkyl)-S(=O)$_2$—C$_{1-6}$-alkyl; N(H)—S(=O)$_2$—NH$_2$; SH; S—C$_{1-6}$-alkyl; S(=O)$_2$C$_{1-6}$-alkyl and S(=O)$_2$—N(H)(C$_{1-6}$-alkyl).

Preferred substituents of "C$_{3-6}$-cycloalkyl", "C$_{3-10}$-cycloalkyl", "3 to 7-membered heterocyclyl" and "3 to 10-membered heterocyclyl" are selected from the group consisting of F; Cl; Br; I; NO$_2$; CF$_3$; CN; =O; C$_{1-6}$-alkyl; C$_{3-6}$-cycloalkyl or 3 to 7 membered heterocyclyl; C$_{3-6}$-cycloalkyl or 3 to 7 membered heterocyclyl, each bridged via a C$_{1-8}$-alkylene; CHO; C(=O)—C$_{1-6}$-alkyl; CO$_2$H; C(=O)O—C$_{1-6}$-alkyl; CONH$_2$; C(=O)NH—C$_{1-6}$-alkyl; C(=O)N(C$_{1-6}$-alkyl)$_2$; OH; O—C$_{1-6}$-alkyl; OCF$_3$; O—(C$_{1-8}$-alkylene)-OH; O—(C$_{1-8}$-alkylene)-O—C$_{1-6}$-alkyl; O—C(=O)—C$_{1-6}$-alkyl; NH$_2$; NH—C$_{1-6}$-alkyl; N(C$_{1-6}$-alkyl)$_2$; NH—C(=O)—C$_{1-6}$-alkyl; SH; S—C$_{1-6}$-alkyl; SCF$_3$; S(=O)$_2$—C$_{1-6}$-alkyl; S(=O)$_2$OH; S(=O)$_2$O—C$_{1-6}$-alkyl and S(=O)$_2$—NH—C$_{1-6}$-alkyl.

In relation to the terms "aryl" and "heteroaryl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; NO$_2$; CN; CF$_3$; CF$_2$H; CFH$_2$; CF$_2$Cl; CFCl$_2$; C$_{1-6}$-alkyl; C$_{3-6}$-cycloalkyl; 3 to 7 membered heterocyclyl; aryl; heteroaryl; aryl, heteroaryl, C$_{3-6}$-cycloalkyl or 3 to 7 membered heterocyclyl, each connected via a C$_{1-8}$-alkylene; C(=O)H; C(=O)—(C$_{1-6}$-alkyl); C(=O)—(C$_{3-6}$-cycloalkyl); C(=O)-(3 to 7 membered heterocyclyl); C(=O)-(aryl); C(=O)-(heteroaryl); C(=O)OH; C(=O)—O(C$_{1-6}$-alkyl); C(=O)—O(C$_{3-6}$-cycloalkyl); C(=O)—O (3 to 7 membered heterocyclyl); C(=O)—O (aryl); C(=O)—O(heteroaryl); C(=O)—NH$_2$; C(=O)—N(H)(C$_{1-6}$-alkyl); C(=O)—N(H)(C$_{3-6}$-cycloalkyl); C(=O)—N(H)(3 to 7 membered heterocycloalkyl); C(=O)—N(H)(aryl); C(=O)—N(H)(heteroaryl); C(=O)—N(C$_{1-6}$-alkyl)$_2$; C(=O)—N(C$_{1-6}$-alkyl)(C$_{3-6}$-cycloalkyl); C(=O)—N(C$_{1-6}$-alkyl)(3 to 7 membered heterocyclyl); C(=O)—N(C$_{1-6}$-alkyl)(aryl); C(=O)—N(C$_{1-6}$-alkyl)(heteroaryl); OH; =O; O—(C$_{1-6}$-alkyl); O—(C$_{3-6}$-cycloalkyl); O-(3 to 7 membered heterocyclyl); O-(aryl); O-(heteroaryl); OCF$_3$; OCF$_2$H; OCFH$_2$; OCF$_2$Cl; OCFCl$_2$; O—C(=O)—(C$_{1-6}$-alkyl); O—C(=O)—(C$_{3-6}$-cycloalkyl); O—C(=O)-(3 to 7 membered heterocyclyl); O—C(=O)-(aryl); C(=O)-(heteroaryl); O—C(=O)—NH$_2$; O—C(=O)—N(H)(C$_{1-6}$-alkyl); O—C(=O)—N(H)(C$_{3-6}$-cycloalkyl); O—C(=O)—N(H)(3 to 7 membered heterocyclyl); O—C(=O)—N(H)(aryl); O—C(=O)—N(H)(heteroaryl); O—C(=O)—N(C$_{1-6}$-alkyl)$_2$; O—C(=O)—N(C$_{1-6}$-alkyl)(C$_{3-6}$-cycloalkyl); O—C(=O)—N(C$_{1-6}$-alkyl)(3 to 7 membered heterocyclyl); O—C(=O)—N(C$_{1-6}$-alkyl)(aryl); O—C(=O)—N(C$_{1-6}$-alkyl)(heteroaryl); NH$_2$; N(H)(C$_{1-6}$-alkyl); N(H)(C$_{3-6}$-cycloalkyl); N(H)(3 to 7 membered heterocyclyl); N(H)(aryl); N(H)(heteroaryl); N(C$_{1-6}$-alkyl)$_2$; N(C$_{1-6}$-alkyl)(C$_{3-6}$-cycloalkyl); N(C$_{1-6}$-alkyl)(3 to 7 membered heterocyclyl); N(C$_{1-6}$-alkyl)(aryl); N(C$_{1-6}$-alkyl)(heteroaryl); N(H)—C(=O)—(C$_{1-6}$-alkyl); N(H)—C(=O)—(C$_{3-6}$-cycloalkyl); N(H)—C(=O)-(3 to 7 membered heterocyclyl); N(H)—C(=O)-(aryl); N(H)—C(=O)-(heteroaryl); N(C$_{1-6}$-alkyl)-C(=O)—(C$_{1-6}$-alkyl); N(C$_{1-6}$-alkyl)-C(=O)—(C$_{3-6}$-cycloalkyl); N(C$_{1-6}$-alkyl)-C(=O)-(3 to 7 membered heterocyclyl); N(C$_{1-6}$-alkyl)-C(=O)-(aryl); N(C$_{1-6}$-alkyl)-C(=O)-(heteroaryl); N(H)—S(=O)$_2$—(C$_{1-6}$-alkyl); N(H)—S(=O)$_2$—(C$_{3-6}$-cycloalkyl); N(H)—S(=O)$_2$-(3 to 7 membered heterocyclyl); N(H)—S(=O)$_2$-(aryl); N(H)—S(=O)$_2$-(heteroaryl); N(C$_{1-4}$-alkyl)-S(=O)$_2$—(C$_{1-6}$-alkyl); N(C$_{1-6}$-alkyl)-S(=O)$_2$—(C$_{3-6}$-cycloalkyl); N(C$_{1-6}$-alkyl)-S(=O)$_2$-(3 to 7 membered heterocyclyl); N(C$_{1-6}$-alkyl)-S(=O)$_2$-(aryl); N(C$_{1-6}$-alkyl)-S(=O)$_2$-(heteroaryl); N(H)—C(=O)—O(C$_{1-6}$-alkyl); N(H)—C(=O)—O(C$_{3-6}$-cycloalkyl); N(H)—C(=O)—O (3 to 7 membered heterocyclyl); N(H)—C(=O)—O(aryl); N(H)—C(=O)—

O(heteroaryl); N($C_{1-6}$-alkyl)-C(=O)—O($C_{1-6}$-alkyl); N($C_{1-6}$-alkyl)-C(=O)—O($C_{3-6}$-cycloalkyl); N($C_{1-6}$-alkyl)-C(=O)—O (3 to 7 membered heterocyclyl); N($C_{1-6}$-alkyl)-C(=O)—O(aryl); N($C_{1-6}$-alkyl)-C(=O)—O(heteroaryl); N(H)—C(=O)—NH$_2$; N(H)—C(=O)—N(H)($C_{1-6}$-alkyl); N(H)—C(=O)—N(H)($C_{3-6}$-cycloalkyl); N(H)—C(=O)—N(H)(3 to 7 membered heterocyclyl); N(H)—C(=O)—N(H)(aryl); N(H)—C(=O)—N(H)(heteroaryl); N($C_{1-6}$-alkyl)-C(=O)—NH$_2$; N($C_{1-6}$-alkyl)-C(=O)—N(H)($C_{1-6}$-alkyl); N($C_{1-6}$-alkyl)-C(=O)—N(H)($C_{3-6}$-cycloalkyl); N($C_{1-6}$-alkyl)-C(=O)—N(H)(3 to 7 membered heterocyclyl); N($C_{1-6}$-alkyl)-C(=O)—N(H)(aryl); N($C_{1-6}$-alkyl)-C(=O)—N(H)(heteroaryl); N(H)—C(=O)—N($C_{1-6}$-alkyl)$_2$; N(H)—C(=O)—N($C_{1-6}$-alkyl)($C_{3-6}$-cycloalkyl); N(H)—C(=O)—N($C_{1-6}$-alkyl)(3 to 7 membered heterocyclyl); N(H)—C(=O)—N($C_{1-6}$-alkyl)(aryl); N(H)—C(=O)—N($C_{1-6}$-alkyl) (heteroaryl); N($C_{1-6}$-alkyl)-C(=O)—N($C_{1-6}$-alkyl)$_2$; N($C_{1-6}$-alkyl)-C(=O)—N($C_{1-6}$-alkyl)($C_{3-6}$-cycloalkyl); N($C_{1-6}$-alkyl)-C(=O)—N($C_{1-6}$-alkyl)(3 to 7 membered heterocyclyl); N($C_{1-6}$-alkyl)-C(=O)—N($C_{1-6}$-alkyl)(aryl); N($C_{1-6}$-alkyl)-C(=O)—N($C_{1-6}$-alkyl) heteroaryl); SH; S—($C_{1-6}$-alkyl); S—($C_{3-6}$-cycloalkyl); S-(3 to 7 membered heterocyclyl); S-(aryl); S-(heteroaryl); SCF$_3$; S(=O)$_2$OH; S(=O)—($C_{1-6}$-alkyl); S(=O)—($C_{3-6}$-cycloalkyl); S(=O)-(3 to 7 membered heterocyclyl); S(=O)-(aryl); S(=O)-(heteroaryl); S(=O)$_2$—($C_{1-6}$-alkyl); S(=O)$_2$—($C_{3-6}$-cycloalkyl); S(=O)$_2$-(3 to 7 membered heterocyclyl); S(=O)$_2$-(aryl); S(=O)$_2$-(heteroaryl); S(=O)$_2$—O($C_{1-6}$-alkyl); S(=O)$_2$—O($C_{3-6}$-cycloalkyl); S(=O)$_2$—O (3 to 7 membered heterocyclyl); S(=O)$_2$—O (aryl); S(=O)$_2$—O(heteroaryl); S(=O)$_2$—N(H)($C_{1-6}$-alkyl); S(=O)$_2$—N(H)($C_{3-6}$-cycloalkyl); S(=O)$_2$—N(H)(3 to 7 membered heterocyclyl); S(=O)$_2$—N(H)(aryl); S(=O)$_2$—N(H)(heteroaryl); S(=O)$_2$—N($C_{1-6}$-alkyl)$_2$; S(=O)$_2$—N($C_{1-6}$-alkyl)($C_{3-6}$-cycloalkyl); S(=O)$_2$—N($C_{1-6}$-alkyl)(3 to 7 membered heterocyclyl); S(=O)$_2$—N($C_{1-6}$-alkyl)(aryl) and S(=O)$_2$—N($C_{1-6}$-alkyl)(heteroaryl).

Preferred substituents of "aryl" and "heteroaryl" are selected from the group consisting of F; Cl; Br; NO$_2$; CN; CF$_3$; CF$_2$H; CFH$_2$; CF$_2$Cl; CFCl$_2$; $C_{1-6}$-alkyl; aryl; heteroaryl; $C_{3-6}$-cycloalkyl; 3 to 6 membered heterocyclyl; aryl, heteroaryl, $C_{3-6}$-cycloalkyl or 3 to 6 membered heterocycloaliphatic, each connected via a $C_{1-8}$-alkylene; C(=O)—H; C(=O)—$C_{1-6}$-alkyl; C(=O)aryl; C(=O)heteroaryl; C(=O)—OH; C(=O)—O—$C_{1-6}$-alkyl; C(=O)O-aryl; C(=O)O-heteroaryl; CO—NH$_2$; C(=O)—N(H)$C_{1-6}$-alkyl; C(=O)—N($C_{1-6}$-alkyl)$_2$; C(=O)NH-aryl; C(=O)N(aryl)$_2$; C(=O)NH-heteroaryl; C(=O)—N(heteroaryl)$_2$; C(=O)N($C_{1-6}$-alkyl)(aryl); C(=O)N($C_{1-6}$-alkyl)(heteroaryl); C(=O)N(heteroaryl)(aryl); OH; OCF$_3$; OCF$_2$H; OCFH$_2$; OCF$_2$Cl; OCFCl$_2$; O—$C_{1-6}$-alkyl; O-benzyl; O-aryl; O-heteroaryl; O—C(=O)—$C_{1-6}$-alkyl; O—C(=O)aryl; O—C(=O)heteroaryl; O—C(=O)—O—$C_{1-6}$-alkyl; O—(C=O)—N(H)$C_{1-6}$-alkyl; O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—NH$_2$; O—S(=O)$_2$—N(H)$C_{1-6}$-alkyl; O—S(=O)$_2$—N($C_{1-6}$-alkyl)$_2$; NH$_2$; N(H)$C_{1-6}$-alkyl; N($C_{1-6}$-alkyl)$_2$; N(H)—C(=O)—$C_{1-6}$-alkyl; N(H)—C(=O)-aryl; N(H)—C(=O)-heteroaryl; N(H)—C(=O)—O—$C_{1-6}$-alkyl; N(H)C(=O)—NH$_2$; N(H)—C(=O)—N(H)$C_{1-6}$-alkyl; N(H)—C(=O)—N($C_{1-6}$-alkyl)$_2$; N($C_{1-6}$-alkyl)-C(=O)$C_{1-6}$-alkyl; N($C_{1-6}$-alkyl)-C(=O)—O—$C_{1-6}$-alkyl; N($C_{1-6}$-alkyl)C(=O)—NH$_2$; N($C_{1-6}$-alkyl)-C(=O)—N(H)$C_{1-6}$-alkyl; N($C_{1-6}$-alkyl)-C(=O)—N($C_{1-6}$-alkyl)$_2$; N(H)—S(=O)$_2$—OH; N(H)—S(=O)$_2$—$C_{1-6}$-alkyl; N(H)—S(=O)$_2$—O—$C_{1-6}$-alkyl; N(H)—S(=O)$_2$—NH$_2$; N(H)S(=O)$_2$—N(H)$C_{1-6}$-alkyl; N(H)—S(=O)$_2$—N($C_{1-6}$-alkyl)$_2$; N($C_{1-6}$-alkyl)-S(=O)$_2$—OH; N($C_{1-6}$-alkyl)-S(=O)$_2$($C_{1-6}$-alkyl); N($C_{1-6}$-alkyl)-S(=O)$_2$—O($C_{1-6}$-alkyl); N($C_{1-6}$-alkyl)-S(=O)$_2$—NH$_2$; N($C_{1-6}$-alkyl)-S(=O)$_2$—N(H)$C_{1-6}$-alkyl; N($C_{1-6}$-alkyl)S(=O)$_2$—N($C_{1-6}$-alkyl)$_2$; SH; SCF$_3$; SCF$_2$H; SCFH$_2$; SCF$_2$Cl; SCFCl$_2$; S—$C_{1-6}$-alkyl; S-benzyl; S-aryl; S-heteroaryl; S(=O)—$C_{1-6}$-alkyl; S(=O)$_2$—$C_{1-6}$-alkyl; S(=O)$_2$-aryl; S(=O)$_2$-heteroaryl; S(=O)$_2$—OH; S(=O)$_2$—O$C_{1-6}$-alkyl; S(=O)$_2$O-aryl; S(=O)$_2$O-heteroaryl; S(=O)$_2$—NH$_2$; S(=O)$_2$—N(H)$C_{1-6}$-alkyl, S(=O)$_2$—N(H)-aryl; S(=O)$_2$—N(H)-heteroaryl and S(=O)$_2$—N($C_{1-6}$-alkyl)$_2$.

More preferred substituents of "aryl" and "heteroaryl" are selected from the group consisting of F; Cl; CF$_3$; CN; $C_{1-6}$-alkyl; C(=O)—OH; C(=O)—O—$C_{1-6}$-alkyl; CO—NH$_2$; C(=O)—N(H)$C_{1-6}$-alkyl; C(=O)—N($C_{1-6}$-alkyl)$_2$; OH; O—$C_{1-6}$-alkyl; O—C(=O)—$C_{1-6}$-alkyl; OCF$_3$; OCHF$_2$; OCH$_2$F; NH$_2$; N(H)$C_{1-6}$-alkyl; N($C_{1-6}$-alkyl)$_2$; N(H)—C(=O)—$C_{1-6}$-alkyl; N($C_{1-6}$-alkyl)-C(=O)$C_{1-6}$-alkyl; N(H)—S(=O)$_2$—$C_{1-6}$-alkyl; N($C_{1-6}$-alkyl)-S(=O)$_2$($C_{1-6}$-alkyl); N(H)C(=O)NH$_2$; N(H)C(=O)—N(H)$C_{1-6}$-alkyl; N(H)—C(=O)—N($C_{1-6}$-alkyl)$_2$; N($C_{1-6}$-alkyl)-C(=O)—NH$_2$; N($C_{1-6}$-alkyl)C(=O)—N(H)$C_{1-6}$-alkyl; N($C_{1-6}$-alkyl)-C(=O)—N($C_{1-6}$-alkyl)$_2$; S(=O)$_2$$C_{1-6}$-alkyl; S(=O)$_2$—NH$_2$; S(=O)$_2$—N(H)$C_{1-6}$-alkyl and S(=O)$_2$—N($C_{1-6}$-alkyl)$_2$.

The compounds according to the invention are defined by substituents, for example by $R^1$, $R^2$ and $R^3$ ($1^{st}$ generation substituents) which are for their part if appropriate themselves substituted ($2^{nd}$ generation substituents). Depending on the definition, these substituents of the substituents can for their part be resubstituted ($3^{rd}$ generation substituents). If, for example, $R^1$=a $C_{1-6}$-alkyl ($1^{st}$ generation substituent), then the $C_{1-6}$-alkyl can for its part be substituted, for example with a NH—$C_{1-6}$-alkyl ($2^{nd}$ generation substituent). This produces the functional group $R^1$=($C_{1-6}$-alkyl-NH—$C_{1-6}$-alkyl). The NH—$C_{1-6}$-alkyl can then for its part be resubstituted, for example with Cl ($3^{rd}$ generation substituent). Overall, this produces the functional group $R^1$=$C_{1-6}$-alkyl-NH—$C_{1-6}$-alkyl, wherein the $C_{1-6}$-alkyl of the NH—$C_{1-6}$-alkyl is substituted by Cl. However, in a preferred embodiment, the $3^{rd}$ generation substituents may not be resubstituted, i.e. there are then no $4^{th}$ generation substituents. If a residue occurs multiply within a molecule, then this residue can have respectively different meanings for various substituents: if, for example, both $R^1$ and $R^2$ denote a 3 to 10 membered heterocyclyl, then the 3 to 10 membered heterocyclyl can e.g. represent morpholinyl for $R^1$ and can represent piperazinyl for $R^2$.

Within the scope of the present invention, the symbols

or ------ used in the formulae denotes a link of a corresponding residue to the respective superordinate general structure.

In one embodiment of the first aspect of the invention, the compound according to general formula (I) is characterized in that $R^1$, $R^2$ and $R^3$ are each independently selected from the group consisting of H; F; Cl; Br; I; NO$_2$; CN; $C_{1-6}$-alkyl; CF$_3$; CF$_2$H; CFH$_2$; CF$_2$Cl; CFCl$_2$; C(=O)—H; C(=O)—$C_{1-6}$-alkyl; C(=O)—OH; C(=O)—O—$C_{1-6}$-alkyl; C(=O)—N(H)(OH); C(=O)—NH$_2$; C(=O)—N(H)($C_{1-6}$-alkyl); C(=O)—N($C_{1-6}$-alkyl)$_2$; C(=N—OH)—H;

C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—$NH_2$; O—S(=O)$_2$—N(H)($C_{1-6}$-alkyl); O—S(=O)$_2$—N($C_{1-6}$-alkyl)$_2$; $NH_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—$NH_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—$NH_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—$NH_2$; N(H)—S(=O)$_2$—N(H)($C_{1-6}$-alkyl); N(H)—S(=O)$_2$—N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—$NH_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$, $C_{3-6}$-cycloalkyl or 3 to 7 membered heterocyclyl, wherein in each case said $C_{1-6}$-alkyl may be branched or unbranched and may be unsubstituted or mono- or polysubstituted;

and wherein in each case said $C_{3-6}$-cycloalkyl or 3 to 7 membered heterocyclyl may be unsubstituted or mono- or polysubstituted.

Preferably, $R^1$, $R^2$ and $R^3$ are each independently selected from the group consisting of H; F; Cl; CN; $C_{1-6}$-alkyl; $CF_3$; $CF_2H$; $CFH_2$; OH; $OCF_3$; O—$C_{1-6}$-alkyl; O—C(=O)—$C_{1-6}$-alkyl; $NH_2$; N(H)($C_{1-6}$-alkyl); N($C_{1-6}$-alkyl)$_2$; $SCF_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); S(=O)$_2$—N($C_{1-6}$alkyl)$_2$, wherein in each case $C_{1-6}$-alkyl may be branched or unbranched, or $C_{3-6}$-cycloalkyl, unsubstituted or mono- or polysubstituted.

Still preferably, $R^1$, $R^2$ and $R^3$ are each independently selected from the group consisting of H; F; Cl; CN; $C_{1-6}$-alkyl; $CF_3$; $CF_2H$; $CFH_2$; OH; $OCF_3$; $OCF_2H$; $OCFH_2$; O—$C_{1-6}$-alkyl; O—C(=O)—$C_{1-6}$-alkyl; $NH_2$; N(H)($C_{1-6}$-alkyl); N($C_{1-6}$-alkyl)$_2$; $SCF_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); or S(=O)$_2$—N($C_{1-6}$-alkyl)$_2$, wherein in each case $C_{1-6}$-alkyl may be branched or unbranched.

More preferably, $R^1$, $R^2$ and $R^3$ are independently selected from the group consisting of H, F, Cl, $CFH_2$, $CF_2H$, $CF_3$, CN, $CH_2$—$OCH_3$, S(=O)$_2$—$CH_3$, $OCF_3$, $CH_3$, O—$CH_3$, O—$CH_2CH_3$ and N($CH_3$)$_2$.

Even more preferably, $R^1$, $R^2$ and $R^3$ are independently selected from the group consisting of H, F, Cl, CN, $CFH_2$, $CF_2H$, $CF_3$, $OCF_3$, $CH_3$, S(=O)$_2$—$CH_3$, $OCH_3$, and $OCH_2CH_3$.

Particularly preferred, $R^1$, $R^2$ and $R^3$ are independently selected from the group consisting of H, F, Cl, $CF_3$, $CH_3$ and $OCH_3$. In one particular preferred embodiment of the first aspect of the invention, the compound according to general formula (I) is characterized in that $R^1$, $R^2$ and $R^3$ denote H.

In another particular preferred embodiment of the first aspect of the invention, the compound according to general formula (I) is characterized in that at least one of $R^1$, $R^2$ and $R^3$ is ≠H.

In one embodiment of the first aspect of the invention, the compound according to general formula (I) is characterized in that n represents 1 or 2, preferably n represents 1.

In another embodiment of the first aspect of the invention, the compound according to general formula (I) is characterized in that m represents 0.

In one particular preferred embodiment of the first aspect of the invention, the compound according to general formula (I) is characterized in that n represents 1 and m represents 0.

Yet another embodiment of the first aspect of the invention is the compound according to general formula (I) which is characterized in that n represents 1 and m represents 0; and $R^1$, $R^2$ and $R^3$ are each independently of one another selected from the group consisting of H; F; Cl; CN; $CF_3$; $CF_2H$; $CFH_2$; OH; $OCF_3$; $OCF_2H$; $OCFH_2$; O—$C_{1-6}$-alkyl; O—C(=O)—$C_{1-6}$-alkyl; $NH_2$; N(H)($C_{1-6}$-alkyl); N($C_{1-6}$-alkyl)$_2$; $SCF_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl) or S(=O)$_2$—N($C_{1-6}$-alkyl)$_2$, wherein in each case $C_{1-6}$-alkyl may be branched or unbranched.

In another embodiment of the first aspect of the invention, the compound according to general formula (I) is characterized in that $R^4$ represents $CH_2F$, $CHF_2$ or $CF_3$. Preferably, $R^4$ represents $CHF_2$ or $CF_3$.

A particularly preferred compound according to formula (I) is characterized in that $R^4$ represents $CF_3$.

Another particularly preferred compound according to formula (I) is characterized in that $R^4$ represents $CHF_2$.

In a further embodiment of the first aspect of the invention, the compound according to general formula (I) is characterized in that $R^5$ represents H, $C_{1-6}$-alkyl, branched or unbranched, unsubstituted or mono- or poly-substituted, $C_{3-6}$-cycloalkyl or 3 to 7 membered heterocyclyl, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), wherein in each case $C_{1-6}$-alkyl may be branched or unbranched and may be unsubstituted or mono- or polysubstituted.

Preferably, $R^5$ is selected from the group consisting of H, methyl, ethyl, n-propyl, iso-propyl, n-butyl, sec-butyl, iso-butyl, tert-butyl, cyclopropyl, methoxy, ethoxy, methylsulfonyl, 2-oxetyl, 3-oxetyl, 2-tetrahydrofuranyl and 3-tetrahydrofuranyl.

More preferably, $R^5$ is selected from the group consisting of H, methyl, ethyl, iso-propyl and cyclopropyl. Even more preferably, $R^5$ represents H or methyl.

In a particularly preferred embodiment of the invention, the compound according to general formula (I) is characterized in that $R^5$ represents methyl ($CH_3$). In another particularly preferred embodiment of the invention, the compound according to general formula (I) is characterized in that $R^5$ represents H.

In another embodiment of the first aspect of the invention, the compound according to general formula (I) is selected from a compound according to general formula (Ia) or from a compound according to general formula (Ib),

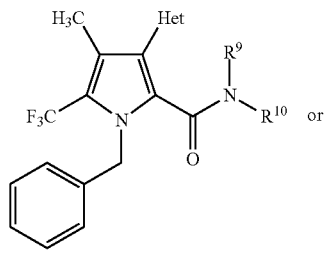

(Ia)

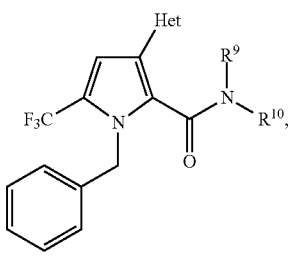

(Ib)

wherein Het, R⁹ and R¹⁰ are defined as above.

In another embodiment of the first aspect of the invention, the compound according to general formula (I) is characterized in that Het is selected from the group consisting of pyrrol, furanyl, thienyl, pyrazolyl, imidazolyl, isoxazolyl, isothiazolyl, oxazolyl, thiazolyl, triazolyl, oxadiazolyl, thiadiazolyl, tetrazolyl, indolyl, benzofuranyl, benzothienyl, indazolyl, benzimidazolyl, benzoxazolyl, benzothiazolyl, benzotriazolyl, pyridinyl, pyrazinyl, pyrimidinyl, pyridazinyl, triazinyl, quinolinyl, isoquinolinyl, quinoxalinyl, quinazolinyl, cinnolinyl, 1,5-naphthyridinyl, 1,6-naphthyridinyl, 1,7-naphthyridinyl, 1,8-naphthyridinyl, 2,3-naphthyridinyl, 2,6-naphthyridinyl and 2,7-naphthyridinyl, each substituted by zero or one or two or three substituents of the group consisting of $R^6$, $R^7$ and $R^8$.

Preferably, Het is selected from the group consisting of pyrrol, thienyl, pyrazolyl, imidazolyl, isoxazolyl, oxazolyl, thiazolyl, pyridinyl, pyrazinyl, pyrimidinyl and pyridazinyl, each substituted by zero or one or two or three substituents of the group consisting of $R^6$, $R^7$ and $R^8$.

In another embodiment of the first aspect of the invention, the compound according to general formula (I) is characterized in that $R^6$, $R^7$ and $R^8$ are independently selected from the group consisting of F; Cl; CN; $C_{1-6}$-alkyl; $CF_3$; $CF_2H$; $CFH_2$; OH; $OCF_3$; $OCF_2H$; $OCFH_2$; O—$C_{1-6}$-alkyl; O—C(=O)—$C_{1-6}$-alkyl; $NH_2$; N(H)($C_{1-6}$-alkyl); N($C_{1-6}$-alkyl)$_2$; $SCF_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$; $C_{3-6}$-cycloalkyl or O—$C_{3-6}$-cycloalkyl, wherein in each case said $C_{1-6}$-alkyl may be branched or unbranched and wherein in each case said $C_{3-6}$-cycloalkyl may be unsubstituted or mono- or polysubstituted.

Preferably, $R^6$, $R^7$ and $R^8$ are each independently selected from the group consisting of F; Cl; CN; $C_{1-6}$-alkyl; $CF_3$; $CF_2H$; $CFH_2$; OH; $OCF_3$; $OCF_2H$; $OCFH_2$; O—$C_{1-6}$-alkyl; S(=O)—$C_{1-6}$-alkyl; S(=O)$_2$—$C_{1-6}$-alkyl; cyclopropyl and O-cyclopropyl.

More preferably, Het is selected from the group consisting of pyrrol, thienyl, pyrazolyl, imidazolyl, isoxazolyl, oxazolyl, thiazolyl, pyridinyl, pyrazinyl, pyrimidinyl and pyridazinyl, each substituted by zero or one or two or three substituents of the group consisting of $R^6$, $R^7$ and $R^8$, wherein $R^6$, $R^7$ and $R^8$ are each independently of one another selected from the group consisting of F; Cl; CN; $C_{1-6}$-alkyl; $CF_3$; $CF_2H$; $CFH_2$; OH; $OCF_3$; $OCF_2H$; $OCFH_2$; O—$C_{1-6}$-alkyl; $NH_2$; N(H)($C_{1-6}$-alkyl); N($C_{1-6}$-alkyl)$_2$; $SCF_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$; $C_{3-6}$-cycloalkyl or O—$C_{3-6}$-cycloalkyl, wherein in each case said $C_{1-6}$-alkyl may be branched or unbranched and wherein in each case said $C_{3-6}$-cycloalkyl may be unsubstituted or mono- or polysubstituted.

Even more preferably, Het is selected from the group consisting of pyrrol, thienyl, pyrazolyl, imidazolyl, isoxazolyl, oxazolyl, thiazolyl, pyridinyl, pyrazinyl, pyrimidinyl and pyridazinyl, each substituted by zero or one or two or three substituents of the group consisting of $R^6$, $R^7$ and $R^8$, wherein $R^6$, $R^7$ and $R^8$ are each independently of one another selected from the group consisting of F; Cl; CN; $C_{1-6}$-alkyl; $CF_3$; $CF_2H$; $CFH_2$; OH; $OCF_3$; $OCF_2H$; $OCFH_2$; O—$C_{1-6}$-alkyl; S(=O)—$C_{1-6}$-alkyl; S(=O)$_2$—$C_{1-6}$-alkyl; cyclopropyl and O-cyclopropyl.

Yet more preferably, Het is selected from the group consisting of
pyridin-2-yl, pyridin-3-yl, pyridin-4-yl, pyrazin-2-yl, pyrimidin-2-yl, pyrimidin-4-yl, pyrimidin-5-yl, pyridazin-3-yl, pyridazin-4-yl, thiophen-2-yl, thiophen-3-yl, pyrazol-3-yl, pyrazol-4-yl, pyrazol-5-yl, imidazol-2-yl, isoxazol-3-yl, isoxazol-4-yl, isoxazol-5-yl, oxazol-2-yl, oxazol-4-yl, oxazol-5-yl, thiazol-2-yl, thiazol-4-yl, thiazol-5-yl,
each substituted by zero or one or two substituents of the group consisting of $R^6$ and $R^7$, wherein $R^6$ and $R^7$ are each independently of one another selected from the group consisting of F; Cl; CN; $CF_3$; $CH_3$; OH; $OCF_3$, $OCH_3$, $S(O)CH_3$ and $S(O)_2CH_3$.

Particularly preferred, Het is selected from the group consisting of 6-hydroxy-pyridin-3-yl, 3-fluoro-5-(trifluoromethyl)-pyridin-2-yl, 6-cyano-4-methyl-pyridin-3-yl, 6-chloro-4-methyl-pyridin-3-yl, 6-methoxy-4-methyl-pyridin-3-yl, 2-cyano-4-methyl-pyridin-5-yl, pyridin-2-yl, 3-fluoro-pyridin-2-yl, 4-fluoro-pyridin-2-yl, 5-fluoro-pyridin-2-yl, 6-fluoro-pyridin-2-yl, 3-chloro-pyridin-2-yl, 4-chloro-pyridin-2-yl, 5-chloro-pyridin-2-yl, 6-chloro-pyridin-2-yl, 3-cyano-pyridin-2-yl, 4-cyano-pyridin-2-yl, 5-cyano-pyridin-2-yl, 6-cyano-pyridin-2-yl, 3-methoxy-pyridin-2-yl, 4-methoxy-pyridin-2-yl, 5-methoxy-pyridin-2-yl, 6-methoxy-pyridin-2-yl, 3-methyl-pyridin-2-yl, 4-methyl-pyridin-2-yl, 5-methyl-pyridin-2-yl, 6-methyl-pyridin-2-yl, 3-trifluoromethyl-pyridin-2-yl, 4-trifluoromethyl-pyridin-2-yl, 5-trifluoromethyl-pyridin-2-yl, 6-trifluoromethyl-pyridin-2-yl, 4-methylsulfinyl-pyridin-2-yl, 4-chloro-6-methylsulfinyl-pyridin-2-yl, pyridin-3-yl, 2-fluoro-pyridin-3-yl, 4-fluoro-pyridin-3-yl, 5-fluoro-pyridin-3-yl, 6-fluoro-pyridin-3-yl, 2-chloro-pyridin-3-yl, 4-chloro-pyridin-3-yl, 5-chloro-pyridin-3-yl, 6-chloro-pyridin-3-yl, 2-cyano-pyridin-3-yl, 4-cyano-pyridin-3-yl, 5-cyano-pyridin-3-yl, 6-cyano-pyridin-3-yl, 2-methoxy-pyridin-3-yl, 4-methoxy-pyridin-3-yl, 5-methoxy-pyridin-3-yl, 6-methoxy-pyridin-3-yl, 2-methyl-pyridin-3-yl, 4-methyl-pyridin-3-yl, 5-methyl-pyridin-3-yl, 6-methyl-pyridin-3-yl, 2-trifluoromethyl-pyridin-3-yl, 4-trifluoromethyl-pyridin-3-yl, 5-trifluoromethyl-pyridin-3-yl, 6-trifluoromethyl-pyridin-3-yl, pyridin-4-yl, 2-fluoro-pyridin-4-yl, 3-fluoro-pyridin-4-yl, 2-chloro-pyridin-4-yl, 3-chloro-pyridin-4-yl, 2-cyano-pyridin-4-yl, 3-cyano-pyridin-4-yl, 2-methoxy-pyridin-4-yl, 3-methoxy-pyridin-4-yl, 2-methyl-pyridin-4-yl, 3-methyl-pyridin-4-yl, 2-trifluoromethyl-pyridin-4-yl, 3-trifluoromethyl-pyridin-4-yl, pyrimidin-2-yl, 4-fluoro-pyrimidin-2-yl, 4-chloro-pyrimidin-2-yl, 5-fluoro-pyrimidin-2-yl, 5-chloro-pyrimidin-2-yl, 4-methoxy-pyrimidin-2-yl, 4-methyl-pyrimidin-2-yl, 5-methoxy-pyrimidin-2-yl, 5-methyl-pyrimidin-2-yl, 4-trifluoromethyl-pyrimidin-2-yl, 4-cyano-pyrimidin-2-yl, 5-trifluoromethyl-pyrimidin-2-yl, 5-cyano-pyrimidin-2-yl, pyrimidin-4-yl, 2-fluoro-pyrimidin-4-yl, 2-chloro-pyrimidin-4-yl, 5-fluoro-pyrimidin-4-yl, 5-chloro-pyrimidin-4-yl, 6-fluoro-pyrimidin-4-yl, 6-chloro-pyrimidin-4-yl, 2-trifluoromethyl-pyrimidin-4-yl, 2-cyano-pyrimidin-4-yl, 5-trifluoromethyl-pyrimidin-4-yl, 5-cyano-pyrimidin-4-yl, 6-trifluoromethyl-pyrimidin-4-yl, 6-cyano-pyrimidin-4-yl, 2-methyl-pyrimidin-4-yl, 2-methoxy-pyrimidin-4-yl, 5-methyl-pyrimidin-4-yl, 5-methoxy-pyrimidin-4-yl, 6-methyl-pyrimidin-4-yl, 6-methoxy-pyrimidin-4-yl, pyrimidin-5-yl, 2-fluoro-pyrimidin-5-yl, 2-chloro-pyrimidin-5-yl, 4-fluoro-pyrimidin-5-yl, 4-chloro-pyrimidin-5-yl, 2-methyl-pyrimidin-5-yl, 2-methoxy-pyrimidin-5-yl, 4-methyl-pyrimidin-5-yl, 4-methoxy-pyrimidin-5-yl, 2-trifluoromethyl-pyrimidin-5-yl, 2-cyano-pyrimidin-5-yl, 4-trifluoromethyl-pyrimidin-5-yl, 4-cyano-pyrimidin-5-yl, pyrazin-2-yl, 2-methoxy-pyrazin-2-yl, 5-methoxy-pyrazin-2-yl, 6-methoxy-pyrazin-2-yl, 2-methyl-pyrazin-2-yl, 5-methyl-pyrazin-2-yl, 6-methyl-pyrazin-2-yl, 2-fluoro-pyrazin-2-yl, 5-fluoro-pyrazin-2-yl, 6-fluoro-pyrazin-2-yl, 2-chloro-pyrazin-2-yl, 5-chloro-pyrazin-2-yl, 6-chloro-pyrazin-2-yl, 2-trifluoromethyl-pyrazin-2-yl, 5-trifluoromethyl-pyrazin-2-yl, 6-trifluoromethyl-pyrazin-2-yl, 2-cyano-pyrazin-2-yl, 5-cyano-pyrazin-2-yl, 6-cyano-pyrazin-2-yl, pyridazin-3-yl, 4-methoxy-pyridazin-3-yl, 5-methoxy-pyridazin-3-yl, 6-methoxy-pyridazin-3-yl, 4-methyl-pyridazin-3-yl, 5-methyl-pyridazin-3-yl, 6-methyl-pyridazin-3-yl, 4-fluoro-pyridazin-3-yl, 5-fluoro-pyridazin-3-yl, 6-fluoro-pyridazin-3-yl, 4-chloro-pyridazin-3-yl, 5-chloro-pyridazin-3-yl, 6-chloro-pyridazin-3-yl, 4-trifluoromethyl-pyridazin-3-yl, 5-trifluoromethyl-pyridazin-3-yl, 6-trifluoromethyl-pyridazin-3-yl, 4-cyano-pyridazin-3-yl, 5-cyano-pyridazin-3-yl, 6-cyano-pyridazin-3-yl, pyridazin-4-yl, 3-methoxy-pyridazin-4-yl, 5-methoxy-pyridazin-4-yl, 6-methoxy-pyridazin-4-yl, 3-methyl-pyridazin-4-yl, 5-methyl-pyridazin-4-yl, 6-methyl-pyridazin-4-yl, 3-fluoro-pyridazin-4-yl, 5-fluoro-pyridazin-4-yl, 6-fluoro-pyridazin-4-yl, 3-chloro-pyridazin-4-yl, 5-chloro-pyridazin-4-yl, 6-chloro-pyridazin-4-yl, 3-trifluoromethyl-pyridazin-4-yl, 5-trifluoromethyl-pyridazin-4-yl, 6-trifluoromethyl-pyridazin-4-yl, 3-cyano-pyridazin-4-yl, 5-cyano-pyridazin-4-yl, 6-cyano-pyridazin-4-yl, 3,5-dimethyl-isoxazol-4-yl, 3,5-di-(trifluoromethyl)-isoxazol-4-yl, 1H-pyrazol-4-yl, 1-methyl-1H-pyrazol-4-yl, 5-trifluoromethyl-1-methyl-1H-pyrazol-4-yl, 3-trifluoromethyl-1-methyl-1H-pyrazol-4-yl, 1,5-dimethyl-1H-pyrazol-4-yl, 1,3-dimethyl-1H-pyrazol-4-yl, 1,3,5-trimethyl-1H-pyrazol-4-yl, 1H-pyrazol-3-yl, 1-methyl-1H-pyrazol-3-yl, 5-trifluoromethyl-1-methyl-1H-pyrazol-3-yl, 4-trifluoromethyl-1-methyl-1H-pyrazol-3-yl, 1,5-dimethyl-1H-pyrazol-3-yl, 1,4-dimethyl-1H-pyrazol-3-yl and 1,4,5-trimethyl-1H-pyrazol-3-yl.

In another embodiment of the first aspect of the invention, the compound according to general formula (I) is characterized in that
$R^9$ represents H or
$C_{1-6}$-alkyl, branched or unbranched and unsubstituted or substituted with 1, 2, 3, 4 or 5 substituents independently selected from the group consisting of OH, =O, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; or
$C_{3-6}$-cycloalkyl, unsubstituted or substituted with 1, 2, 3, 4 or 5 substituents independently selected from the group consisting of F, Cl, CF$_3$, =O, OCF$_3$; $C_{1-8}$-alkylen-OH, $C_{1-6}$-alkyl, OH, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; wherein said $C_{3-6}$-cycloalkyl residue is optionally connected via a $C_{1-8}$-alkylene group, which in turn may be branched or unbranched and unsubstituted or substituted with 1, 2, 3, 4 or 5 substituents independently selected from the group consisting of F, Cl, CF$_3$, =O, OCF$_3$, OH, O—$C_{1-6}$-alkyl and $C_{1-8}$-alkylen-OH; or
3 to 7 membered heterocyclyl, which is unsubstituted or substituted with 1, 2, 3, 4 or 5 substituents independently selected from the group consisting of F, Cl, CF$_3$, =O, OCF$_3$; $C_{1-8}$-alkylen-OH, $C_{1-6}$-alkyl, OH, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl, wherein said 3 to 7 membered heterocyclyl is optionally connected via a $C_{1-8}$-alkylene group, which in turn may be branched or unbranched and unsubstituted or substituted with 1, 2, 3, 4 or 5 substituents independently selected from the group consisting of F, Cl, CF$_3$, =O, OCF$_3$, OH, O—$C_{1-6}$-alkyl and $C_{1-8}$-alkylen-OH.

More preferably,
$R^9$ represents H or
$C_{1-6}$-alkyl, branched or unbranched and unsubstituted or substituted with 1, 2, 3, 4 or 5 substituents independently selected from the group consisting of OH, =O, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl.

Still more preferably, $R^9$ represents H or $C_{1-6}$-alkyl. Particularly preferred, $R^9$ represents H, methyl, ethyl, isopropyl or n-propyl.

In a preferred embodiment of the first aspect of the present invention, $R^9$ denotes methyl. In another preferred embodiment of the first aspect of the present invention, $R^9$ represents H.

In another embodiment of the first aspect of the invention, the compound according to general formula (I) is characterized in that
$R^{10}$ wherein said $C_{3-10}$-cycloalkyl, 3 to 10 membered heterocyclyl or heteroaryl in each case may be unsubstituted or mono- or poly-substituted and wherein said $C_{3-10}$-cycloalkyl, 3 to 10 membered heterocyclyl or heteroaryl may be in each case connected via a $C_{1-8}$-alkylene group, which in turn may be branched or unbranched and may be unsubstituted or mono- or polysubstituted.

Preferably, $R^{10}$ represents
H or
$C_{1-6}$-alkyl, branched or unbranched and unsubstituted or substituted with 1, 2, 3, 4 or 5 substituents independently selected from the group consisting of F, Cl, $CF_3$, CN, OH, =O, $OCF_3$, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; or $C_{3-6}$-cycloalkyl, unsubstituted or substituted with 1, 2, 3, 4 or 5 substituents independently selected from the group consisting of F, Cl, CN, $CF_3$, =O, $OCF_3$, $C_{1-8}$-alkylen-OH, $C_{1-6}$-alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; wherein said $C_{3-6}$-cycloalkyl is optionally connected via a $C_{1-8}$-alkylene group, which in turn may be branched or unbranched and unsubstituted or substituted with 1, 2, 3, 4 or 5 substituents independently selected from the group consisting of F, Cl, $CF_3$, =O, $OCF_3$, OH, O—$C_{1-6}$-alkyl and $C_{1-8}$-alkylen-OH; or 3 to 7 membered heterocyclyl, which is unsubstituted or substituted with 1, 2, 3, 4 or 5 substituents independently from one another selected from the group consisting of F, Cl, CN, $CF_3$, =O, $OCF_3$, $C_{1-6}$-alkylen-OH, $C_{1-6}$-alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, N(H)—C(=O)—$NH_2$, N(H)—C(=O)—N(H)($C_{1-6}$-alkyl), N(H)—C(=O)—N($C_{1-6}$-alkyl)$_2$, (C=O)$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; wherein said 3 to 7 membered heterocyclyl is optionally connected via a $C_{1-8}$-alkylene group, which in turn may be branched or unbranched and unsubstituted or substituted with 1, 2, 3, 4 or 5 substituents independently selected from the group consisting of F, Cl, $CF_3$, =O, $OCF_3$, OH, O—$C_{1-6}$-alkyl and $C_{1-8}$-alkylen-OH; or heteroaryl, which is unsubstituted or substituted with 1, 2, 3, 4 or 5 substituents selected from the group consisting of F, Cl, CN, $CF_3$, $OCF_3$, $C_{1-8}$-alkylen-OH, $C_{1-6}$-alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl, wherein said heteroaryl residue is optionally connected via a $C_{1-8}$-alkylene group, which in turn may be branched or unbranched and unsubstituted or substituted with 1, 2, 3, 4 or 5 substituents independently from one another selected from the group consisting of F, Cl, $CF_3$, =O, $OCF_3$, OH, O—$C_{1-6}$-alkyl and $C_{1-8}$-alkylen-OH.

In another preferred embodiment of the first aspect of the invention, the compound according to general formula (I) is characterized in that $R^{10}$ represents $C_{3-6}$-cycloalkyl, which is unsubstituted or substituted with 1, 2, 3, 4 or 5 substituents independently from one another selected from the group consisting of F, Cl, $CF_3$, =O, $OCF_3$, OH, O—$C_{1-6}$-alkyl, $C_{1-8}$-alkylen-OH and $C_{1-6}$-alkyl; or 3 to 7 membered heterocyclyl, which contains 1 or 2 heteroatoms or heteroatom groups independently from one another selected from the group consisting of O, S, S(=O), S(=O)$_2$, NH and N—$C_{1-6}$-alkyl, and which is unsubstituted or substituted with 1, 2, 3, 4 or 5 substituents independently from one another selected from the group consisting of F, Cl, $CF_3$, $OCF_3$, CN, $C_{1-6}$-alkyl, $C_{1-8}$-alkylen-OH and O—$C_{1-6}$-alkyl; or heteroaryl, which contains at least one nitrogen atom and which is unsubstituted or substituted with 1, 2 or 3 substituents independently from one another selected from the group consisting of F, Cl, CN, $CF_3$, $OCF_3$, $C_{1-8}$-alkylen-OH, $C_{1-6}$-alkyl, OH, O—$C_{1-6}$-alkyl, S(=O)$_2$—$C_{1-6}$-alkyl, S(=O)$_2$—$NH_2$, $NH_2$, NH($C_{1-6}$-alkyl), N($C_{1-6}$-alkyl)$_2$, O—C(=O)—$NH_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; or a part structure of general formula SF-III

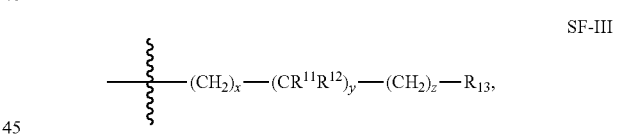

wherein x represents 0, 1 or 2; y represents 0, 1 or 2; z represents 0, 1 or 2;

on the condition that the sum of x, y and z is 1, 2, 3, 4, 5 or 6;

$R^{11}$ and $R^{12}$ are independently from one another selected from H or $C_{1-6}$-alkyl; or $R^{11}$ and $R^{12}$ together with the carbon atom connecting them form a $C_{3-6}$-cycloalkyl or a 3 to 7 membered heterocyclyl, which contains 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloalkyl or 3 to 7 membered heterocyclyl may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;

$R^{13}$ is selected from the group consisting of

H, F, Cl, CN, $CF_3$, $OCF_3$, $C_{1-8}$-alkylen-OH, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$- alkyl, S(=O)$_2$—N(C$_{1-6}$-alkyl)$_2$, NH$_2$, NH(C$_{1-6}$-alkyl), N(C$_{1-6}$-alkyl)$_2$, N(H)—C(=O)—C$_{1-6}$-alkyl, N(C$_{1-6}$-alkyl)-C(=O)—C$_{1-6}$-alkyl, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl, N(H)—C(=O)—NH$_2$, N(H)—C(=O)—N(H)(C$_{1-6}$-alkyl), N(H)—C(=O)—N(C$_{1-6}$-alkyl)$_2$, N(H)—C(=O)—O—C$_{1-6}$-alkyl; O—C(=O)—NH$_2$, O—C(=O)—N(H)(C$_{1-6}$-alkyl), O—C(=O)—N(C$_{1-6}$-alkyl)$_2$; or represents C$_{3-6}$-cycloalkyl, which is unsubstituted or substituted with 1, 2, 3, 4, or 5 substituents independently from one another selected from the group consisting of F, Cl, CF$_3$, =O, OCF$_3$, OH, O—C$_{1-6}$-alkyl, C$_{1-8}$-alkylen-OH and C$_{1-6}$-alkyl; or 3 to 7 membered heterocyclyl, which contains 1 or 2 heteroatoms or heteroatom groups independently from one another selected from the group consisting of O, S, S(=O), S(=O)$_2$, NH and N—C$_{1-6}$-alkyl, and which is unsubstituted or substituted with 1, 2, 3, 4 or 5 substituents independently from one another selected from the group consisting of F, Cl, CF$_3$, OCF$_3$, CN, C$_{1-6}$-alkyl and O—C$_{1-6}$-alkyl; or heteroaryl, which contains at least one nitrogen atom and which is unsubstituted or substituted with 1, 2 or 3 substituents independently from one another selected from the group consisting of F, Cl, CN, CF$_3$, OCF$_3$, C$_{1-8}$-alkylen-OH, C$_{1-6}$-alkyl, OH, O—C$_{1-6}$-alkyl, S(=O)$_2$—C$_{1-6}$-alkyl, S(=O)$_2$—NH$_2$, NH$_2$, NH(C$_{1-6}$-alkyl), N(C$_{1-6}$-alkyl)$_2$, O—C(=O)—NH$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl.

Preferred heteroaryl residues, which contain at least one nitrogen atom, are selected from pyridine, pyrimidine, pyrazine, pyridazine, triazine, quinoline, isoquinoline, phthalazine, naphtheridine, quinoxaline, quinazoline, indole, isoindole, pyrrole, imidazole, pyrazole, 1,2,3-triazole, 1,2,4-triazole, oxazole, isoxazole, thiazole, isothiazole, oxadiazole and thiadiazole.

More preferably, R$^{10}$ represents a part structure of general formula SF-III, wherein R$^{13}$ is selected from the group consisting of H, F, Cl, CN, CF$_3$, OCF$_3$, O—C$_{1-6}$-alkylen-OH, C$_{1-8}$-alkylen-OH, C$_{1-6}$-alkyl, OH, O—C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, N(H)—C(=O)—NH$_2$, N(H)—C(=O)—N(H)(C$_{1-6}$-alkyl), N(H)—C(=O)—N(C$_{1-6}$-alkyl)$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl and N(C$_{1-6}$-alkyl)-C(=O)—C$_{1-6}$-alkyl.

Still more preferably, R$^{10}$ represents a part structure of general formula SF-III, wherein R$^{13}$ is selected from the group consisting of H, OH, F, Cl, CN, S(=O)$_2$—C$_{1-6}$-alkyl, NH$_2$, N(H)—C(=O)—C$_{1-6}$-alkyl, N(H)—S(=O)$_2$—C$_{1-6}$-alkyl, O—C$_{1-6}$-alkyl, C(=O)—NH$_2$, C(=O)—N(H)(C$_{1-6}$-alkyl) and C(=O)—O—C$_{1-6}$-alkyl.

In a preferred embodiment of the invention, the general formula SF-III is selected from formulae SF-IIIa to SF-IIIo

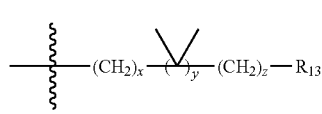
SF-IIIa

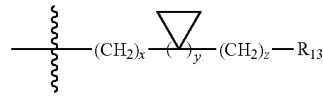
SF-IIIb

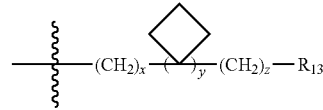
SF-IIIc

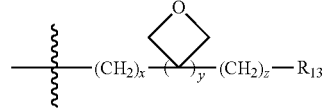
SF-IIId

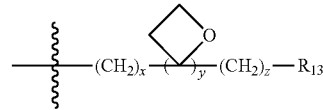
SF-IIIe

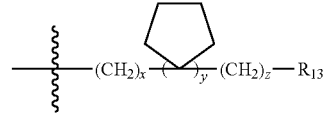
SF-IIIf

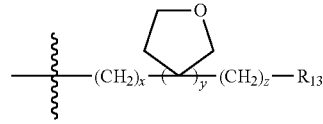
SF-IIIg

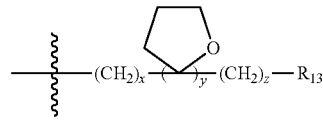
SF-IIIh

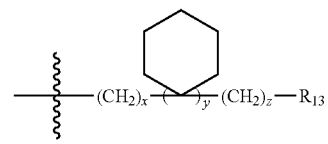
SF-IIIi

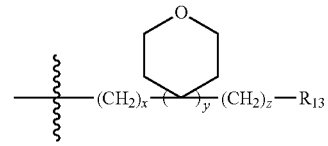
SF-IIIj

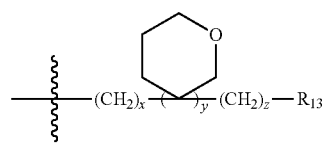
SF-IIIk

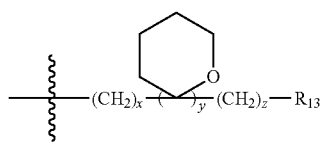
SF-IIIm

SF-IIIn

-continued $$\{\!\!\{-(CH_2)_x-(\overset{CH_2CH_3}{\underset{|}{C}})_y-(CH_2)_z-R_{13},\quad SF\text{-}IIIo$$

wherein x represents 0, 1 or 2; y represents 0 or 1; z represents 0, 1 or 2; on the condition that the sum of x, y and z is 1, 2, 3, 4, 5 or 6.

Preferred are compounds according formula (I), that are characterized that $R^{10}$ is represented by any part structure the general formulae SF-IIIa to SF-IIIo, wherein x represents 1, y represents 0 and z represents 0.

Also preferred are compounds according formula (I), that are characterized that $R^{10}$ is represented by any part structure the general formulae SF-IIIa to SF-IIIo, wherein x represents 1, y represents 1 and z represents 0.

Also preferred are compounds according formula (I), that are characterized that $R^{10}$ is represented by any part structure the general formulae SF-IIIa to SF-IIIo, wherein x represents 0, y represents 1 and z represents 0.

Also preferred are compounds according formula (I), that are characterized that $R^{10}$ is represented by any part structure the general formulae SF-IIIa to SF-IIIo, wherein x represents 0, y represents 1 and z represents 1.

In a particularly preferred embodiment of the first aspect of the invention, the compound according to general formula (I) is characterized in that $R^{10}$ is selected from the group consisting of methyl, ethyl, 2-propyl (iso-propyl), 1-propyl (n-propyl), 1-butyl, 2-butyl, 2-methyl-propyl, 1,1-dimethyl-ethyl (tert-butyl), 1-pentyl, 2-pentyl, 3-pentyl, 2-methyl-butyl, 2,2-dimethyl-propyl (neo-pentyl), 1-hexyl, 2-hexyl, 3-hexyl, 3,3-dimethyl-butyl, cyclopropyl, cyclopropylmethyl, 2-cyclopropyl-ethyl, 1-cyclopropyl-ethyl as well as -continued

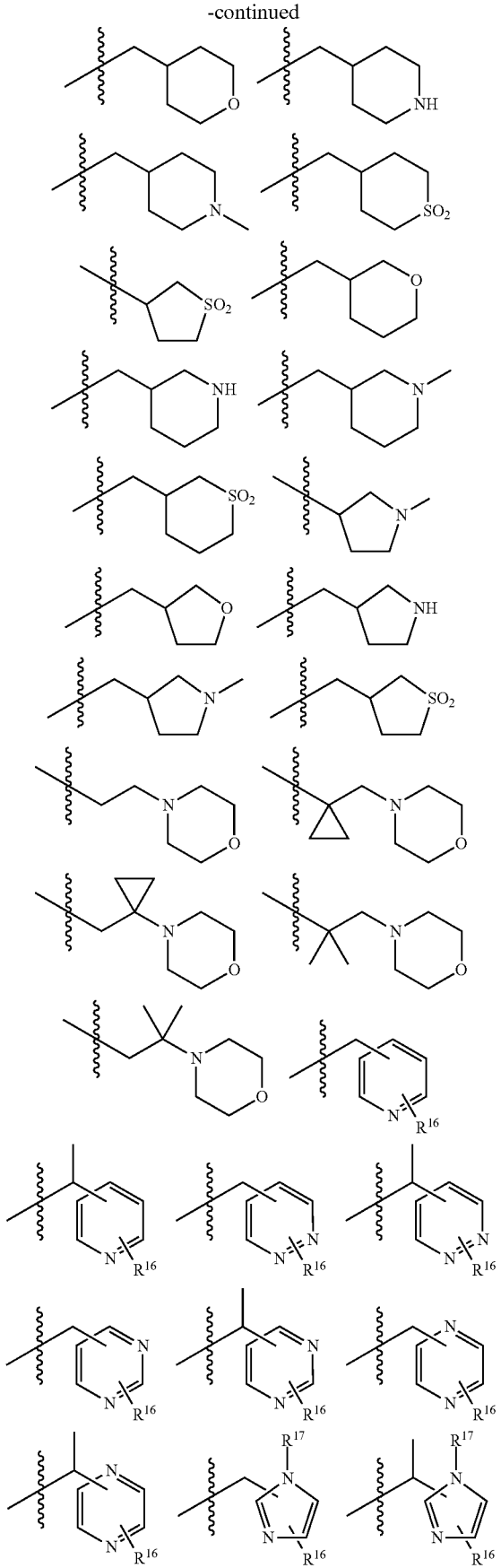
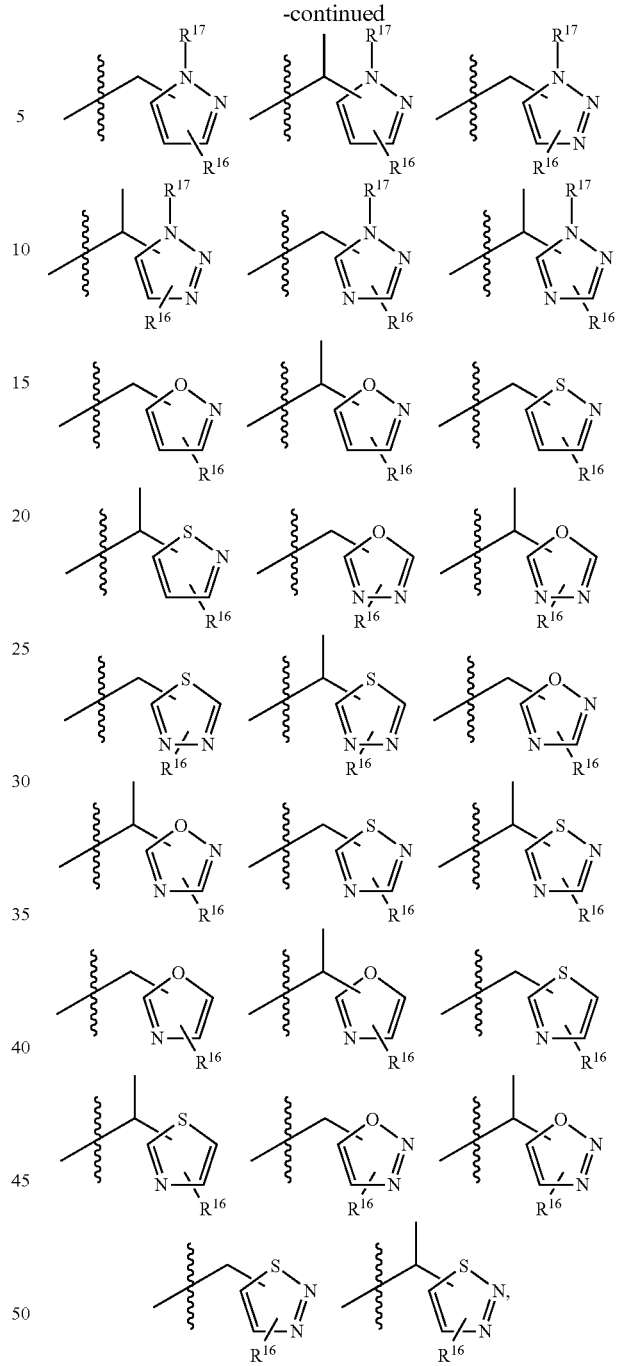

wherein
$R^{16}$ represents 1, 2 or 3 substituents, selected from $C_{1-6}$-alkyl, $CF_3$, F, Cl, CN, OH, $OCF_3$, O—$C_{1-6}$-alkyl, $NH_2$, $N(H)C_{1-6}$-alkyl, $N(C_{1-6}$-alkyl$)_2$, 1-pyrrolidinyl, 1-piperidinyl, 4-methyl-piperidin-1-yl or 1-morpholinyl,
and $R^{17}$ represents H or $C_{1-6}$-alkyl.

In a particularly preferred embodiment, $R^9$ represents H or $C_{1-6}$-alkyl and
$R^{10}$ represents
$C_{3-6}$-cycloalkyl, which is unsubstituted or substituted with 1, 2, 3, 4 or 5 substituents independently from one another selected from the group consisting of F, Cl, $CF_3$, =O, $OCF_3$, OH, O—$C_{1-6}$-alkyl, $C_{1-8}$-alkylen-OH and $C_{1-6}$-alkyl; or 3 to 7 membered heterocylyl, which contains 1 or 2 heteroatoms or heteroatom groups independently from one another selected from the group consisting of O, S, S(=O), S(=O)$_2$, NH and N—C$_{1-6}$-alkyl, and which is unsubstituted or substituted with 1, 2, 3, 4 or 5 substituents independently from one another selected from the group consisting of F, Cl, CF$_3$, OCF$_3$, ON, C$_{1-6}$-alkyl, C$_{1-8}$-alkylen-OH and O—C$_{1-6}$-alkyl; or heteroaryl, which contains at least one nitrogen atom and which is unsubstituted or substituted with 1, 2 or 3 substituents independently from one another selected from the group consisting of F, Cl, CN, CF$_3$, OCF$_3$, C$_{1-8}$-alkylen-OH, C$_{1-6}$-alkyl, OH, O—C$_{1-6}$-alkyl, S(=O)$_2$—C$_{1-6}$-alkyl, S(=O)$_2$—NH$_2$, NH$_2$, NH(C$_{1-6}$-alkyl), N(C$_{1-6}$-alkyl)$_2$, O—C(=O)—NH$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; or a part structure of general formula SF-III

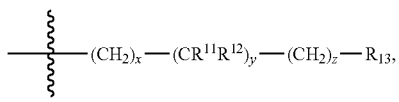

SF-III wherein
x represents 0, 1 or 2; y represents 0, 1 or 2; z represents 0, 1 or 2; on the condition that the sum of x, y and z is 1, 2, 3, 4, 5 or 6;
$R^{11}$ and $R^{12}$ are independently from one another selected from H or C$_{1-6}$-alkyl; or
$R^{11}$ and $R^{12}$ together with the carbon atom connecting them form a C$_{3-6}$-cycloalkyl or a 3 to 7 membered heterocyclyl, which contains 1 or 2 heteroatoms or heteroatom groups independently from one another selected from the group consisting of O, S, S(=O), S(=O)$_2$, NH and N—C$_{1-6}$-alkyl, wherein said C$_{3-6}$-cycloalkyl or 3 to 7 membered heterocyclyl may be unsubstituted or substituted with 1, 2, 3, 4 or 5 substituents independently from one another selected from the group consisting of F, Cl, CF$_3$, OCF$_3$, CN, C$_{1-6}$-alkyl and O—C$_{1-6}$-alkyl;
$R^{13}$ is selected from the group consisting of
H, F, Cl, CN, CF$_3$, OCF$_3$, C$_{1-8}$-alkylen-OH, C$_{1-6}$-alkyl, OH, O—C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, N(H)—C(=O)—NH$_2$, N(H)—C(=O)—N(H)(C$_{1-6}$-alkyl), N(H)—C(=O)—N(C$_{1-6}$-alkyl)$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl and N(C$_{1-6}$-alkyl)-C(=O)—C$_{1-6}$-alkyl,
or represents
C$_{3-6}$-cycloalkyl, which is unsubstituted or substituted with 1, 2, 3, 4, or 5 substituents independently from one another selected from the group consisting of F, Cl, CF$_3$, =O, OCF$_3$, OH, O—C$_{1-6}$-alkyl, C$_{1-8}$-alkylen-OH and C$_{1-6}$-alkyl; or
3 to 7 membered heterocyclyl, which contains 1 or 2 heteroatoms or heteroatom groups independently from one another selected from the group consisting of O, S, S(=O), S(=O)$_2$, NH and N—C$_{1-6}$-alkyl, and which is unsubstituted or substituted with 1, 2, 3, 4 or 5 substituents independently from one another selected from the group consisting of F, Cl, CF$_3$, OCF$_3$, CN, C$_{1-6}$-alkyl and O—C$_{1-6}$-alkyl; or heteroaryl, which contains at least one nitrogen atom and which is unsubstituted or substituted with 1, 2 or 3 substituents independently from one another selected from the group consisting of F, Cl, CN, CF$_3$, OCF$_3$, C$_{1-8}$-alkylen-OH, C$_{1-6}$-alkyl, OH, O—C$_{1-6}$-alkyl, S(=O)$_2$—C$_{1-6}$-alkyl, S(=O)$_2$—NH$_2$, NH$_2$, NH(C$_{1-6}$-alkyl), N(C$_{1-6}$-alkyl)$_2$, O—C(=O)—NH$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl.

In another embodiment of the first aspect of the invention, the compound according to general formula (I) is characterized in that $R^9$ and $R^{10}$ together with the nitrogen atom connecting them form a 3 to 7 membered heterocyclyl, unsubstituted or substituted with 1, 2, 3, 4 or 5 substituents selected from the group consisting of F, Cl, CN, CF$_3$, =O, OH, C$_{1-6}$-alkyl, O—C$_{1-6}$-alkyl, C$_{1-6}$-alkylen-OH, OCF$_3$, SO$_2$(C$_{1-6}$-alkyl), SO$_2$NH$_2$, SO$_2$N(H)C$_{1-6}$-alkyl, SO$_2$N(C$_{1-6}$-alkyl)$_2$, C$_{1-6}$-alkylen-SO$_2$(C$_{1-6}$-alkyl), NH$_2$, NH(C$_{1-6}$-alkyl), N(C$_{1-6}$-alkyl)$_2$, (C=O)C$_{1-6}$-alkyl, C$_{3-6}$-cycloalkyl or 3 to 7 membered heterocyclyl, in each case unsubstituted or mono- or polysubstituted.

Preferably, $R^9$ and $R^{10}$ together with the nitrogen atom connecting them form a heterocyclyl selected from the group consisting of

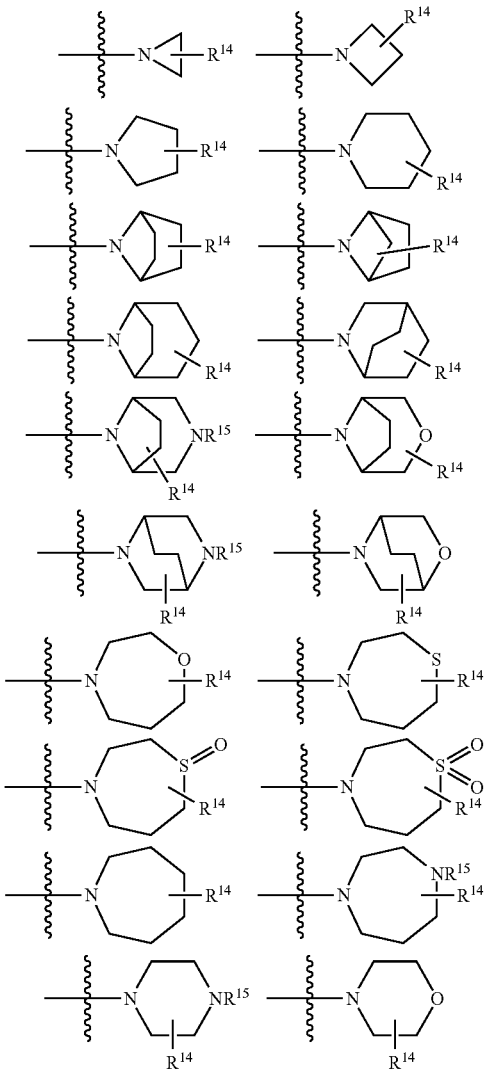

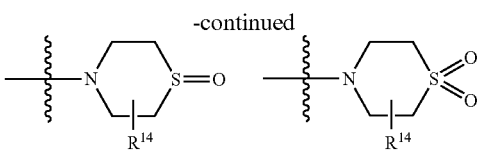

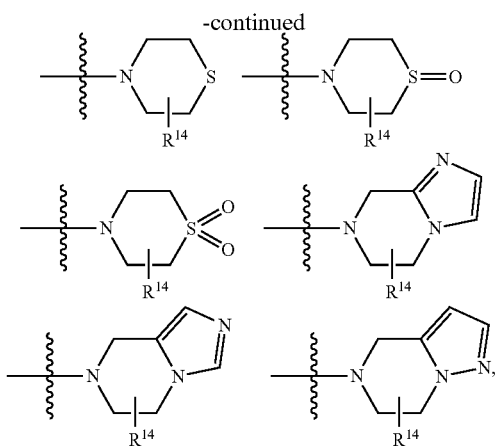

wherein
$R^{14}$ denotes 0, 1, 2, 3 or 4 substituents which are in each case independently of each other selected from the group consisting of F, Cl, $CF_3$, =O, $OCF_3$, OH, O—$C_{1-6}$-alkyl, $C_{1-8}$-alkylen-OH, $SO_2(C_{1-6}$-alkyl), $C_{1-8}$-alkylen-$SO_2(C_{1-6}$-alkyl), and $C_{1-6}$-alkyl; or
$R^{14}$ denotes at least two substituents, wherein two substituents $R^{14}$ stand together for a $C_{1-8}$-alkylen-group, substituted or unsubstituted, wherein optionally one or more C-atoms of the $C_{1-8}$-alkylen-group is replaced by a heteroatom or heteroatom group, selected of O, N—$R^{15}$, S, S(O) and $S(O)_2$, and wherein these two substituents $R^{14}$ are positioned at different carbon atoms of the heterocyclyl residue, so the $C_{1-8}$-alkylen-group represents a bridge to form a bicyclic heterocyclyl residue; or
$R^{14}$ denotes at least two substituents, wherein two substituents $R^{14}$ stand together for a $C_{2-6}$-alkylen-group, substituted or unsubstituted, wherein optionally one or more C-atoms of the $C_{2-6}$-alkylen-group is replaced by a heteroatom or heteroatom group, selected from O, N—$R^{15}$, S, S(O) and $S(O)_2$, and wherein these two substituents $R^{14}$ are positioned at the same carbon atom of the heterocyclyl residue, so the $C_{2-6}$-alkylen-group forms a spiro-heterocyclyl residue; and
$R^{15}$ represents H, $C_{1-6}$-alkyl or (C=O)$C_{1-6}$-alkyl.

More preferably,
$R^9$ and $R^{10}$ together with the nitrogen atom connecting them form a heterocycloaliphatic residue selected from the group consisting of

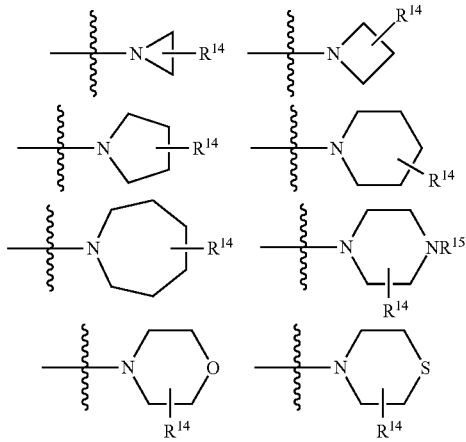

wherein
$R^{14}$ denotes 0, 1, 2, 3 or 4 substituents which are in each case independently of each other selected from the group consisting of F, Cl, $CF_3$, =O, $OCF_3$, OH, O—$C_{1-6}$-alkyl, $C_{1-6}$-alkylen-OH, $C_{1-6}$-alkylen-$SO_2(C_{1-6}$-alkyl), $SO_2(C_{1-6}$-alkyl) and $C_{1-6}$-alkyl;
or
$R^{14}$ denotes at least two substituents, wherein two substituents $R^{14}$ stand together for a $C_{1-6}$-alkylen-group, substituted or unsubstituted, wherein optionally one or more C-atoms of the $C_{1-6}$-alkylen-group is replaced by a heteroatom or heteroatom group, selected of O, N—$R^{15}$, S, S(O) and $S(O)_2$, and wherein these two substituents $R^{14}$ are positioned at different carbon atoms of the heterocyclyl, so the $C_{1-6}$-alkylen-group represents a bridge to form a bicyclic heterocyclyl;
or
$R^{14}$ denotes at least two substituents, wherein two substituents $R^{14}$ stand together for a $C_{2-6}$-alkylen-group, substituted or unsubstituted, wherein optionally one or more C-atoms of the $C_{2-6}$-alkylen-group is replaced by a heteroatom or heteroatom group, selected of O, N—$R^{15}$, S, S(O) and $S(O)_2$, and wherein these two substituents $R^{14}$ are positioned at the same carbon atom of the heterocyclyl, so the $C_{2-6}$-alkylen-group forms a spiro-heterocyclyl; and
$R^{15}$ represents H, $C_{1-6}$-alkyl or (C=O)$C_{1-6}$-alkyl.

Most preferred,
$R^9$ and $R^{10}$ together with the nitrogen atom connecting them form a heterocycloaliphatic residue selected from the group consisting of

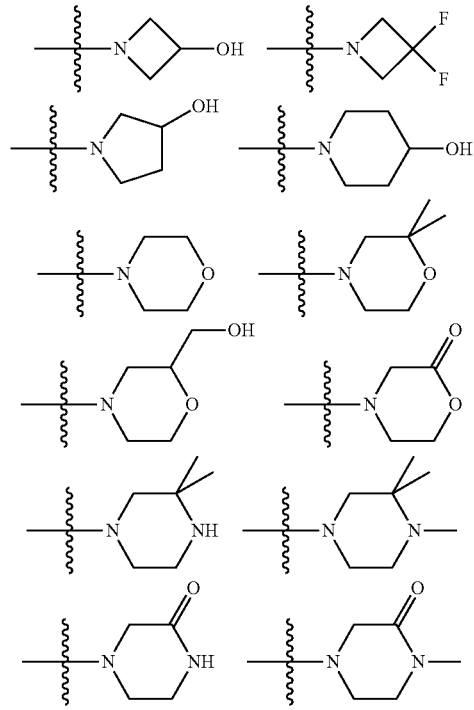

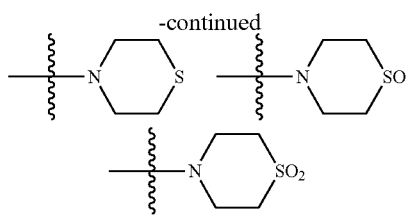

In another embodiment of the first aspect of the invention, the compound according to general formula (I) is characterized in that
the compound of general formula (I) is a compound according to general formula (Ia) or (Ib),

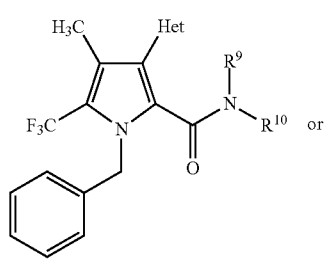

(Ia)

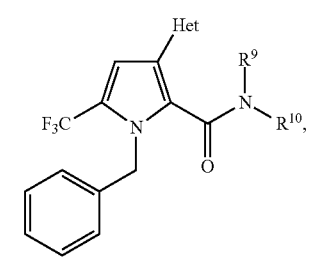

(Ib)

wherein
Het is select from group consisting of pyrrol, thienyl, pyrazolyl, imidazolyl, isoxazolyl, oxazolyl, thiazolyl, pyridinyl, pyrazinyl, pyrimidinyl and pyridazinyl, each substituted by zero or one or two substituents of the group consisting of $R^6$ and $R^7$,
wherein $R^6$ and $R^7$ are each independently of one another selected from the group consisting of F; Cl; CN; $C_{1-6}$-alkyl; $CF_3$; $CF_2H$; $CFH_2$; OH; $OCF_3$; $OCF_2H$; $OCFH_2$; O—$C_{1-6}$-alkyl; S(=O)—$C_{1-6}$-alkyl; S(=O)$_2$—$C_{1-6}$-alkyl; cyclopropyl or O-cyclopropyl;
$R^9$ represents H or $C_{1-6}$-alkyl; and
$R^{10}$ represents
$C_{3-6}$-cycloalkyl, which is unsubstituted or substituted with 1, 2 or 3 substituents independently from one another selected from the group consisting of F, Cl, $CF_3$, =O, $OCF_3$, OH, O—$C_{1-6}$-alkyl, $C_{1-6}$-alkylen-OH and $C_{1-6}$-alkyl;
or
represents a part structure of general formula SF-III

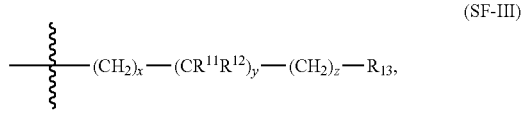

(SF-III)

wherein
x represents 0, 1 or 2; y represents 0, 1 or 2; z represents 0, 1 or 2; on the condition that the sum of x, y and z is 1, 2, 3, 4, 5 or 6;
$R^{11}$ and $R^{12}$ are independently from one another selected from H or $C_{1-6}$-alkyl;
$R^{13}$ is selected from the group consisting of
H, F, Cl, CN, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—C(=O)—$C_{1-6}$-alkyl, N($C_{1-6}$-alkyl)-C(=O)—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$;
or
$R^9$ and $R^{10}$ together with the nitrogen atom connecting them form a heterocyclyl, selected from the group consisting of

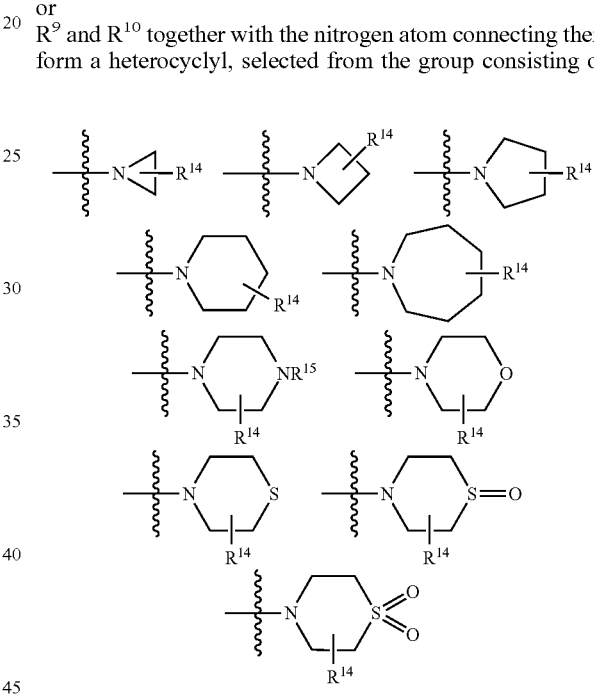

wherein
$R^{14}$ denotes 0, 1 or 2 substituents which are in each case independently of each other selected from the group consisting of F, Cl, $CF_3$, =O, $OCF_3$, OH, O—$C_{1-6}$-alkyl, $C_{1-6}$-alkylen-OH, $C_{1-6}$-alkylen-$SO_2$($C_{1-6}$-alkyl), $SO_2$($C_{1-6}$-alkyl) and $C_{1-6}$-alkyl;
and
$R^{15}$ represents H, $C_{1-6}$-alkyl or (C=O)$C_{1-6}$-alkyl.

In another preferred embodiment of the first aspect of the invention, the compound according to general formula (I) is characterized in that
the compound of general formula (I) is a compound according to general formula (Ia) or (Ib),
wherein
Het is select from group consisting of pyrrol, thienyl, pyrazolyl, imidazolyl, isoxazolyl, oxazolyl, thiazolyl, pyridinyl, pyrazinyl, pyrimidinyl and pyridazinyl, each substituted by zero or one or two substituents of the group consisting of $R^6$ and $R^7$,
wherein $R^6$ and $R^7$ are each independently of one another selected from the group consisting of F; Cl; CN; $C_{1-6}$-alkyl;

CF₃; CF₂H; CFH₂; OH; OCF₃; OCF₂H; OCFH₂; O—C₁₋₆-alkyl; S(=O)—C₁₋₆-alkyl; S(=O)₂—C₁₋₆-alkyl; cyclopropyl or O-cyclopropyl;

R⁹ represents H or methyl; and

R¹⁰ represents ethyl, 2-propyl (iso-propyl), 1-propyl (n-propyl), 1-butyl, 2-butyl, 2-methyl-propyl, 1,1-dimethyl-ethyl (tert-butyl), 1-pentyl, 2-pentyl, 3-pentyl, 2-methyl-butyl, 2,2-dimethyl-propyl (neo-pentyl), 1-hexyl, 2-hexyl, 3-hexyl, 3,3-dimethyl-butyl, cyclopropyl, cyclopropylmethyl, 2-cyclopropyl-ethyl, 1-cyclopropyl-ethyl as well as

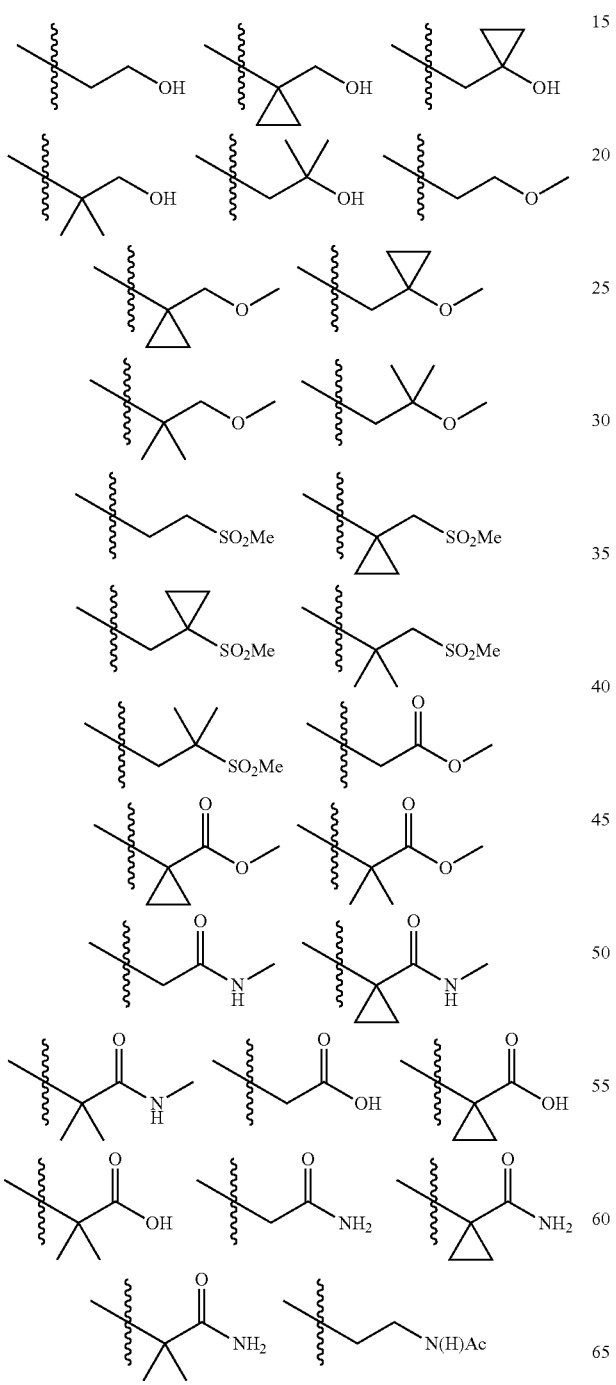

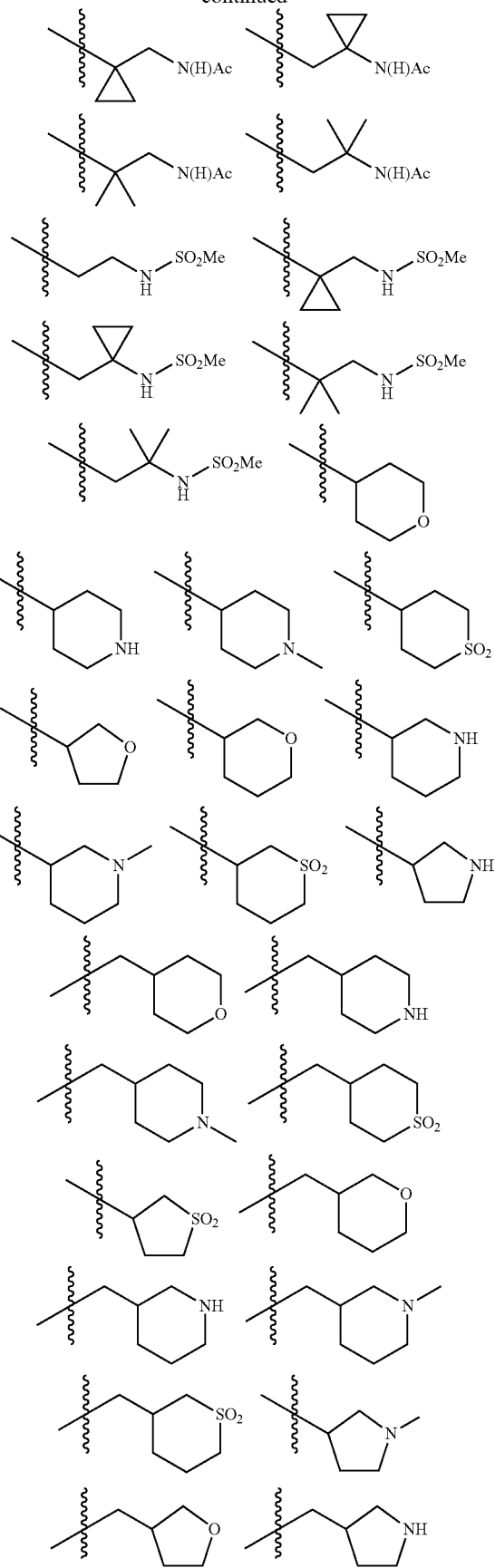

-continued

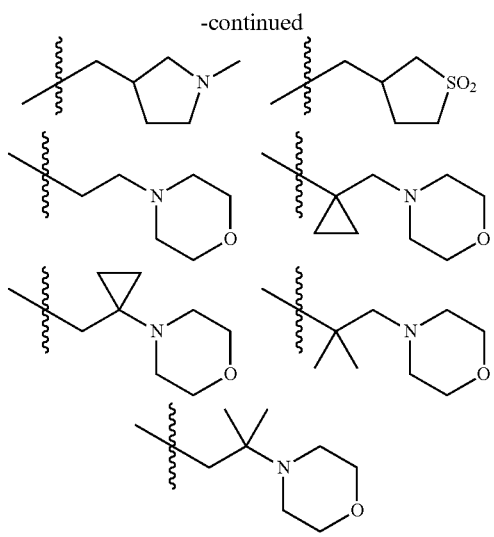

or
R⁹ and R¹⁰ together with the nitrogen atom connecting them form a heterocyclyl, selected from the group consisting of

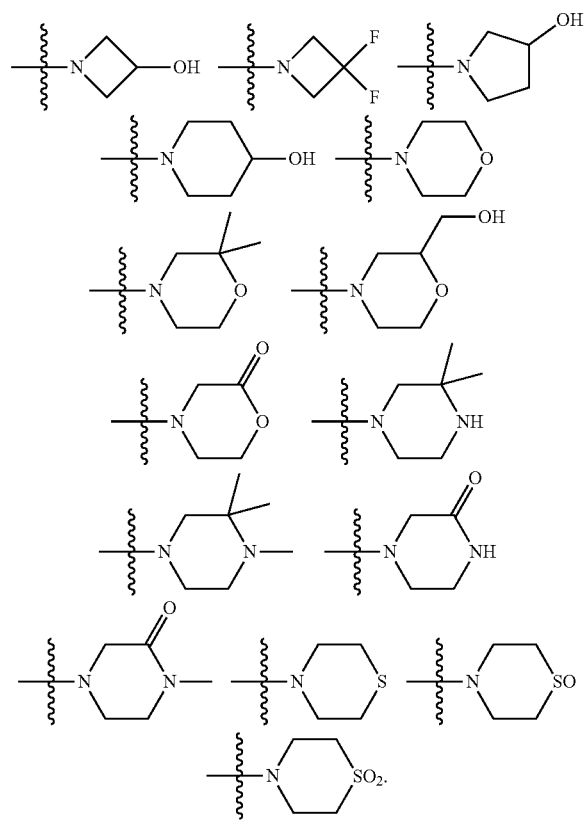

In another preferred embodiment of the first aspect of the invention, the compound according to general formula (I) is characterized in that
the compound of general formula (I) is a compound according to general formula (Ia) or (Ib),
wherein Het is select from group consisting of
pyridin-2-yl, pyridin-3-yl, pyridin-4-yl, pyrazin-2-yl, pyrimidin-2-yl, pyrimidin-4-yl, pyrimidin-5-yl, pyridazin-3-yl, pyridazin-4-yl, thiophen-2-yl, thiophen-3-yl, pyrazol-3-yl, pyrazol-4-yl, pyrazol-5-yl,
isoxazol-3-yl, isoxazol-4-yl, isoxazol-5-yl, oxazol-2-yl, oxazol-4-yl, oxazol-5-yl, thiazol-2-yl, thiazol-4-yl, thiazol-5-yl, each substituted by zero or one or two substituents of the group consisting of R⁶ and R⁷, wherein R⁶ and R⁷ are each independently of one another selected from the group consisting of F; Cl; CN; CF₃; CH₃; OH; OCF₃ and OCH₃.

R⁹ represents H or methyl; and

R¹⁰ represents ethyl, 2-propyl (iso-propyl), 1-propyl (n-propyl), 1-butyl, 2-butyl, 2-methyl-propyl, 1,1-dimethyl-ethyl (tert-butyl), 1-pentyl, 2-pentyl, 3-pentyl, 2-methyl-butyl, 2,2-dimethyl-propyl (neo-pentyl), 1-hexyl, 2-hexyl, 3-hexyl, 3,3-dimethyl-butyl, cyclopropyl, cyclopropylmethyl, 2-cyclopropyl-ethyl, 1-cyclopropyl-ethyl as well as

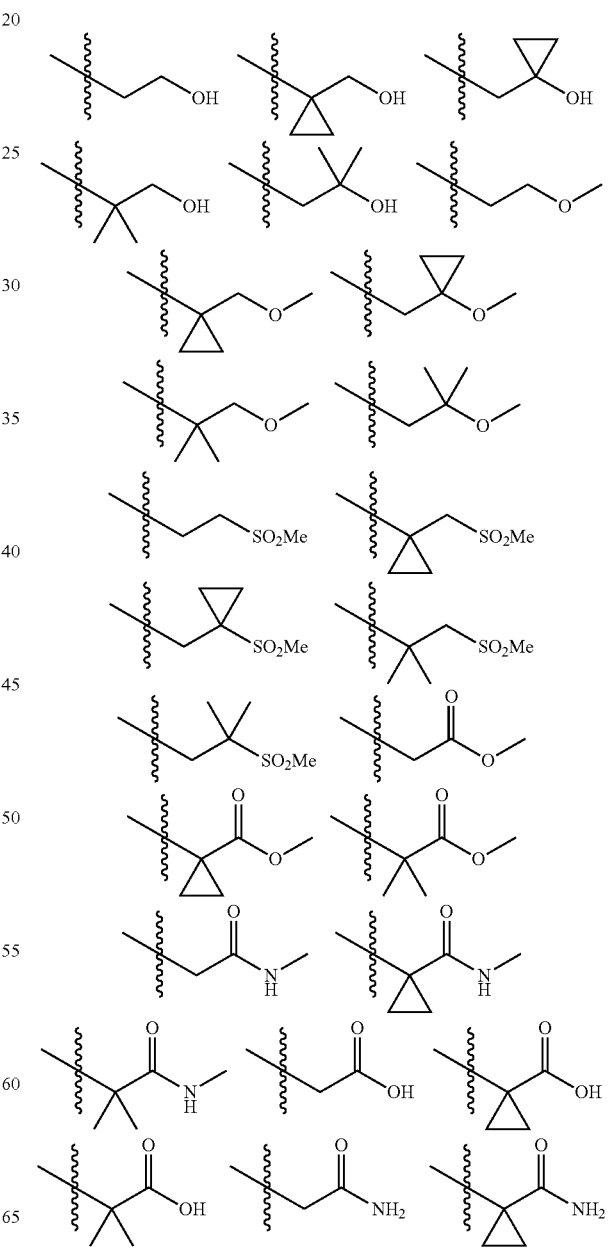

-continued

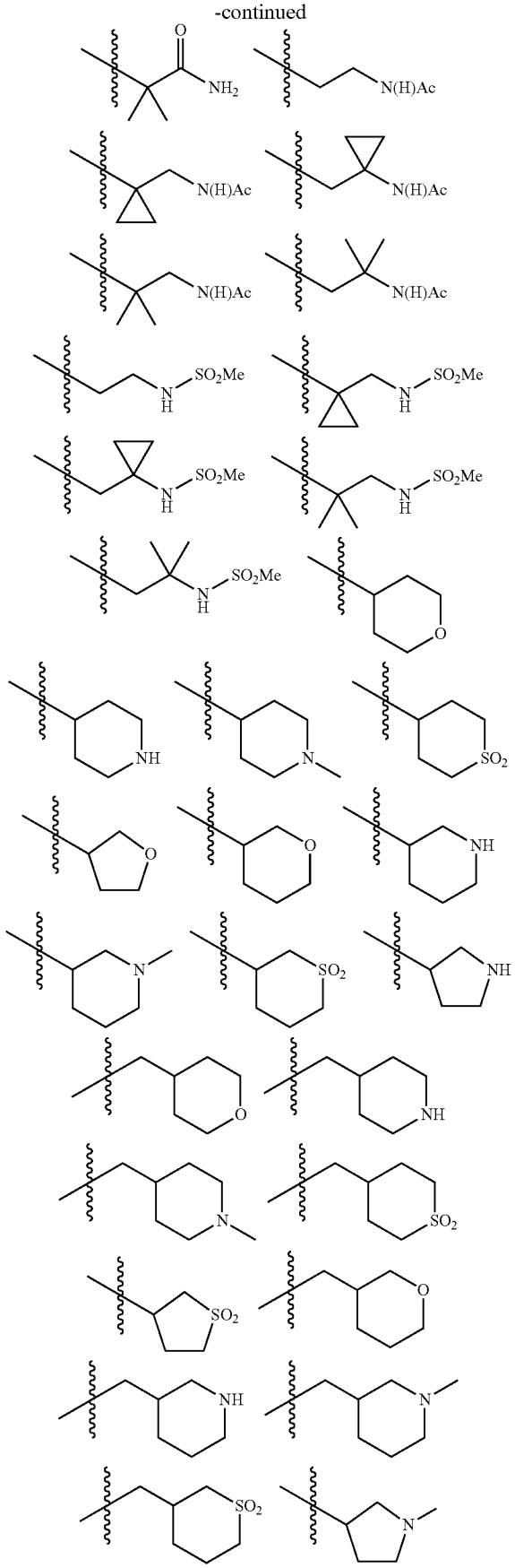

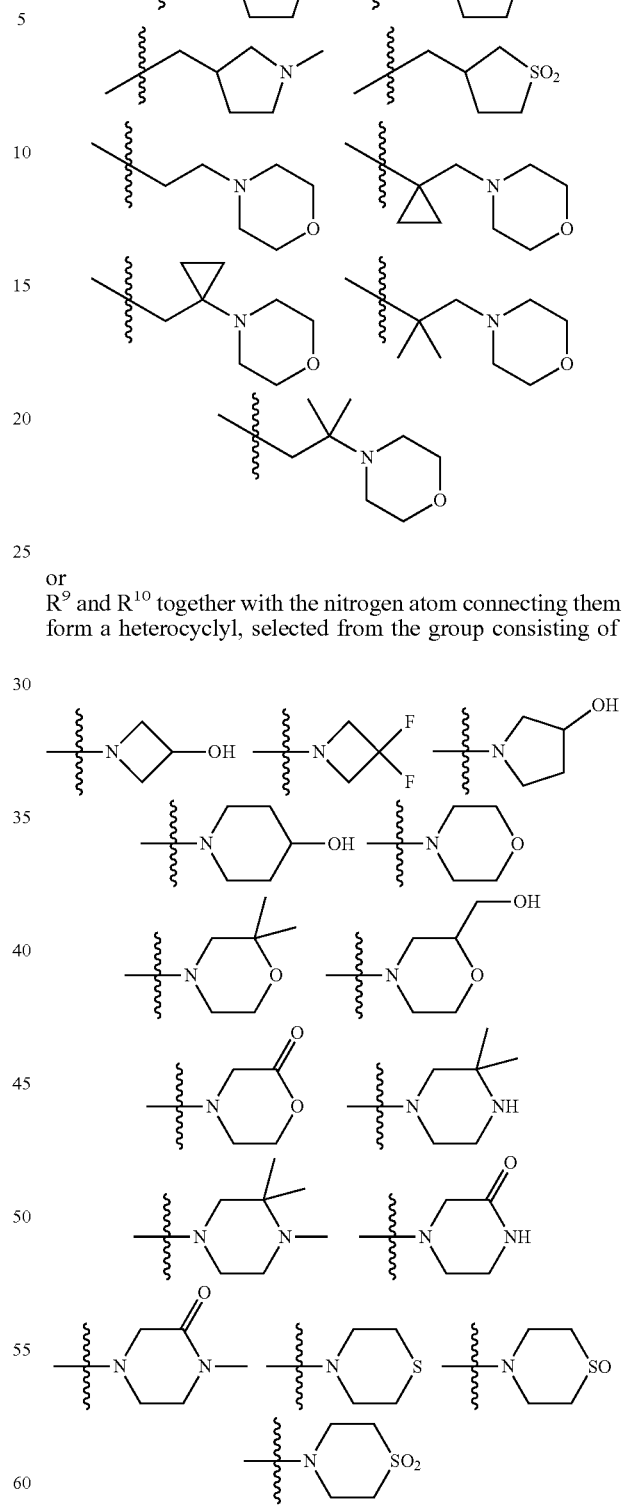

or
$R^9$ and $R^{10}$ together with the nitrogen atom connecting them form a heterocyclyl, selected from the group consisting of Particularly preferred compounds according to the invention are selected from the group consisting of
01  1-Benzyl-N-(2,2-dimethyl-propyl)-3-[3-fluoro-5-(trifluoromethyl)-pyridin-2-yl]-N,4-dimethyl-5-(trifluoromethyl)-1H-pyrrole-2-carboxylic acid amide 02 [1-Benzyl-3-[3-fluoro-5-(trifluoromethyl)-pyridin-2-yl]-4-methyl-5-(trifluoromethyl)-1H-pyrrol-2-yl]-morpholin-4-yl-methanone
03 1-Benzyl-3-(3,5-dimethyl-isoxazol-4-yl)-N-(2,2-dimethyl-propyl)-N,4-dimethyl-5-(trifluoromethyl)-1H-pyrrole-2-carboxylic acid amide
04 [1-Benzyl-3-(3,5-dimethyl-isoxazol-4-yl)-4-methyl-5-(trifluoromethyl)-1H-pyrrol-2-yl]-morpholin-4-yl-methanone
05 1-Benzyl-3-(6-cyano-4-methyl-pyridin-3-yl)-N-(2,2-dimethyl-propyl)-N,4-dimethyl-5-(trifluoromethyl)-1H-pyrrole-2-carboxylic acid amide
06 5-[1-Benzyl-4-methyl-2-(morpholine-4-carbonyl)-5-(trifluoromethyl)-1H-pyrrol-3-yl]-4-methyl-pyridine-2-carbonitrile
07 1-Benzyl-3-(6-chloro-4-methyl-pyridin-3-yl)-N-(2,2-dimethyl-propyl)-N,4-dimethyl-5-(trifluoromethyl)-1H-pyrrole-2-carboxylic acid amide
08 [1-Benzyl-3-(6-chloro-4-methyl-pyridin-3-yl)-4-methyl-5-(trifluoromethyl)-1H-pyrrol-2-yl]-morpholin-4-yl-methanone
09 1-Benzyl-N-(2,2-dimethyl-propyl)-3-(6-methoxy-4-methyl-pyridin-3-yl)-N,4-dimethyl-5-(trifluoromethyl)-1H-pyrrole-2-carboxylic acid amide
10 [1-Benzyl-3-(6-methoxy-4-methyl-pyridin-3-yl)-4-methyl-5-(trifluoromethyl)-1H-pyrrol-2-yl]-morpholin-4-yl-methanone
11 1-Benzyl-N-(2,2-dimethyl-propyl)-N,4-dimethyl-3-pyrazin-2-yl-5-(trifluoromethyl)-1H-pyrrole-2-carboxylic acid amide
12 [1-Benzyl-4-methyl-3-pyrazin-2-yl-5-(trifluoromethyl)-1H-pyrrol-2-yl]-morpholin-4-yl-methanone
13 1-Benzyl-N-(2,2-dimethyl-propyl)-N,4-dimethyl-3-pyridazin-4-yl-5-(trifluoromethyl)-1H-pyrrole-2-carboxylic acid amide
14 [1-Benzyl-4-methyl-3-pyridazin-4-yl-5-(trifluoromethyl)-1H-pyrrol-2-yl]-morpholin-4-yl-methanone
15 1-Benzyl-N-(2,2-dimethyl-propyl)-3-(5-fluoro-pyridin-2-yl)-N,4-dimethyl-5-(trifluoromethyl)-1H-pyrrole-2-carboxylic acid amide
16 [1-Benzyl-3-(5-fluoro-pyridin-2-yl)-4-methyl-5-(trifluoromethyl)-1H-pyrrol-2-yl]-morpholin-4-yl-methanone
17 1-Benzyl-3-(5-chloro-pyrimidin-2-yl)-N-(2,2-dimethyl-propyl)-N,4-dimethyl-5-(trifluoromethyl)-1H-pyrrole-2-carboxylic acid amide
18 [1-Benzyl-3-(5-chloro-pyrimidin-2-yl)-4-methyl-5-(trifluoromethyl)-1H-pyrrol-2-yl]-morpholin-4-yl-methanone
19 1-Benzyl-N-(2,2-dimethyl-propyl)-3-(5-fluoro-pyrimidin-2-yl)-N,4-dimethyl-5-(trifluoromethyl)-1H-pyrrole-2-carboxylic acid amide
20 [1-Benzyl-3-(5-fluoro-pyrimidin-2-yl)-4-methyl-5-(trifluoromethyl)-1H-pyrrol-2-yl]-morpholin-4-yl-methanone
21 1-Benzyl-N-(2,2-dimethyl-propyl)-3-(5-methoxy-pyrimidin-2-yl)-N,4-dimethyl-5-(trifluoromethyl)-1H-pyrrole-2-carboxylic acid amide
22 1-Benzyl-N-(2,2-dimethyl-propyl)-N,4-dimethyl-3-pyrimidin-2-yl-5-(trifluoromethyl)-1H-pyrrole-2-carboxylic acid amide
23 [1-Benzyl-4-methyl-3-pyrimidin-2-yl-5-(trifluoromethyl)-1H-pyrrol-2-yl]-morpholin-4-yl-methanone
24 1-Benzyl-3-(6-chloro-pyridazin-3-yl)-N-(2,2-dimethyl-propyl)-N,4-dimethyl-5-(trifluoromethyl)-1H-pyrrole-2-carboxylic acid amide
25 [1-Benzyl-3-(6-chloro-pyridazin-3-yl)-4-methyl-5-(trifluoromethyl)-1H-pyrrol-2-yl]-morpholin-4-yl-methanone
26 [1-Benzyl-4-methyl-3-(1H-pyrazol-4-yl)-5-(trifluoromethyl)-1H-pyrrol-2-yl]-morpholin-4-yl-methanone
27 [1-Benzyl-4-methyl-3-(1-methyl-1H-pyrazol-4-yl)-5-(trifluoromethyl)-1H-pyrrol-2-yl]-morpholin-4-yl-methanone
28 1-Benzyl-3-(5-chloro-pyridin-2-yl)-N-(2,2-di methyl-propyl)-N,4-dimethyl-5-(trifluoromethyl)-1H-pyrrole-2-carboxylic acid amide
29 1-Benzyl-3-(5-chloro-pyridin-2-yl)-N,4-dimethyl-N-(2-methylsulfonyl-ethyl)-5-(trifluoromethyl)-1H-pyrrole-2-carboxylic acid amide
30 [1-Benzyl-3-(5-chloro-pyridin-2-yl)-4-methyl-5-(trifluoromethyl)-1H-pyrrol-2-yl]-morpholin-4-yl-methanone
31 1-Benzyl-3-(5-chloro-pyrimidin-2-yl)-N-(2-cyano-2-methyl-propyl)-N,4-dimethyl-5-(trifluoromethyl)-1H-pyrrole-2-carboxylic acid amide
32 1-Benzyl-N-(2-carbamoyl-2-methyl-propyl)-3-(5-chloro-pyrimidin-2-yl)-N,4-dimethyl-5-(trifluoromethyl)-1H-pyrrole-2-carboxylic acid amide
33 4-[1-Benzyl-3-(5-chloro-pyrimidin-2-yl)-4-methyl-5-(trifluoromethyl)-1H-pyrrole-2-carbonyl]-piperazin-2-one
34 [1-Benzyl-3-(5-chloro-pyrimidin-2-yl)-4-methyl-5-(trifluoromethyl)-1H-pyrrol-2-yl]-(2,2-dimethyl-morpholin-4-yl)-methanone
35 [1-Benzyl-3-(5-chloro-pyrimidin-2-yl)-4-methyl-5-(trifluoromethyl)-1H-pyrrol-2-yl]-(1,1-dioxo-[1,4]thiazinan-4-yl)-methanone
36 1-Benzyl-3-(5-chloro-pyrimidin-2-yl)-N-cyclopropyl-4-methyl-5-(trifluoromethyl)-1H-pyrrole-2-carboxylic acid amide
37 1-Benzyl-N-(2,2-dimethyl-propyl)-3-(2-methoxy-pyrimidin-5-yl)-N,4-dimethyl-5-(trifluoromethyl)-1H-pyrrole-2-carboxylic acid amide
38 [1-Benzyl-3-(2-methoxy-pyrimidin-5-yl)-4-methyl-5-(trifluoromethyl)-1H-pyrrol-2-yl]-morpholin-4-yl-methanone
39 1-Benzyl-N-(2,2-dimethyl-propyl)-N,4-dimethyl-3-pyrimidin-5-yl-5-(trifluoromethyl)-1H-pyrrole-2-carboxylic acid amide
40 [1-Benzyl-4-methyl-3-pyrimidin-5-yl-5-(trifluoromethyl)-1H-pyrrol-2-yl]-morpholin-4-yl-methanone
41 1-Benzyl-3-(5-chloro-thiophen-2-yl)-N-(2,2-dimethyl-propyl)-N,4-dimethyl-5-(trifluoromethyl)-1H-pyrrole-2-carboxylic acid amide
42 1-Benzyl-N-(2,2-dimethyl-propyl)-N,4-dimethyl-3-(1H-pyrazol-4-yl)-5-(trifluoromethyl)-1H-pyrrole-2-carboxylic acid amide
43 1-Benzyl-N-(2,2-dimethyl-propyl)-3-(6-hydroxy-pyridin-3-yl)-N,4-dimethyl-5-(trifluoromethyl)-1H-pyrrole-2-carboxylic acid amide
44 [1-Benzyl-3-(6-hydroxy-pyridin-3-yl)-4-methyl-5-(trifluoromethyl)-1H-pyrrol-2-yl]-morpholin-4-yl-methanone
45 1-Benzyl-N-(2,2-dimethyl-propyl)-3-(6-methoxy-pyridin-3-yl)-N,4-dimethyl-5-(trifluoromethyl)-1H-pyrrole-2-carboxylic acid amide
46 [1-Benzyl-3-(6-methoxy-pyridin-3-yl)-4-methyl-5-(trifluoromethyl)-1H-pyrrol-2-yl]-morpholin-4-yl-methanone
47 1-Benzyl-N-(2,2-dimethyl-propyl)-3-(5-methoxy-pyrazin-2-yl)-N,4-dimethyl-5-(trifluoromethyl)-1H-pyrrole-2-carboxylic acid amide
48 [1-Benzyl-3-(5-methoxy-pyrazin-2-yl)-4-methyl-5-(trifluoromethyl)-1H-pyrrol-2-yl]-morpholin-4-yl-methanone
49 1-Benzyl-N-(2,2-dimethyl-propyl)-N,4-dimethyl-3-(1-methyl-1H-pyrazol-4-yl)-5-(trifluoromethyl)-1H-pyrrole-2-carboxylic acid amide
50 1-Benzyl-3-(5-chloro-pyridin-2-yl)-N-isopropyl-N,4-dimethyl-5-(trifluoromethyl)-1H-pyrrole-2-carboxylic acid amide 51 1-Benzyl-N-isopropyl-N,4-dimethyl-3-(1-methyl-1H-pyrazol-3-yl)-5-(trifluoromethyl)-1H-pyrrole-2-carboxylic acid amide
52 1-Benzyl-3-(5-chloro-pyrimidin-2-yl)-N-isopropyl-4-methyl-5-(trifluoromethyl)-1H-pyrrole-2-carboxylic acid amide
53 1-Benzyl-3-(5-chloro-pyridin-2-yl)-N-isopropyl-4-methyl-5-(trifluoromethyl)-1H-pyrrole-2-carboxylic acid amide
54 1-Benzyl-3-(5-chloro-pyrimidin-2-yl)-N-isopropyl-N,4-dimethyl-5-(trifluoromethyl)-1H-pyrrole-2-carboxylic acid amide
55 1-Benzyl-3-(5-cyclopropyl-pyrazin-2-yl)-N-isopropyl-N,4-dimethyl-5-(trifluoromethyl)-1H-pyrrole-2-carboxylic acid amide
56 1-Benzyl-3-(5-cyclopropyl-pyrimidin-2-yl)-N-isopropyl-N,4-dimethyl-5-(trifluoromethyl)-1H-pyrrole-2-carboxylic acid amide
57 1-Benzyl-3-(5-chloro-pyrimidin-2-yl)-N,4-dimethyl-N-[2-methyl-2-(methylcarbamoyl)-propyl]-5-(trifluoromethyl)-1H-pyrrole-2-carboxylic acid amide
58 1-Benzyl-3-(5-chloro-pyrimidin-2-yl)-N-[2-(dimethylcarbamoyl)-2-methyl-propyl]-N,4-dimethyl-5-(trifluoromethyl)-1H-pyrrole-2-carboxylic acid amide
59 1-Benzyl-N-isopropyl-N,4-dimethyl-3-(1-methyl-1H-imidazol-2-yl)-5-(trifluoromethyl)-1H-pyrrole-2-carboxamide
60 1-Benzyl-N-isopropyl-N,4-dimethyl-3-[5-(methylsulfinyl)-pyridin-2-yl]-5-(trifluoromethyl)-1H-pyrrole-2-carboxylic acid amide
61 1-Benzyl-3-[5-chloro-3-(methylsulfinyl)-pyridin-2-yl]-N-isopropyl-N,4-dimethyl-5-(trifluoromethyl)-1H-pyrrole-2-carboxylic acid amide
optionally in the form of a single stereoisomer or a mixture of stereoisomers, in the form of the free compound and/or a physiologically acceptable salt or solvate thereof.

Furthermore, preference may be given to compounds according to the invention that cause at least a 50% inhibition, which is present at a concentration of 3 µM, in a fluorescent assay for CaV2.2 channels with HEK293 cells in which human CaV2.2 channels were stably expressed at a concentration of less 3 µM, preferably less than 1000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR 3, Molecular Devices, Sunnyvale, USA), as described hereinafter.

The compounds according to the invention and corresponding stereoisomers and also the respective corresponding acids, bases, salts and solvates are suitable for the treatment and/or prophylaxis of one or more disorders and/or diseases selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

The present invention further relates to a compound according to the present invention for CaV2.2 calcium channel regulation, preferably for use in CaV2.2 calcium channel blockage.

The present invention therefore further relates to a compound according to the present invention for the prophylaxis and/or treatment of disorders and/or diseases which are mediated, at least in part, at least in part, by CaV2.2 channels.

The term "disorders and/or diseases which are mediated, at least in part, by CaV2.2 channels", is intended to include each of or all of the disease states.

The substances according to the invention hence act, for example, on CaV2.2 channels relevant in connection with various diseases, so that they are suitable as a pharmacologically active compound in pharmaceutical compositions.

The compounds according to the first aspect of the present invention and the corresponding stereoisomers and the respective salts and solvates are toxicologically safe and are therefore suitable as pharmacologically active ingredients in pharmaceutical compositions.

In another aspect of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art, such as are described for example in "Remington's Pharmaceutical Sciences", A. R. Gennaro (Editor), 17$^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

CaV2.2 channels are believed to be involved in a variety of diseases or disorders in mammals such as humans. These include pain (e.g.; acute pain, chronic pain, visceral pain, headache pain, inflammatory pain, mixed pain), stroke (the neuronal damage resulting from head trauma), epilepsy, mood disorders, schizophrenia, neurodegenerative disorders.

Another embodiment of the present invention is at least one compound according the present invention for the treatment and/or prophylaxis of one or more disorders selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

Another embodiment of the present invention is at least one compound according to the present invention for the treatment and/or prophylaxis of pain, in particular acute pain and/or chronic pain and/or visceral pain and/or headache pain and/or inflammatory pain and/or mixed pain.

Acute pain according to the invention might include nociceptive pain and post-operative or surgical pain. Chronic pain according to the invention might include peripheral neuropathic pain such as post-herpetic neuralgia, traumatic nerve injury, nerve compression or entrapment, small fibre neuropathy, diabetic neuropathy, neuropathic cancer pain, failed back surgery Syndrome, trigeminal neuralgia, phantom limb pain; neuroma pain, complex regional pain syndrome, chronic arthritic pain and related neuralgias, and pain associated with cancer, chemotherapy, HIV and HIV treatment-induced neuropathy; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome. In treating osteoarthritic pain, joint mobility will also improve as the underlying chronic pain is reduced. Thus, at least one compound for treatment of osteoarthritic pain inherently will also improve joint mobility in patients suffering from osteoarthritis. Visceral pain according to the invention might include interstitial cystitis, irritable bowel syndrome, Crohn's disease and chronic pelvic pain syndrome. Inflammatory pain according to the invention might include rheumatoid arthritis and endometriosis. Headache pain according to the invention might include migraine, cluster headache, tension headache syndrome, facial pain and headache caused by other diseases. Mixed pain according to the invention might include lower back pain, neck and shoulder pain, burning mouth syndrome and complex regional pain syndrome.

In another embodiment of the invention, at least one compound according to the present invention is particularly suitable for the treatment and/or prophylaxis of mood disorders.

Mood disorders according to the invention might include anxiety disorder, social anxiety disorder, panic disorder, specific phobias, for example, specific animal phobias, social phobias, obsessive-compulsive disorder, agoraphobia, post-traumatic stress syndrome, addiction (including dependence, withdrawal and/or relapse of medication, including opioids, but also drugs such as cocaine, opioids, alcohol and nicotine), generalised anxiety disorders, single episodic or recurrent major depressive disorders and dysthymic disorders, or bipolar disorders, for example, bipolar I disorder, bipolar II disorder and cyclothymic disorder.

In another embodiment of the invention, at least one compound according to the present invention is particularly suitable for the treatment and/or prophylaxis of epilepsy.

Epilepsy according to the invention might include partial seizures such as temporal lobe epilepsy, absence seizures generalized seizures, and tonic/clonic seizures.

In yet another embodiment of the invention, at least one compound according to the present invention is particularly suitable for the treatment and/or prophylaxis of neurodegenerative disorders.

Neurodegenerative disorders according to the invention might include Parkinson's disease, Alzheimer's disease, multiple sclerosis, neuropathies, Huntington's disease, presbycusis and amyotrophic lateral sclerosis (ALS).

Particularly preferably, at least one compound according to the present invention is suitable for the treatment and/or prophylaxis of one or more disorders and/or diseases selected from the group consisting of pain, preferably of pain selected from the group consisting of acute pain, chronic pain, visceral pain, headache pain, inflammatory pain and mixed pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Most particularly preferably, at least one compound according to the present invention according to the invention is suitable for the treatment and/or prophylaxis of pain, preferably of pain selected from the group consisting of acute pain, chronic pain, visceral pain, headache pain, inflammatory pain and mixed pain.

The present invention further relates to a compound according to the present invention and one or more additional pharmaceutically active agents for use in the prophylaxis and/or treatment of disorders and/or diseases which are mediated, at least in part, at least in part, by CaV2.2 channels.

In particular, the present invention therefore further relates to a compound according to the present invention and one or more additional pharmaceutically active agents for the prophylaxis and/or treatment of disorders and/or diseases selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

Most particularly preferred is a compound according to the present invention one or more additional pharmaceutically active agents for the prophylaxis and/or treatment of pain, preferably of pain selected from the group consisting of acute pain, chronic pain, visceral pain, headache pain, inflammatory pain and mixed pain.

Additional pharmaceutically active agents in the treatment of pain may include, for example, i) opiate agonists or antagonists, ii) calcium channel antagonists, iii) 5HT receptor agonists or antagonists, iv) sodium channel antagonists, v) NMDA receptor agonists or antagonists, vi) COX-2 selective inhibitors, vii) NKI antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, xiv) neurontin (gabapentin), xv) pregabalin.

Additional pharmaceutically active agents in the treatment of depression or anxiety can include other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), adrenoreceptor antagonists, atypical anti-depressants, benzodiazepines, 5-HT1 A agonists or antagonists, especially 5-HT1 A partial agonists, neurokinin 1 receptor antagonists, corticotropin releasing factor (CRF) antagonists, and pharmaceutically acceptable salts thereof.

Another embodiment of the present invention therefore relates to use of at least one compound according to the present invention for the preparation of a pharmaceutical composition for the treatment and/or prophylaxis of one or more disorders or diseases, particularly selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders.

Another aspect of the present invention is a method of treatment and/or prophylaxis of disorders and/or diseases in a mammal, preferably of disorders and/or diseases selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders, which comprises administering an effective amount of at least one compound according to the present invention to the mammal.

Another embodiment of the present invention is a method for CaV2.2 calcium channel regulation, preferably for use in CaV2.2 calcium channel blockage, and, further, a method of treatment and/or prophylaxis of disorders and/or diseases, which are mediated, at least in part, by CaV2.2 channels, in a mammal, preferably of disorders and/or diseases selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders, which comprises administering an effective amount of at least one compound according to the present invention to the mammal.

All preferred embodiments of the first aspect of the invention are preferred vice versa for the other aspects and embodiments.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour und Smith (J. Pharm. Exp. Ther. 72, 74 79 (1941)) or by the formalin test (e.g. according to D. Dubuisson et al., Pain 1977, 4, 161-174).

Examples

The compounds according to the invention can be prepared in the manner described below. The following examples further illustrate the invention but are not to be construed as limiting its scope.

All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The stationary phase used for the column chromatography was silica gel 60 (0.04-0.063 mm) from E. Merck, Darmstadt. The reactions were, if necessary, carried out under an inert atmosphere (mostly nitrogen).

The yields of the compounds prepared are not optimized. The mixing ratios of solvents are usually stated in the volume/volume ratio. The reactions were, if necessary, carried out under an inert atmosphere (mostly $N_2$). The number of equivalents of reagents and the amounts of solvents employed as well as the reaction temperatures and times can vary slightly between different reactions carried out by the same (general) method. The work-up and purification methods were adapted according to the characteristic properties of each compound and can vary slightly for analogous/general methods.

All the intermediate products and exemplary compounds were analytically characterized by means of $^1$H-NMR spectroscopy. In addition, mass spectrometry tests (MS, m/z for [M+H]$^+$) were carried out for all the exemplary compounds and selected intermediate products.

The following abbreviations are used in the descriptions of the experiments: MeCN=acetonitrile; NBS=N-Bromosuccinimide; EtOAc=ethylacetate; THF=tetrahydrofuran; MeOH=methanol; EtOH=ethanol; HATU=(1-[bis(dimethylamino)methylene]-1H-1,2,3-triazolo[4,5-b]pyridinium 3-oxid hexafluoro-phosphate); DIPEA=N,N-diisopropylethylamine; n-BuLi=n-butyllithium; dppf=1,1'; bis(diphenylphosphanyl)ferrocene; HBPin=4,4,5,5-tetramethyl-1,3,2-dioxaborolane; DMF=N,N-dimethylformamid;

DMSO=dimethylsulfoxid; h=hour; min=minute; tert=tertiary; RT=room temperature; DCM=dichloromethane; TMSCl=trimethylsilyl chloride; dba=dibenzylideneacetone; Boc=tert-butyloxycarbonyl; BOP-Cl=bis(2-oxo-3-oxazolidinyl)phosphinic chloride; CDI=carbonyldiimidazole; DME=1,2-di-methoxyethane; EDCl=N-(3-dimethylaminopropyl)-N'-ethylcarbodiimide hydrochloride; HOAt=1-hydroxy-7-azabenzotriazole; XPhos=2-dicyclohexyl-phosphino-2',4',6'-triisopropylbiphenyl; TLC=thin layer chromatography; CC=column chromatography.

Section (A)

General Synthetic Route 1:

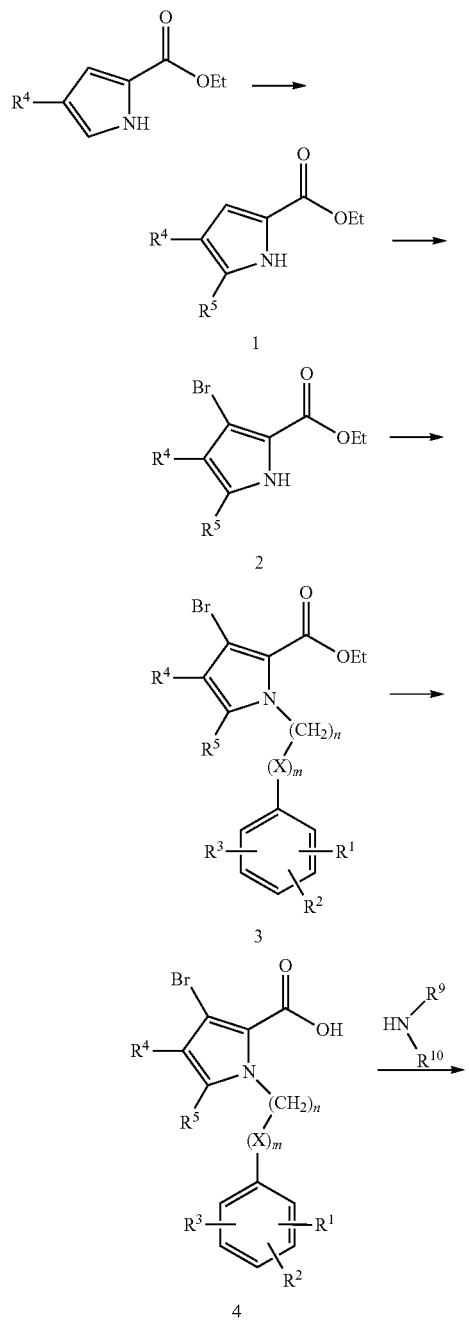

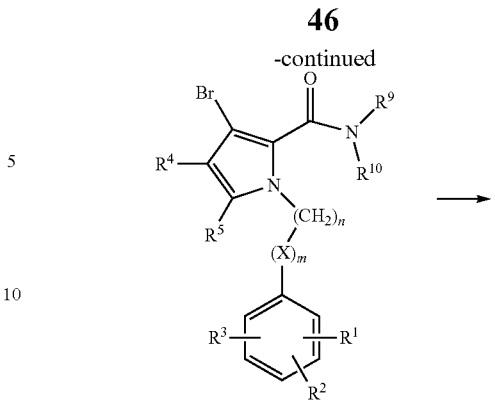

EXAMPLES

Example 01

1-benzyl-3-(5-methoxypyrazin-2-yl)-N,4-dimethyl-N-neopentyl-5-(trifluoromethyl)-1H-pyrrole-2-carboxamide 1a): Ethyl 4-methyl-5-(trifluoromethyl)-1H-pyrrole-2-carboxylate Trifluoromethanesulfonyl chloride (15.4 ml, 137.2 mmol, 1.05 eq) was added to the Ar degassed solution of ethyl-4-methyl-1H-pyrrole-2-carboxylate (20 g, 130.7 mmol, 1 eq), $K_2HPO_4$ (68.2 g, 392.1 mmol, 3 eq), dichlorotris (1, 10-phenanthroline) ruthenium (II) hydrate (1.8 g, 2.6 mmol, 0.02 eq) in acetonitrile (200 ml). The reaction mixture was stirred for 6 d at RT adjacent to a fluorescent light bulb (23 W). The reaction mixture was diluted with EtOAc and $H_2O$. The aqueous layer was extracted with EtOAc (300 ml×2). Combined organic layers were dried over anhydrous $Na_2SO_4$, filtered, concentrated under reduced pressure to give crude product which was then purified by CC to yield ethyl 4-methyl-5-(trifluoromethyl)-1H-pyrrole-2-carboxylate (11.5 g, 40%) as a white solid.

1b): Ethyl 3-bromo-4-methyl-5-(trifluoromethyl)-1H-pyrrole-2-carboxylate

NBS (7.2 g, 40.7 mmol, 1 eq) was portion wise added to an ice cooled solution of ethyl 4-methyl-5-(trifluoromethyl)-1H-pyrrole-2-carboxylate (9 g, 40.7 mmol, 1 eq) and $K_2CO_3$ (5.9 g, 42.7 mmol, 1.05 eq) in MeCN (90 ml). The reaction mixture was stirred for 2 h at RT. The reaction mixture was diluted with EtOAc and H$_2$O. The aqueous layer was extracted with EtOAc (100 ml×2). Combined organic layers were dried over anhydrous Na$_2$SO$_4$, filtered, concentrated under reduced pressure to give 12.5 g of ethyl 3-bromo-4-methyl-5-(trifluoromethyl)-1H-pyrrole-2-carboxylate which was directly used in the next step without further purification.

1c): Ethyl 1-benzyl-3-bromo-4-methyl-5-(trifluoromethyl)-1H-pyrrole-2-carboxylate Benzyl bromide (6.5 ml, 55.0 mmol, 1.1 eq) was added to the solution of ethyl 3-bromo-4-methyl-5-(trifluoromethyl)-1H-pyrrole-2-carboxylate (15 g, 50.0 mmol, 1 eq) and K$_2$CO$_3$ (13.8 g, 100.0 mmol, 2 eq) in MeCN (150 ml). The reaction mixture was stirred for 13 h at 80° C. Then the reaction mixture was cooled to RT and diluted with EtOAc and H$_2$O. The aqueous layer was extracted with EtOAc (150 ml×2). Combined organic layers were dried over anhydrous Na$_2$SO$_4$, concentrated under reduced pressure to give crude mass which was then purified by column chromatography to yield ethyl 1-benzyl-3-bromo-4-methyl-5-(trifluoromethyl)-1H-pyrrole-2-carboxylate (18 g, 92%) as a pale yellow color oil.

1d): 1-Benzyl-3-bromo-4-methyl-5-(trifluoromethyl)-1H-pyrrole-2-carboxylic acid Lithium hydroxide monohydrate (5.3 g, 128.6 mmol, 5 eq) was added to the ice cold solution of ethyl 1-benzyl-3-bromo-4-methyl-5-(trifluoromethyl)-1H-pyrrole-2-carboxylate (10 g, 25.6 mmol, 1 eq) in THF (100 ml), MeOH (20 ml) and H$_2$O (50 ml). The mixture was allowed to warm up to RT and then heated up to 100° C. for 14 h, cooled to RT and then diluted with H$_2$O and acidified with 6N HCl (pH~2). The aqueous layer was extracted with EtOAc (100 ml×2). Combined organic layers were dried over anhydrous Na$_2$SO$_4$, filtered, concentrated under reduced pressure to give crude mass which was triturated with diethyl ether to afford 1-benzyl-3-bromo-4-methyl-5-(trifluoromethyl)-1H-pyrrole-2-carboxylic acid (7.7 g, 83%) as a white color solid.

1e): 1-Benzyl-3-bromo-4-methyl-N-neopentyl-5-(trifluoromethyl)-1H-pyrrole-2-carboxamide HATU (6.2 g, 16.5 mmol, 1.2 eq) and DIPEA (6.1 ml, 34.5 mmol, 2.5 eq) were added to the ice cold solution of 1-benzyl-3-bromo-4-methyl-N-neopentyl-5-(trifluoromethyl)-1H-pyrrole-2-carboxamide (5 g, 13.8, 1 eq) in DMF (50 ml) and it was stirred for 10 min at same temperature. Then 2,2-dimethylpropan-1-amine (1.4 g, 16.5 mmol, 1.2 eq) was added and the reaction mixture was warmed to RT and then stirred for 15 h. The reaction mixture was diluted with EtOAc and H$_2$O. The aqueous layer was extracted with EtOAc (80 ml×2). Combined organic layers were dried over anhydrous Na$_2$SO$_4$, filtered, concentrated under reduced pressure to give crude 1-benzyl-3-bromo-4-methyl-N-neopentyl-5-(trifluoromethyl)-1H-pyrrole-2-carboxamide (5.1 g, 86%) as a white color solid which was directly used in next step without further purification.

1f): 1-Benzyl-3-bromo-N,4-dimethyl-N-neopentyl-5-(trifluoromethyl)-1H-pyrrole-2-carboxamide Methyl iodide (1.4 ml, 23.2 mmol, 2 eq) was added to the ice cold solution of 1-benzyl-3-bromo-4-methyl-N-neopentyl-5-(trifluoromethyl)-1H-pyrrole-2-carboxamide (5 g, 11.6 mmol, 1 eq), NaH (0.5 g, 23.2 mmol, 2 eq) in THF (50 ml) and stirred for 2 h at RT. The reaction mass was poured onto crushed ice and extracted with EtOAc (75 ml×2). Combined organic layers were dried over anhydrous Na$_2$SO$_4$, filtered and concentrated under reduced pressure to give crude mass which was then purified by CC to afford 1-benzyl-3-bromo-N,4-dimethyl-N-neopentyl-5-(trifluoromethyl)-1H-pyrrole-2-carboxamide (4.5 g, 87%) as a white solid.

1g): 1-Benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide 2.4 M n-BuLi (2.2 ml, 5.3 mmol, 1.2 eq) was added to the cooled (−78° C.) solution of 1-benzyl-3-bromo-N,4-dimethyl-N-neopentyl-5-(trifluoromethyl)-1H-pyrrole-2-carboxamide (2 g, 4.4 mmol, 1 eq) in dry THF (40 ml) and it was stirred at same temperature for 30 min. HBPin (3.5 ml, 22.4 mmol, 5 eq) was added to the reaction mixture and stirred for 45 min at −78° C. The reaction mass was quenched with saturated NH$_4$Cl solution and extracted with EtOAc (50 ml×2). Combined organic layers were dried over anhydrous Na$_2$SO$_4$, filtered, concentrated under reduced pressure to yield crude mass which was then purified by CC to afford 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (1 g, 46%) as a white solid.

1h): 1-Benzyl-3-(5-methoxypyrazin-2-yl)-N,4-dimethyl-N-neopentyl-5-(trifluoromethyl)-1H-pyrrole-2-carboxamide To a solution of 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.2 g, 0.40 mmol, 1 eq.) in DMF (10 ml) was added 2M Na$_2$CO$_3$ (0.6 ml) solution and 2-bromo-5-methoxypyrazine (0.09 g, 0.48 mmol, 1.2 eq). The solution was degassed with argon for 5 min followed by addition of Pd(dppf)Cl$_2$.CH$_2$Cl$_2$ (0.02 g, 0.028 mmol, 0.07 eq.) The reaction mixture is refluxed at 110° C. for 16 h. The reaction mass was poured onto crushed ice, extracted with EtOAc (50 ml×2). Combined organic layers were dried over anhydrous Na$_2$SO$_4$, filtered, concentrated under reduced pressure to yield crude mass which was then purified by CC to afford 1-benzyl-3-(5-methoxypyrazin-2-yl)-N,4-dimethyl-N-neopentyl-5-(trifluoromethyl)-1H-pyrrole-2-carboxamide (0.12 g, 62%) as a white solid.

Example 02

1-Benzyl-3-(6-methoxypyridin-3-yl)-N,4-dimethyl-N-neopentyl-5-(trifluoromethyl)-1H-pyrrole-2-carboxamide To a solution of 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.6 g, 1.21 mmol, 1 eq) in DMF (15 ml) was added 2M Na$_2$CO$_3$ (1.8 ml, 3.65 mmol, 3 eq) solution and 5-bromo-2-methoxypyridine (0.19 ml, 1.46 mmol, 1.2 eq). The solution was degassed with Ar for 5 min followed by addition of Pd(dppf)Cl$_2$.CH$_2$Cl$_2$ (0.069 g, 0.082 mmol, 0.07 eq.) The reaction mixture was stirred at 110° C. for 16 h. The reaction mass was poured onto crushed ice, extracted with EtOAc (75 ml×2). Combined organic layer were dried over anhydrous Na$_2$SO$_4$, filtered, concentrated under reduced pressure to yield crude mass which was then purified by CC to afford 1-benzyl-3-(6-methoxypyridin-3-yl)-N,4-dimethyl-N-neopentyl-5-(trifluoromethyl)-1H-pyrrole-2-carboxamide (0.31 g, 54%) as a white solid.

Example 03

1-Benzyl-3-(6-hydroxypyridin-3-yl)-N,4-dimethyl-N-neopentyl-5-(trifluoromethyl)-1H-pyrrole-2-carboxamide TMSCl (0.27 ml, 2.11 mmol, 4 eq) was added to a solution of 1-benzyl-3-(6-methoxypyridin-3-yl)-N,4-dimethyl-N-neopentyl-5-(trifluoromethyl)-1H-pyrrole-2-carboxamide (0.25 g, 0.52 mmol, 1 eq) and KI (0.35 g, 2.11 mmol, 4 eq) in MeCN and the reaction mixture was stirred at 80° C. for 16 h. The reaction mixture was cooled to RT, diluted with $H_2O$ and extracted with EtOAc (75 ml×2). Combined organic layers were dried over anhydrous $Na_2SO_4$, filtered, concentrated under reduced pressure to yield crude mass which was then purified by CC to afford 1-benzyl-3-(6-hydroxypyridin-3-yl)-N,4-dimethyl-N-neopentyl-5-(trifluoromethyl)-1H-pyrrole-2-carboxamide (0.15 g, 62%) as a white solid.

Example 04

1-Benzyl-N,4-dimethyl-3-(1-methyl-1H-pyrazol-4-yl)-N-neopentyl-5-(trifluoromethyl)-1H-pyrrole-2-carboxamide To a solution of 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.3 g, 0.60 mmol, 1 eq) in DMF (15 ml) was added 2M $Na_2CO_3$ (0.9 ml, 1.82 mmol, 3 eq) solution and 4-bromo-1-methyl-1H-pyrazole (0.11 g, 0.73 mmol, 1.2 eq). The solution was degassed with Ar for 5 min followed by addition of Pd(dppf)$Cl_2$.$CH_2Cl_2$ (0.034 g, 0.042 mmol, 0.07 eq.) The reaction mixture was stirred at 110° C. for 16 h. The reaction mass was poured onto crushed ice and extracted with EtOAc (50 ml×2). Combined organic layers were dried over anhydrous $Na_2SO_4$, filtered, concentrated under reduced pressure to yield crude mass which was then purified by CC to afford 1-benzyl-N,4-dimethyl-3-(1-methyl-1H-pyrazol-4-yl)-N-neopentyl-5-(trifluoromethyl)-1H-pyrrole-2-carboxamide (0.08 g, 29%) as a white solid.

Example 05

(1-Benzyl-3-(5-methoxypyrazin-2-yl)-4-methyl-5-(trifluoromethyl)-1H-pyrrol-2-yl)(morpholino)methanone 5a): (1-Benzyl-3-bromo-4-methyl-5-(trifluoromethyl)-1H-pyrrol-2-yl)(morpholino)methanone HATU (11.34 g 29.83 mmol, 1.2 eq) and DIPEA (11.1 ml, 62.15 mmol, 2.5 eq) were added to the ice cold solution of 1-benzyl-3-bromo-4-methyl-5-(trifluoromethyl)-1H-pyrrole-2-carboxylic acid (9 g, 24.86 mmol, 1 eq) in DMF (100 ml) and it was stirred for 10 min at same temperature and then morpholine (2.59 g, 29.83 mmol, 1.2 eq) was added. The reaction mixture was warmed to RT and then stirred for 14 h. The reaction mixture was diluted with EtOAc and $H_2O$. The aqueous layer was extracted with EtOAc (300 ml×2), the combined organic layers were washed with water (300 ml×2) and brine (300 ml×2), dried over anhydrous $Na_2SO_4$, filtered, concentrated under reduced pressure to yield crude mass which was then purified by CC to afford (1-benzyl-3-bromo-4-methyl-5-(trifluoromethyl)-1H-pyrrol-2-yl)(morpholino)methanone (10.1 g, 94%) as a white color solid.

5b): (1-benzyl-4-methyl-3-(4,4,5,5-tetramethyl-1,3,2-dioxaborolan-2-yl)-5-(trifluoromethyl)-1H-pyrrol-2-yl) (morpholino)methanone At −78° C. 2.4 M n-BuLi (6.74 ml, 16.17 mmol, 1.2 eq) was added to a solution of (1-benzyl-3-bromo-4-methyl-5-(trifluoromethyl)-1H-pyrrol-2-yl)(morpholino)methanone (6 g, 13.4 mmol, 1 eq) in dry THF (100 ml) and the mixture was stirred at same temperature for 30 min. HBPin (10.7 ml, 67.4 mmol, 5 eq) was added and the reaction mixture was stirred for 45 min at −78° C. The reaction mass was quenched with saturated $NH_4Cl$ solution and extracted with EtOAc (300 ml×2). Combined organic layers were dried over anhydrous $Na_2SO_4$, concentrated under reduced pressure to yield crude mass which was then purified by CC to afford (1-benzyl-4-methyl-3-(4,4,5,5-tetramethyl-1,3,2-dioxaborolan-2-yl)-5-(trifluoromethyl)-1H-pyrrol-2-yl)(morpholino)methanone (3.2 g, 50%) as a white solid.

5c): (1-Benzyl-3-(5-methoxypyrazin-2-yl)-4-methyl-5-(trifluoromethyl)-1H-pyrrol-2-yl) (morpholino)methanone To a solution of (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.4 g, 0.836 mmol, 1 eq) in DMF (15 ml) was added 2M $Na_2CO_3$ (1.2 ml, 2.51 mmol, 3 eq) solution and 2-bromo-5-methoxypyrazine (0.18 mg, 1.04 mmol, 1.2 eq). The solution was degassed with Ar for 5 min followed by addition of Pd(dppf)$Cl_2$.$CH_2Cl_2$ (0.047 g, 0.058 mmol, 0.07 eq.) The reaction mixture was stirred at 110° C. for 16 h. The reaction mass was poured onto crushed ice and extracted with EtOAc (75 ml×2). Combined organic layers were dried over anhydrous $Na_2SO_4$, filtered, concentrated under reduced pressure to yield crude mass which was then purified by CC to afford (1-benzyl-3-(5-methoxypyrazin-2-yl)-4-methyl-5-(trifluoromethyl)-1H-pyrrol-2-yl)(morpholino)methanone (0.18 g, 47%) as a white solid.

Example 06

(1-Benzyl-3-(6-methoxypyridin-3-yl)-4-methyl-5-(trifluoromethyl)-1H-pyrrol-2-yl)(morpholino)methanone To a solution of (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.6 g, 1.21 mmol, 1 eq) in DMF (15 ml) was added 2M $Na_2CO_3$ (1.75 ml, 3.51 mmol, 3 eq) solution and 5-bromo-2-methoxypyridine (0.2 ml, 1.50 mmol, 1.2 eq). The solution was degassed with Ar for 5 min followed by addition of Pd(dppf)$Cl_2$.$CH_2Cl_2$ (0.071 g, 0.047 mmol, 0.07 eq.) The reaction mixture was stirred at 110° C. for 16 h. The reaction mass was poured onto crushed ice and extracted with EtOAc (80 ml×2). Combined organic layers were dried over anhydrous $Na_2SO_4$, filtered and concentrated under reduced pressure to yield crude mass which was then purified by CC to afford (1-benzyl-3-(6-methoxypyridin-3-yl)-4-methyl-5-(trifluoromethyl)-1H-pyrrol-2-yl)(morpholino)-methanone (0.3 g, 52%) as a white solid.

Example 07

(1-Benzyl-3-(6-hydroxypyridin-3-yl)-4-methyl-5-(trifluoromethyl)-1H-pyrrol-2-yl)(morpholino)methanone TMSCl (0.22 ml, 1.74 mmol, 4 eq) was added to a solution of (1-benzyl-3-(6-methoxypyridin-3-yl)-4-methyl-5-(trifluoromethyl)-1H-pyrrol-2-yl)(morpholino)methanone (0.20 g, 0.43 mmol, 1 eq) and KI (0.28 g, 1.74 mmol, 4 eq) in MeCN and the reaction mixture was stirred at 80° C. for 16 h. The reaction mass was cooled to RT, diluted with $H_2O$ and extracted with EtOAc (75 ml×2). Combined organic layers were dried over anhydrous $Na_2SO_4$, filtered, concentrated under reduced pressure to yield crude mass which was then purified by CC to afford (1-benzyl-3-(6-hydroxypyridin-3-yl)-4-methyl-5-(trifluoromethyl)-1H-pyrrol-2-yl)-(morpholino)methanone (0.08 g, 41%) as a white solid.

Example 08

(1-Benzyl-4-methyl-3-(1-methyl-1H-pyrazol-4-yl)-5-(trifluoromethyl)-1H-pyrrol-2-yl)(morpholino)methanone To a solution of (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.6 g, 1.21 mmol, 1 eq) in DMF (15 ml) was added 2M $Na_2CO_3$ (1.75 ml, 3.51 mmol, 3 eq) solution and 4-bromo-1-methyl-1H-pyrazole (0.1 ml, 1.04 mmol, 1.2 eq). The solution was degassed with Ar for 5 min followed by addition of Pd(dppf)Cl$_2$.CH$_2$Cl$_2$ (0.071 g, 0.047 mmol, 0.07 eq.) The reaction mixture was stirred at 110° C. for 16 h. The reaction mass was poured onto crushed ice and extracted with EtOAc (80 ml×2). Combined organic layers were dried over anhydrous $Na_2SO_4$, filtered and concentrated under reduced pressure to yield crude mass which was then purified by CC to afford (1-benzyl-4-methyl-3-(1-methyl-1H-pyrazol-4-yl)-5-(trifluoromethyl)-1H-pyrrol-2-yl)(morpholino)-methanone (0.12 g, 33%) as a white solid.

Example 09

1-Benzyl-N,4-dimethyl-N-neopentyl-3-(1H-pyrazol-4-yl)-5-(trifluoromethyl)-1H-pyrrole-2-carboxamide To a solution of 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (1 g, 2.03 mmol, 1 eq.) in DMF (10 ml) was added 2M $Na_2CO_3$ (3 ml, 6.09 mmol, 3 eq) solution and tert-butyl 4-bromo-1H-pyrazole-1-carboxylate (0.6 g, 2.43 mmol, 1.2 eq). The solution was degassed with Ar for 5 min followed by addition of bis(tri-tert-butyl phosphine) palladium (0.23 g, 0.023 mmol, 0.1 eq.) The reaction mixture is refluxed at 110° C. for 16 h. The reaction mass was poured onto crushed ice and extracted with EtOAc (50 ml×2). Combined organic layers were dried over anhydrous $Na_2SO_4$, filtered, concentrated under reduced pressure to yield crude mass which was then purified by CC to afford benzyl-N,4-dimethyl-N-neopentyl-3-(1H-pyrazol-4-yl)-5-(trifluoromethyl)-1H-pyrrole-2-carboxamide (0.07 g, 8%) as a white solid.

Example 10

(1-Benzyl-4-methyl-3-(1H-pyrazol-4-yl)-5-(trifluoromethyl)-1H-pyrrol-2-yl)(morpholino)methanone To a solution of (1-benzyl-4-methyl-3-(4,4,5,5-tetramethyl-1,3,2-dioxaborolan-2-yl)-5-(trifluoromethyl)-1H-pyrrol-2-yl)(morpholino)methanone (1 g, 2.09 mmol, 1 eq) in DMF (15 ml) was added 2M $Na_2CO_3$ (3.1 ml, 6.27 mmol, 3 eq) solution and tert-butyl 4-bromo-1H-pyrazole-1-carboxylate (1.03 g, 4.18 mmol, 2 eq). The solution was degassed with Ar for 5 min followed by addition of bis(tri-tert-butyl phosphine) palladium (0.24 g, 0.209 mmol, 0.1 eq.) The reaction mixture was stirred at 110° C. for 16 h. The reaction mass was poured onto crushed ice and extracted with EtOAc (100 ml×2). Combined organic layer was dried over anhydrous $Na_2SO_4$, filtered and concentrated under reduced pressure to yield crude mass which was then purified by CC to afford (1-benzyl-4-methyl-3-(1H-pyrazol-4-yl)-5-(trifluoromethyl)-1H-pyrrol-2-yl)-(morpholino)methanone (0.06 g, 7%) as a white solid.

General Procedure A for Suzuki Cross-Coupling:

Under Ar, bis(tri-tert-butylphosphine)palladium(0) was added to a mixture of corresponding pyrroloboronate (0.33 mmol, 1.1 eq.), heteroarylbromide (0.30 mmol, 1.0 eq) and LiOH (0.33 mmol, 1.1 eq) in DMF (1.6 mL). The mixture was heated up to 80° C. under microwave irradiation for 1 h. The reaction mixture was allowed to RT, 2M NaOH (2 ml) was added and the crude product was extracted with EtOAc (2 ml×2). Combined organic layers were concentrated under reduced pressure to yield crude mass which was then purified by flash chromatography or preparative HPLC to afford desired compound.

Example 11

1-Benzyl-N-(2,2-dimethyl-propyl)-N,4-dimethyl-3-pyrimidin-5-yl-5-(trifluoromethyl)-1H-pyrrole-2-carboxylic acid amide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.31 mmol, 1.1 eq) was converted with 5-bromopyrimidine (0.28 mmol, 1.0 eq) to give desired 1-benzyl-N-(2,2-dimethyl-propyl)-N,4-dimethyl-3-pyrimidin-5-yl-5-(trifluoromethyl)-1H-pyrrole-2-carboxylic acid amide (47 mg, 38%).

Example 12

1-Benzyl-N-(2,2-dimethyl-propyl)-3-(2-methoxy-pyrimidin-5-yl)-N,4-dimethyl-5-(trifluoromethyl)-1H-pyrrole-2-carboxylic acid amide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.22 mmol, 1.1 eq) was converted with 5-bromo-2-methoxypyrimidine (0.20 mmol, 1.0 eq) to give desired 1-benzyl-N-(2,2-dimethyl-propyl)-3-(2-methoxy-pyrimidin-5-yl)-N,4-dimethyl-5-(trifluoromethyl)-1H-pyrrole-2-carboxylic acid amide (91 mg, 96%).

Example 13

1-Benzyl-3-(5-chloro-thiophen-2-yl)-N-(2,2-dimethyl-propyl)-N,4-dimethyl-5-(trifluoromethyl)-1H-pyrrole-2-carboxylic acid amide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.31 mmol, 1.1 eq) was converted with 2-bromo-5-chlorothiophene (0.28 mmol, 1.0 eq) to give desired 1-benzyl-3-(5-chloro-thiophen-2-yl)-N-(2,2-dimethyl-propyl)-N,4-dimethyl-5-(trifluoromethyl)-1H-pyrrole-2-carboxylic acid amide (24 mg, 18%).

Example 14

[1-Benzyl-3-(2-methoxy-pyrimidin-5-yl)-4-methyl-5-(trifluoromethyl)-1H-pyrrol-2-yl]-morpholin-4-yl-methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.31 mmol, 1.1 eq) was converted with 5-bromo-2-methoxypyrimidine (0.28, 1.0 eq) to give desired [1-benzyl-3-(2-methoxy-pyrimidin-5-yl)-4-methyl-5-(trifluoromethyl)-1H-pyrrol-2-yl]-morpholin-4-yl-methanone (103 mg, 86%).

Example 15

[1-Benzyl-4-methyl-3-pyrimidin-5-yl-5-(trifluoromethyl)-1H-pyrrol-2-yl]-morpholin-4-yl-methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.31 mmol, 1.1 eq) was converted with 5-bromopyrimidine (0.28 mmol, 1.0 eq) to give desired [1-benzyl-4-methyl-3-pyrimidin-5-yl-5-(trifluoromethyl)-1H-pyrrol-2-yl]-morpholin-4-yl-methanone (46 mg, 39%).

Example 16

1-Benzyl-3-(3,5-dimethyl-isoxazol-4-yl)-N-(2,2-dimethyl-propyl)-N,4-dimethyl-5-(trifluoromethyl)-1H-pyrrole-2-carboxylic acid amide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 4-bromo-3,5-dimethylisoxazole (0.30 mmol, 1.0 eq) to give desired 1-benzyl-3-(3,5-dimethyl-isoxazol-4-yl)-N-(2,2-dimethyl-propyl)-N,4-dimethyl-5-(trifluoromethyl)-1H-pyrrole-2-carboxylic acid amide (44 mg, 32%).

Example 17

1-Benzyl-N-(2,2-dimethyl-propyl)-3-[3-fluoro-5-(trifluoromethyl)-pyridin-2-yl]-N,4-dimethyl-5-(trifluoromethyl)-1H-pyrrole-2-carboxylic acid amide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 2-bromo-3-fluoro-5-(trifluoromethyl)pyridine (0.30 mmol, 1.1 eq) to give desired 1-benzyl-N-(2,2-dimethyl-propyl)-3-[3-fluoro-5-(trifluoromethyl)-pyridin-2-yl]-N,4-dimethyl-5-(trifluoromethyl)-1H-pyrrole-2-carboxylic acid amide (28 mg, 18%).

Example 18

1-Benzyl-3-(5-chloro-pyrimidin-2-yl)-N-(2,2-dimethyl-propyl)-N,4-dimethyl-5-(trifluoromethyl)-1H-pyrrole-2-carboxylic acid amide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 2-bromo-5-chloropyrimidine (0.30 mmol, 1.0 eq) to give desired 1-Benzyl-3-(5-chloro-pyrimidin-2-yl)-N-(2,2-dimethyl-propyl)-N,4-dimethyl-5-(trifluoromethyl)-1H-pyrrole-2-carboxylic acid amide (35 mg, 24%).

Example 19

1-Benzyl-3-(6-cyano-4-methylpyridin-3-yl)-N,4-dimethyl-N-neopentyl-5-(trifluoromethyl)-1H-pyrrole-2-carboxamide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 5-bromo-4-methylpicolinonitrile (0.30 mmol, 1.0 eq) to give desired 1-benzyl-3-(6-cyano-4-methyl-pyridin-3-yl)-N,4-dimethyl-N-neopentyl-5-(trifluoromethyl)-1H-pyrrole-2-carboxamide (0.061 mg, 42%).

Example 20

1-Benzyl-3-(6-chloro-4-methyl-pyridin-3-yl)-N-(2,2-dimethyl-propyl)-N,4-dimethyl-5-(trifluoromethyl)-1H-pyrrole-2-carboxylic acid amide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 5-bromo-2-chloro-4-methylpyridine (0.30 mmol, 1.0 eq) to give desired 1-benzyl-3-(6-chloro-4-methyl-pyridin-3-yl)-N-(2,2-dimethyl-propyl)-N,4-dimethyl-5-(trifluoromethyl)-1H-pyrrole-2-carboxylic acid amide (70 mg, 47%).

Example 21

1-Benzyl-N-(2,2-dimethyl-propyl)-3-(6-methoxy-4-methyl-pyridin-3-yl)-N,4-dimethyl-5-(trifluoromethyl)-1H-pyrrole-2-carboxylic acid amide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 5-bromo-2-methoxy-4-methylpyridine (0.30 mmol, 1.0 eq) to give desired 1-benzyl-N-(2,2-dimethyl-propyl)-3-(6-methoxy-4-methyl-pyridin-3-yl)-N,4-dimethyl-5-(trifluoromethyl)-1H-pyrrole-2-carboxylic acid amide (107 mg, 73%).

Example 22

1-Benzyl-3-(6-chloro-pyridazin-3-yl)-N-(2,2-dimethyl-propyl)-N,4-dimethyl-5-(trifluoromethyl)-1H-pyrrole-2-carboxylic acid amide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 3-bromo-6-chloropyridazine (0.30 mmol, 1.0 eq) to give desired 1-benzyl-3-(6-chloro-pyridazin-3-yl)-N-(2,2-dimethyl-propyl)-N,4-dimethyl-5-(trifluoromethyl)-1H-pyrrole-2-carboxylic acid amide (36 mg, 25%).

Example 23

[1-Benzyl-3-(3,5-dimethyl-isoxazol-4-yl)-4-methyl-5-(trifluoromethyl)-1H-pyrrol-2-yl]-morpholin-4-yl-methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 4-bromo-3,5-dimethyl-isoxazole (0.30 mmol, 1.0 eq) to give desired [1-benzyl-3-(3,5-dimethyl-isoxazol-4-yl)-4-methyl-5-(trifluoromethyl)-1H-pyrrol-2-yl]-morpholin-4-yl-methanone (43 mg, 32%).

Example 24

[1-Benzyl-3-[3-fluoro-5-(trifluoromethyl)-pyridin-2-yl]-4-methyl-5-(trifluoromethyl)-1H-pyrrol-2-yl]-morpholin-4-yl-methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 2-bromo-3-fluoro-5-(trifluoromethyl)pyridine (0.30 mmol, 1.0 eq) to give desired [1-benzyl-3-[3-fluoro-5-(trifluoromethyl)-pyridin-2-yl]-4-methyl-5-(trifluoromethyl)-1H-pyrrol-2-yl]-morpholin-4-yl-methanone (52 mg, 34%).

Example 25

[1-Benzyl-3-(5-chloro-pyrimidin-2-yl)-4-methyl-5-(trifluoromethyl)-1H-pyrrol-2-yl]-morpholin-4-yl-methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 2-bromo-5-chloropyrimidine (0.30 mmol, 1.0 eq) to give desired [1-benzyl-3-(5-chloro-pyrimidin-2-yl)-4-methyl-5-(trifluoromethyl)-1H-pyrrol-2-yl]-morpholin-4-yl-methanone (74 mg, 53%).

Example 26

5-[1-Benzyl-4-methyl-2-(morpholine-4-carbonyl)-5-(trifluoromethyl)-1H-pyrrol-3-yl]-4-methyl-pyridine-2-carbonitrile According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 5-bromo-4-methylpicolinonitrile (0.30 mmol, 1.0 eq) to give desired 5-[1-benzyl-4-methyl-2-(morpholine-4-carbonyl)-5-(trifluoromethyl)-1H-pyrrol-3-yl]-4-methyl-pyridine-2-carbonitrile (47 mg, 33%).

Example 27

[1-Benzyl-3-(6-chloro-4-methyl-pyridin-3-yl)-4-methyl-5-(trifluoromethyl)-1H-pyrrol-2-yl]-morpholin-4-yl-methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 5-bromo-2-chloro-4-methylpyridine (0.30 mmol, 1.0 eq) to give desired [1-benzyl-3-(6-chloro-4-methyl-pyridin-3-yl)-4-methyl-5-(trifluoromethyl)-1H-pyrrol-2-yl]-morpholin-4-yl-methanone (62 mg, 43%).

Example 28

[1-Benzyl-3-(6-methoxy-4-methyl-pyridin-3-yl)-4-methyl-5-(trifluoromethyl)-1H-pyrrol-2-yl]-morpholin-4-yl-methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 5-bromo-2-methoxy-4-methylpyridine (0.30 mmol, 1.0 eq) to give desired [1-benzyl-3-(6-methoxy-4-methyl-pyridin-3-yl)-4-methyl-5-(trifluoromethyl)-1H-pyrrol-2-yl]-morpholin-4-yl-methanone (17 mg, 12%).

Example 29

[1-Benzyl-3-(6-chloro-pyridazin-3-yl)-4-methyl-5-(trifluoromethyl)-1H-pyrrol-2-yl]-morpholin-4-yl-methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 3-bromo-6-chloropyridazine (0.30 mmol, 1.0 eq) to give desired [1-benzyl-3-(6-chloro-pyridazin-3-yl)-4-methyl-5-(trifluoromethyl)-1H-pyrrol-2-yl]-morpholin-4-yl-methanone (32 mg, 23%).

Example 30

1-Benzyl-3-(5-methoxypyrimidin-2-yl)-N,4-dimethyl-N-neopentyl-5-(trifluoromethyl)-1H-pyrrole-2-carboxamide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 2-bromo-5-methoxypyridine (0.30 mmol, 1.0 eq) to give desired 1-benzyl-3-(5-methoxypyrimidin-2-yl)-N,4-dimethyl-N-neopentyl-5-(trifluoromethyl)-1H-pyrrole-2-carboxamide (28 mg, 20%).

Example 31

1-Benzyl-3-(5-fluoropyridin-2-yl)-N,4-dimethyl-N-neopentyl-5-(trifluoromethyl)-1H-pyrrole-2-carboxamide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 2-bromo-5-fluoropyridine (0.30 mmol, 1.0 eq) to give desired 1-benzyl-3-(5-fluoropyridin-2-yl)-N,4-dimethyl-N-neopentyl-5-(trifluoromethyl)-1H-pyrrole-2-carboxamide (25 mg, 18%).

Example 32

1-Benzyl-N,4-dimethyl-N-neopentyl-3-(pyridazin-4-yl)-5-(trifluoromethyl)-1H-pyrrole-2-carboxamide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 4-bromopyridazine (0.30 mmol, 1.0 eq) to give desired 1-benzyl-N,4-dimethyl-N-neopentyl-3-(pyridazin-4-yl)-5-(trifluoromethyl)-1H-pyrrole-2-carboxamide (18 mg, 13%).

Example 33

1-Benzyl-3-(5-fluoropyrimidin-2-yl)-N,4-dimethyl-N-neopentyl-5-(trifluoromethyl)-1H-pyrrole-2-carboxamide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 2-bromo-5-fluoropyrimidine (0.30 mmol, 1.0 eq) to give desired 1-benzyl-3-(5-fluoropyrimidin-2-yl)-N,4-dimethyl-N-neopentyl-5-(trifluoromethyl)-1H-pyrrole-2-carboxamide (7 mg, 5%).

Example 34

1-Benzyl-N,4-dimethyl-N-neopentyl-3-(pyrazin-2-yl)-5-(trifluoromethyl)-1H-pyrrole-2-carboxamide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 2-bromopyrazine (0.30 mmol, 1.0 eq) to give desired benzyl-N,4-dimethyl-N-neopentyl-3-(pyrazin-2-yl)-5-(trifluoromethyl)-1H-pyrrole-2-carboxamide (13 mg, 10%).

Example 35

1-Benzyl-N,4-dimethyl-N-neopentyl-3-(pyrimidin-2-yl)-5-(trifluoromethyl)-1H-pyrrole-2-carboxamide According to general procedure A 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (0.33 mmol, 1.1 eq) was converted with 2-bromopyrimidine (0.30 mmol, 1.0 eq) to give desired 1-benzyl-N,4-dimethyl-N-neopentyl-3-(pyrimidin-2-yl)-5-(trifluoromethyl)-1H-pyrrole-2-carboxamide (14 mg, 10%).

Example 36

(1-Benzyl-3-(5-fluoropyridin-2-yl)-4-methyl-5-(trifluoromethyl)-1H-pyrrol-2-yl)(morpholino)methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 2-bromo-5-fluoropyridine (0.30 mmol, 1.0 eq) to give desired (1-benzyl-3-(5-fluoropyridin-2-yl)-4-methyl-5-(trifluoromethyl)-1H-pyrrol-2-yl)(morpholino)methanone (42 mg, 31%).

Example 37

(1-Benzyl-4-methyl-3-(pyridazin-4-yl)-5-(trifluoromethyl)-1H-pyrrol-2-yl)(morpholino)methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 4-bromopyridazine (0.30 mmol, 1.0 eq) to give desired (1-benzyl-4-methyl-3-(pyridazin-4-yl)-5-(trifluoromethyl)-1H-pyrrol-2-yl)(morpholino)methanone (15 mg, 12%).

Example 38

(1-Benzyl-3-(5-fluoropyrimidin-2-yl)-4-methyl-5-(trifluoromethyl)-1H-pyrrol-2-yl)(morpholino)methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 2-bromo-5-fluoropyrimidine (0.30 mmol, 1.0 eq) to give desired (1-benzyl-3-(5-fluoropyrimidin-2-yl)-4-methyl-5-(trifluoromethyl)-1H-pyrrol-2-yl)(morpholino)methanone (60 mg, 45%).

Example 39

(1-Benzyl-4-methyl-3-(pyrazin-2-yl)-5-(trifluoromethyl)-1H-pyrrol-2-yl)(morpholino)methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 2-bromopyrazine (0.30 mmol, 1.0 eq) to give desired (1-benzyl-4-methyl-3-(pyrazin-2-yl)-5-(trifluoromethyl)-1H-pyrrol-2-yl)(morpholino)methanone (55 mg, 43%).

Example 40

(1-Benzyl-4-methyl-3-(pyrimidin-2-yl)-5-(trifluoromethyl)-1H-pyrrol-2-yl)(morpholino)methanone According to general procedure A (1-benzyl-4-methyl-3-(4,4,5,5-tetramethyl-1,3,2-dioxaborolan-2-yl)-5-(trifluoromethyl)-1H-pyrrol-2-yl)(morpholino)methanone (0.33 mmol, 1.1 eq) was converted with 2-bromopyrimidine (0.30 mmol, 1.0 eq) to give desired (1-benzyl-4-methyl-3-(pyrimidin-2-yl)-5-(trifluoromethyl)-1H-pyrrol-2-yl)(morpholino)methanone (75 mg, 58%).

General Synthetic Route 2:

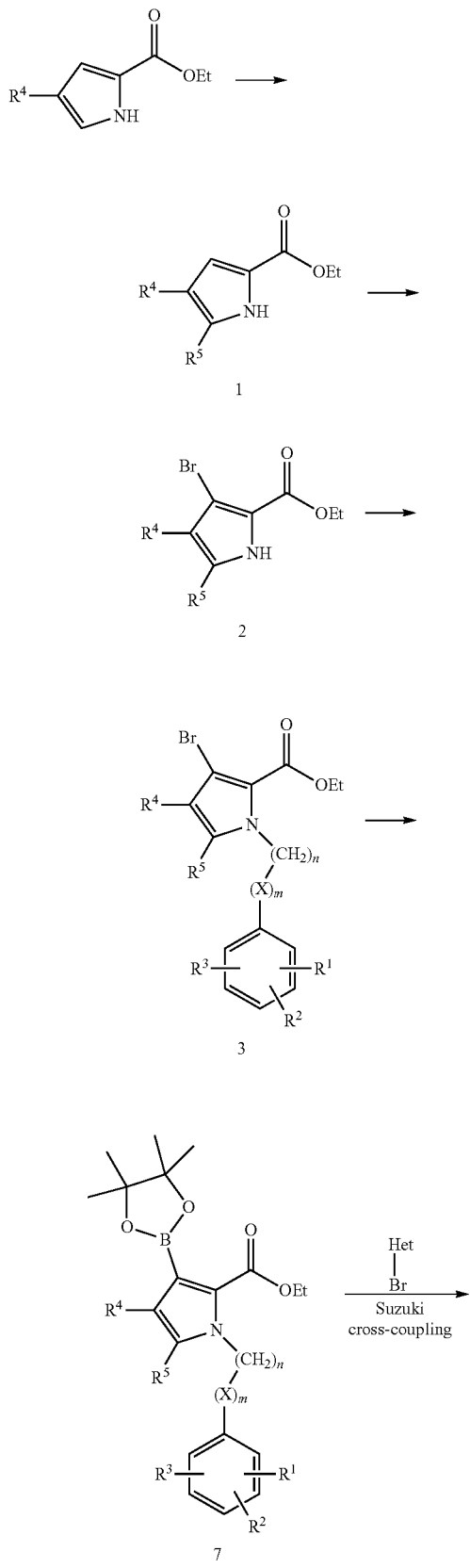

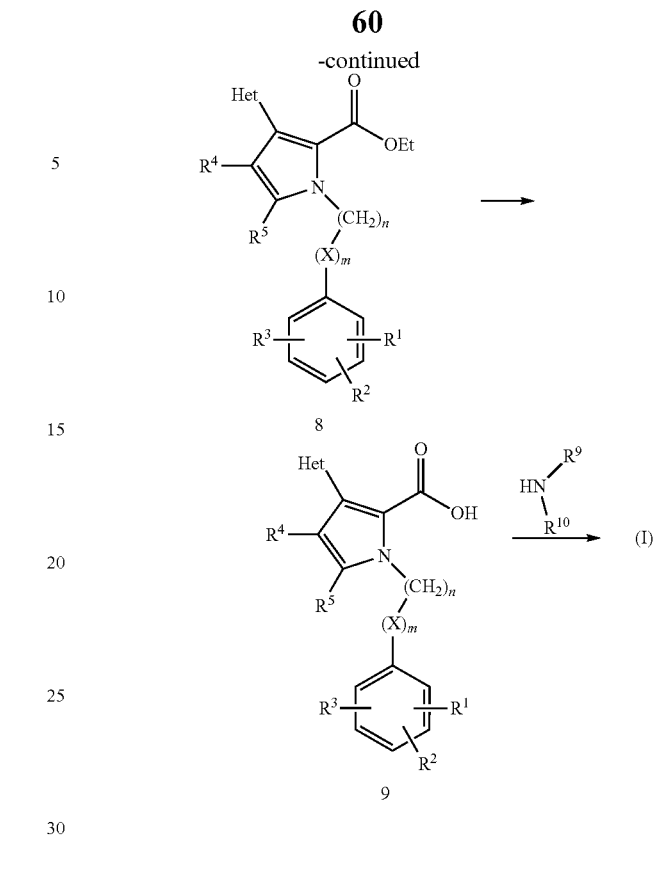

Example 41

1-Benzyl-3-(5-chloro-pyridin-2-yl)-N-(2,2-dimethyl-propyl)-N,4-dimethyl-5-(trifluoromethyl)-1H-pyrrole-2-carboxylic acid amide 41a): Ethyl 4-methyl-5-(trifluoromethyl)-1H-pyrrole-2-carboxylate This reaction was carried out in 4 batches of 1.2 g using the same procedure. To a mixture of ethyl 4-methyl-1H-pyrrole-2-carboxylate (1.2 g, 7.8 mmol), $K_2HPO_4$ (4.05 g, 23.3 mmol) and dichlorotris(1,10-phenanthroline)-ruthenium(II) hydrate (112 mg, 0.15 mmol) in Ar degassed dry MeCN (40 mL) was added $CF_3SO_2Cl$ (1.24 mL, 11.6 mmol). The reaction mixture was stirred for 5 d at RT adjacent to a fluorescent light bulb (E27-23 W, 4000K, 165 mA.). All reaction mixtures were combined and diluted with EtOAc and $H_2O$. The aqueous layer was extracted with EtOAc (300 mL). The organic layers were combined and the solvent was evaporated. The crude product was purified by flash CC (silica, gradient heptane/EtOAc, 9:1→4:1) to furnish the desired product (3.3 g, 48%). An impure batch was recrystallised from heptane (10 mL) to give another batch of pure title compound (1.55 g, 23%). Total yield: 4.85 g (70%).

41b): Ethyl 3-bromo-4-methyl-5-(trifluoromethyl)-1H-pyrrole-2-carboxylate

To a solution of ethyl 4-methyl-5-(trifluoromethyl)-1H-pyrrole-2-carboxylate (1 g, 4.5 mmol) in MeCN (12 mL) was added $K_2CO_3$ (0.656 g, 4.8 mmol). The suspension cooled to 0° C. and NBS (0.85 g, 4.8 mmol) was portionwise added. The reaction mixture was stirred for a few minutes, warmed up to RT and H₂O (24 mL) was added. After 45 min, the solids which were formed were filtered off and washed with EtOH/H₂O (1:2, 30 mL) and dried on air, to afford the desired product (1.18 g, 87%) as a white fluffy solid.

41c): Ethyl 1-benzyl-3-bromo-4-methyl-5-(trifluoromethyl)-1H-pyrrole-2-carboxylate To a solution of ethyl 3-bromo-4-methyl-5-(trifluoromethyl)-1H-pyrrole-2-carboxylate (600 mg, 2.00 mmol) in dry MeCN (10 mL) was added K₂CO₃ (553 mg, 4.00 mmol) and benzyl bromide (262 μL, 2.20 mmol). The suspension was stirred overnight at 80° C. Subsequently, silica (ca. 1 g) was added and the resulting suspension was filtered off. The residue was washed with EtOAc (20 mL) and the combination of filtrate and washing was concentrated in vacuo. The residue was dissolved in heptane/DCM (1:1, few mL) and used for flash CC (silica, gradient heptane/EtOAc, 1:0→9:1) to result in 798 mg (97%, purity 95%) of the desired product as a clear oil.

41d): Ethyl 1-benzyl-4-methyl-3-(4,4,5,5-tetramethyl-1,3,2-dioxaborolan-2-yl)-5-(trifluoromethyl)-1H-pyrrole-2-carboxylate A round bottomed flask was charged with ethyl 1-benzyl-3-bromo-4-methyl-5-(trifluoromethyl)-1H-pyrrole-2-carboxylate (309 mg, 0.752 mmol) and transferred into a glove box. The pyrrole was dissolved in dry and degassed dioxane (10 mL), addition of Pd₂(dba)₃ (33 mg, 0.036 mmol) and XPhos (70 mg, 0.147 mmol) resulted in a purple solution. Warming to around 90° C. resulted in a deep orange solution.

Subsequently, dry and degassed Et₃N (331 μL, 2.38 mmol) and HBPin (4,4,5,5-tetramethyl-1,3,2-dioxaborolane, 345 μL, 2.38 mmol) were added. The flask with the reaction mixture was transferred out of the glove box and N₂ flushed condensor was placed on the flask. Heating at 100° C. for 2 h resulted in a colourless solution with a voluminous white precipitate and some palladium black. Carefully, saturated aqueous NH₄Cl (40 mL) was added (gas evolution) and the resulting mixture was stirred well for 10 min. Addition of H₂O (10 mL) and EtOAc (40 mL) resulted in clear two phase system with palladium black. The organic layer was decanted, the residual aqueous layer was combined with a fresh portion of EtOAc (40 mL). The mixture was stirred well and the organic layer was decanted. The combination of organic layers was dried (Na₂SO₄) and concentrated in vacuo. The residue was dissolved in DCM and used for flash CC (silica, gradient heptane/EtOAc, 1:0→4:1) to result in 279 mg (76%, purity 90%) of the desired product as a colourless oil.

41e): Ethyl 1-benzyl-3-(5-chloropyridin-2-yl)-4-methyl-5-(trifluoromethyl)-1H-pyrrole-2-carboxylate A round bottomed flask was charged with ethyl 1-benzyl-4-methyl-3-(4,4,5,5-tetramethyl-1,3,2-dioxaborolan-2-yl)-5-(trifluoromethyl)-1H-pyrrole-2-carboxylate (232 mg, 0.478 mmol), 2-bromo-5-chloropyridine (153 mg, 0.796 mmol), PdCl₂(dppf) (43 mg, 0.053 mmol) and K₃PO₄ (338 mg, 1.59 mmol) and transferred into a glove box. Addition of dry and degassed THF (15 mL) resulted in a slightly orange suspension. The flask with the reaction mixture was transferred out of the glove box and a nitrogen flushed condensor was placed on the flask. Heating at 70° C. for 20 h was followed by addition of 2-bromo-5-chloropyridine (77 mg, 0.398 mmol) and PdCl₂(dppf) (43 mg, 0.053 mmol). The reaction mixture was heated at 70° C. for 2 d, followed by concentration in vacuo. The residue was used for flash CC (silica, gradient heptane/EtOAc, 1:0→9:1) to result in 100 mg (37%, purity 75%) of impure product as a clear oil.

41 f): 1-Benzyl-3-(5-chloropyridin-2-yl)-4-methyl-5-(trifluoromethyl)-1H-pyrrole-2-carboxylic acid To a solution of impure ethyl 1-benzyl-3-(5-chloropyridin-2-yl)-4-methyl-5-(trifluoromethyl)-1H-pyrrole-2-carboxylate (100 mg, 178 mmol) in DMSO (7 mL) were added crushed pellets of NaOH (28 mg, 0.71 mmol). The reaction mixture was stirred at RT overnight. Subsequently, aqueous 1 M KHSO₄ (100 mL), H₂O (10 mL) and EtOAc (30 mL) were added to result in a clear two phase system. The layers were separated, the aqueous layer was extracted with EtOAc (30 mL). The combination of organic layers was washed with H₂O (20 mL) twice and with brine, dried (Na₂SO₄) and concentrated in vacuo. The residue was dissolved in DCM and used for preparative TLC (silica, heptane/EtOAc, 2:1) to provide 78 mg (100%) of the desired product as a white solid.

41g): 1-Benzyl-3-(5-chloro-pyridin-2-yl)-N-(2, 2-dimethyl-propyl)-N,4-dimethyl-5-(trifluoromethyl)-1H-pyrrole-2-carboxylic acid amide According to general procedure B [described below] 1-benzyl-3-(5-chloropyridin-2-yl)-4-methyl-5-(trifluoromethyl)-1H-pyrrole-2-carboxylic acid (40 mg, 0.091 mmol) was converted with N,2,2-trimethylpropan-1-amine hydrochloride [see section (B)](16.7 mg, 0.122 mmol) to give desired 1-benzyl-3-(5-chloro-pyridin-2-yl)-N-(2,2-dimethyl-propyl)-N,4-dimethyl-5-(trifluoromethyl)-1H-pyrrole-2-carboxylic acid amide (41 mg, 94%).

General Procedure B for Amide Coupling:

The corresponding carboxylic acid (1 eq) and the corresponding amine (1.0-1.5 eq) were dissolved in DME or DMF, DIPEA (3-5 eq) BOP-Cl (1.0-2.5 eq) were added. The reaction mixture was stirred at RT or, if necessary, 60° C. for 1-20 h and then cooled to RT. The reaction mixture was poured in aqueous 1M KHSO₄ and the product was extracted using EtOAc or DCM (3×). The combined organic layers were washed with aqueous 1M KHSO₄ (2×), aqueous saturated NaHCO₃ (3×) and brine (2×) before drying on Na₂SO₄ and concentration in vacuo. The product was purified using flash CC (silica).

Example 42

[1-Benzyl-3-(5-chloro-pyridin-2-yl)-4-methyl-5-(trifluoromethyl)-1H-pyrrol-2-yl]-morpholin-4-yl-methanone According to general procedure C [see below] 1-benzyl-3-(5-chloropyridin-2-yl)-4-methyl-5-(trifluoromethyl)-1H-pyrrole-2-carboxylic acid [see 41f] (38 mg, 0.086 mmol) was converted with morpholine (17 μL, 0.193 mmol) to give desired [1-benzyl-3-(5-chloro-pyridin-2-yl)-4-methyl-5-(trifluoromethyl)-1H-pyrrol-2-yl]-morpholin-4-yl-methanone (29 mg, 72%).

General Procedure C for Amide Coupling:

The corresponding carboxylic acid (1 eq) was suspended in dry DCM. The corresponding amine (0.8-2.5 eq) was added at RT or 0° C., followed by EDCl (1.0-1.5 eq) and HOAt (0.1-0.3 eq). The reaction mixture was stirred at RT

Example 43

1-Benzyl-3-(5-chloro-pyridin-2-yl)-N,4-dimethyl-N-(2-methylsulfonyl-ethyl)-5-(trifluoromethyl)-1H-pyrrole-2-carboxylic acid amide According to general procedure B [see 41g)] 1-benzyl-3-(5-chloropyridin-2-yl)-4-methyl-5-(trifluoromethyl)-1H-pyrrole-2-carboxylic acid [see 41f)] (110 mg, 0.279 mmol) was converted with 2-(methylamino)-1-(methylsulfonyl) ethane (46 mg, 0.334 mmol) to give desired 1-benzyl-3-(5-chloro-pyridin-2-yl)-N,4-dimethyl-N-(2-methylsulfonyl-ethyl)-5-(trifluoromethyl)-1H-pyrrole-2-carboxylic acid amide (62 mg, 42%).

Example 44

[1-Benzyl-3-(5-chloro-pyrimidin-2-yl)-4-methyl-5-(trifluoromethyl)-1H-pyrrol-2-yl]-(1,1-dioxo-[1,4]thiazinan-4-yl)-methanone 44a): Ethyl 1-benzyl-3-(5-chloropyrimidin-2-yl)-4-methyl-5-(trifluoromethyl)-1H-pyrrole-2-carboxylate A flask was charged with ethyl 1-benzyl-4-methyl-3-(4,4,5,5-tetramethyl-1,3,2-dioxaborolan-2-yl)-5-(trifluoromethyl)-1H-pyrrole-2-carboxylate [see 41 d)] (947 mg, 2.1 mmol), $Cs_2CO_3$ (2.14 g, 6.50 mmol), 5-chloro-2-iodopyrimidine (781 mg, 3.2 mmol), DME (16 mL) and $H_2O$ (4 mL). The suspension was purged with Ar for 50 min before $PdCl_2$(dppf) (158 mg, 0.2 mmol) was added. The reaction mixture was stirred at 95° C. for 2 h. The reaction mixture was cooled and filtered over celite and washed with DCM (30 mL). The filtrate was concentrated in vacuo and purified by flash CC (silica, gradient heptane/EtOAc, 1:0→9:1) to give the desired product 412 mg (45%) as a colourless oil.

44b): 1-Benzyl-3-(5-chloropyrimidin-2-yl)-4-methyl-5-(trifluoromethyl)-1H-pyrrole-2-carboxylic acid To a solution of ethyl 1-benzyl-3-(5-chloropyrimidin-2-yl)-4-methyl-5-(trifluoromethyl)-1H-pyrrole-2-carboxylate (613 mg, 1.45 mmol) in dry DMSO (10 mL) was added at 0° C. NaOH (191 mg, 4.8 mmol). The reaction mixture was stirred at RT for 3 d. Aqueous 0.5 M $KHSO_4$ was added until pH 6 was reached and EtOAc (20 mL) was added. The layers were separated and the aqueous layer was extracted with EtOAc (10 mL). The combination of organic layers was washed 4× with brine (10 mL), dried ($Na_2SO_4$) and concentrated in vacuo. The residue was taken in $Et_2O$ (20 mL) and the organic layer was washed 4× with brine (10 mL), dried ($Na_2SO_4$) and concentrated in vacuo to give 600 mg ('105%') of the desired product as a yellow solid.

44c): [1-Benzyl-3-(5-chloro-pyrimidin-2-yl)-4-methyl-5-(trifluoromethyl)-1H-pyrrol-2-yl]-(1,4-dioxo-[1,4]thiazinan-4-yl)-methanone According to general procedure C [see example 42] 1-benzyl-3-(5-chloropyrimidin-2-yl)-4-methyl-5-(trifluoromethyl)-1H-pyrrole-2-carboxylic acid (100 mg, 0.25 mmol) was converted with thiomorpholine 1,1-dioxide (42.7 mg, 0.32 mmol) to give desired [1-benzyl-3-(5-chloro-pyrimidin-2-yl)-4-methyl-5-(trifluoromethyl)-1H-pyrrol-2-yl]-(1,1-dioxo-[1,4]thiazinan-4-yl)-methanone (76 mg, 59%).

Example 45

[1-Benzyl-3-(5-chloro-pyrimidin-2-yl)-4-methyl-5-(trifluoromethyl)-1H-pyrrol-2-yl]-(2,2-dimethyl-morpholin-4-yl)-methanone According to general procedure C [see example 42] 1-benzyl-3-(5-chloropyrimidin-2-yl)-4-methyl-5-(trifluoromethyl)-1H-pyrrole-2-carboxylic acid [see 44b)] (100 mg, 0.25 mmol) was converted with 2,2-dimethylmorpholine (27.9 mg, 0.24 mmol) to give desired [1-benzyl-3-(5-chloro-pyrimidin-2-yl)-4-methyl-5-(trifluoromethyl)-1H-pyrrol-2-yl]-(2,2-dimethyl-morpholin-4-yl)-methanone (79 mg, 63%).

Example 46

1-Benzyl-3-(5-chloro-pyrimidin-2-yl)-N-cyclopropyl-4-methyl-5-(trifluoromethyl)-1H-pyrrole-2-carboxylic acid amide According to general procedure B [see 41g)] 1-benzyl-3-(5-chloropyrimidin-2-yl)-4-methyl-5-(trifluoromethyl)-1H-pyrrole-2-carboxylic acid [see 44b)] (100 mg, 0.25 mmol) was converted with cyclopropanamine (0.02 mL, 0.30 mmol) to give desired 1-benzyl-3-(5-chloro-pyrimidin-2-yl)-N-cyclopropyl-4-methyl-5-(trifluoromethyl)-1H-pyrrole-2-carboxylic acid amide (58 mg, 53%).

Example 47

4-[1-Benzyl-3-(5-chloro-pyrimidin-2-yl)-4-methyl-5-(trifluoromethyl)-1H-pyrrole-2-carbonyl]-piperazin-2-one According to general procedure D [see below] 1-benzyl-3-(5-chloropyrimidin-2-yl)-4-methyl-5-(trifluoromethyl)-1H-pyrrole-2-carboxylic acid [see 44b)] (100 mg, 0.25 mmol) was converted with 2-oxopiperazine (32 mg, 0.32 mmol) to give desired 4-[1-benzyl-3-(5-chloro-pyrimidin-2-yl)-4-methyl-5-(trifluoromethyl)-1H-pyrrole-2-carbonyl]-piperazin-2-one (34 mg, 28%).

General Procedure D for Amide Coupling:

To a solution of the corresponding carboxylic acid (1 eq), $Et_3N$ (2.5 eq) and the corresponding (1.0-1.5 eq) in DCM was added EDCl (1.2 eq) and HOAt (0.1-0.3 eq) at 0° C. under $N_2$. DMF was added and the reaction mixture was stirred overnight at RT. The reaction mixture was diluted with $H_2O$ and DCM and stirred for 15 min. The organic layer was separated and concentrated in vacuo. The product was purified using flash CC (silica). If necessary the product was purified further by reversed phase chromatography (C18) and the solvents were removed by freeze-drying.

Example 48

1-Benzyl-N-(2-carbamoyl-2-methyl-propyl)-3-(5-chloro-pyrimidin-2-yl)-N,4-dimethyl-5-(trifluoromethyl)-1H-pyrrole-2-carboxylic acid amide According to general procedure B [see 41g)] 1-benzyl-3-(5-chloropyrimidin-2-yl)-4-methyl-5-(trifluoromethyl)-1H-

*(continuation from previous page:)* for 1-3 d. Subsequently it was either (A) brought on silica or (B) diluted with $H_2O$ and DCM, the aqueous layer extracted with DCM and the organics combined and concentrated in vacuo. The crude product was purified by flash CC (silica), to afford the desired product.

pyrrole-2-carboxylic acid [see 44b)] (60 mg, 0.152 mmol) was converted with 2,2-dimethyl-3-(methylamino)propanamide hydrochloride [see section (B)] (30.3 mg, 0.182 mmol) to give desired 1-benzyl-N-(2-carbamoyl-2-methyl-propyl)-3-(5-chloro-pyrimidin-2-yl)-N,4-dimethyl-5-(trifluoromethyl)-1H-pyrrole-2-carboxylic acid amide (71 mg, 85%).

Example 49

1-Benzyl-3-(5-chloro-pyrimidin-2-yl)-N-(2-cyano-2-methyl-propyl)-N,4-dimethyl-5-(trifluoromethyl)-1H-pyrrole-2-carboxylic acid amide According to general procedure B [see 41g)] 1-benzyl-3-(5-chloropyrimidin-2-yl)-4-methyl-5-(trifluoromethyl)-1H-pyrrole-2-carboxylic acid [see 44b)] (60 mg, 0.152 mmol) was converted with 2,2-dimethyl-3-(methylamino)propanenitrile hydrochloride [see section (B)] (27.0 mg, 0.182 mmol) to give desired 1-benzyl-3-(5-chloro-pyrimidin-2-yl)-N-(2-cyano-2-methyl-propyl)-N,4-dimethyl-5-(trifluoromethyl)-1H-pyrrole-2-carboxylic acid amide (41 mg, 51%).

Example 50

1-Benzyl-3-(5-chloro-pyridin-2-yl)-N-isopropyl-N,4-dimethyl-5-(trifluoromethyl)-1H-pyrrole-2-carboxylic acid amide The desired compound was synthesized following general synthetic route 2 (see 41).

Example 51

1-Benzyl-N-isopropyl-N,4-dimethyl-3-(1-methyl-1H-pyrazol-3-yl)-5-(trifluoromethyl)-1H-pyrrole-2-carboxylic acid amide The desired compound was synthesized following general synthetic route 1 (see 01).

Example 52

1-Benzyl-3-(5-chloro-pyrimidin-2-yl)-N-isopropyl-4-methyl-5-(trifluoromethyl)-1H-pyrrole-2-carboxylic acid amide The desired compound was synthesized following general synthetic route 1 (see 01).

Example 53

1-Benzyl-3-(5-chloro-pyridin-2-yl)-N-isopropyl-4-methyl-5-(trifluoromethyl)-1H-pyrrole-2-carboxylic acid amide The desired compound was synthesized following general synthetic route 1 (see 01).

Example 57

1-Benzyl-3-(5-chloro-pyrimidin-2-yl)-N,4-dimethyl-N-[2-methyl-2-(methylcarbamoyl)-propyl]-5-(trifluoromethyl)-1H-pyrrole-2-carboxylic acid amide According to general procedure B [see 41g)] 1-benzyl-3-(5-chloropyrimidin-2-yl)-4-methyl-5-(trifluoromethyl)-1H-pyrrole-2-carboxylic acid [see 44b)] (120 mg, 0.303 mmol) was converted with N,2,2-trimethyl-3-(methylamino)propanamide hydrochloride [see section (B)] (82 mg, 0.455 mmol) to give desired 1-benzyl-3-(5-chloro-pyrimidin-2-yl)-N,4-dimethyl-N-[2-methyl-2-(methylcarbamoyl)-propyl]-5-(trifluoromethyl)-1H-pyrrole-2-carboxylic acid amide (40 mg, 25%).

Example 58

1-Benzyl-3-(5-chloro-pyrimidin-2-yl)-N-[2-(dimethyl-carbamoyl)-2-methyl-propyl]-N,4-dimethyl-5-(trifluoromethyl)-1H-pyrrole-2-carboxylic acid amide According to general procedure B [see 41g)] 1-benzyl-3-(5-chloropyrimidin-2-yl)-4-methyl-5-(trifluoromethyl)-1H-pyrrole-2-carboxylic acid [see 44b)] (120 mg, 0.303 mmol) was converted with N,N,2,2-tetramethyl-3-(methylamino)propanamide hydrochloride [see section (B)] (89 mg, 0.455 mmol) to give desired 1-benzyl-3-(5-chloro-pyrimidin-2-yl)-N-[2-(dimethyl-carbamoyl)-2-methyl-propyl]-N,4-dimethyl-5-(trifluoromethyl)-1H-pyrrole-2-carboxylic acid amide (25 mg, 15%).

General Synthetic Route 3:

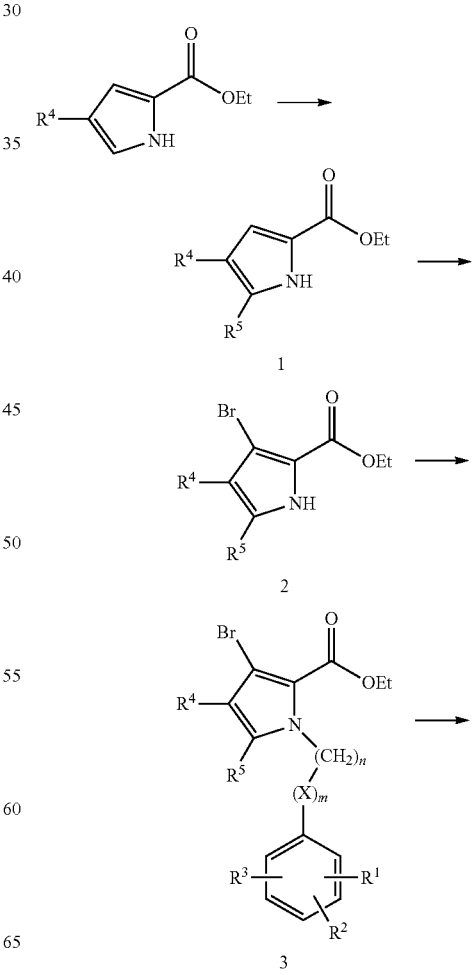

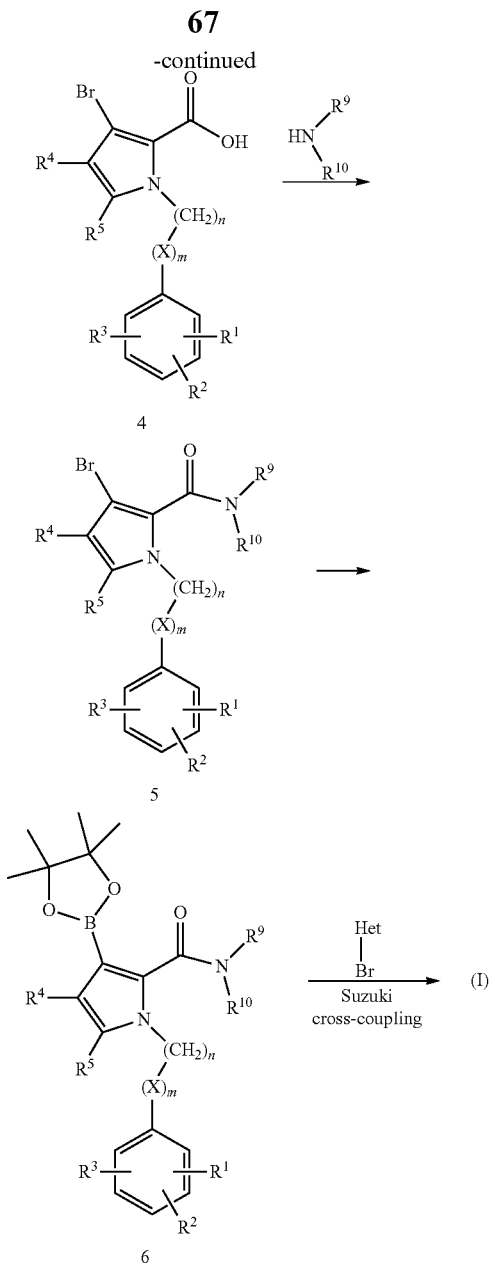

Example 55

1-Benzyl-3-(5-cyclopropyl-pyrazin-2-yl)-N-isopropyl-N,4-dimethyl-5-(trifluoromethyl)-1H-pyrrole-2-carboxylic acid amide 55a): Ethyl 4-methyl-5-(trifluoromethyl)-1H-pyrrole-2-carboxylate A solution of ethyl 4-methyl-1H-pyrrole-2-carboxylate (9.42 g, 61.5 mmol), $CF_3SO_2Cl$ (13.04 mL, 123 mmol) and $Fe_2SO_4.7H_2O$ (10.26 g, 36.9 mmol) in DMF (275 mL) was cooled to 0° C. Subsequently, 30% aqueous $H_2O_2$ (12.56 mL, 123 mmol) was added dropwise. Once effervescence had ceased the solution was stirred at RT for 1 h. The reaction mixture was poured out in ice cold $H_2O$ (1 L) while stirring. The solids were filtered off and the crude product was stored 5° C. for 6 d. The mixture was dissolved in DMF (275 mL). $Fe_2SO_4.7H_2O$ (10.26 g, 36.9 mmol) and $CF_3SO_2Cl$ (13.04 mL, 123 mmol) were added and the reaction mixture was stirred for 5 min, 30% aqueous $H_2O_2$ (12.56 mL, 123 mmol) was added dropwise to the solution which was then stirred for 1 h at 0° C. The reaction mixture was poured out in icecold $H_2O$ (500 mL). The white precipitate was filtered off, washed with ice cold $H_2O$ (2×25 mL). The residue was dissolved in EtOAc (200 mL) and washed with brine (2×100 mL). The organics were dried over $Na_2SO_4$ and the solvent was removed under reduced pressure to give 6.33 g (41%) of the desired product.

55b): Ethyl 3-bromo-4-methyl-5-(trifluoromethyl)-1H-pyrrole-2-carboxylate $K_2CO_3$ (3.96 g, 28.7 mmol) was added to a solution of ethyl 4-methyl-5-(trifluoromethyl)-1H-pyrrole-2-carboxylate (6.33 g, 25.2 mmol) in MeCN (125 mL). The reaction mixture was cooled to 0° C. NBS (5.09 g, 28.6 mmol) was added portionwise and the reaction mixture was stirred for 10 min. The reaction mixture was allowed to warm to RT. Ca. 40 mL of MeCN was removed under reduced pressure. $H_2O$ (170 mL) was added and the mixture was stirred for 45 min. The precipitate was filtered off, washed with $H_2O$ (2×100 mL) and dried on a glass filter for 1 h. The solids were dissolved in $Et_2O$ (200 mL), dried over $Na_2SO_4$ and concentrated under reduced pressure to give 6.26 g (83%) of the desired product.

55c): Ethyl 1-benzyl-3-bromo-4-methyl-5-(trifluoromethyl)-1H-pyrrole-2-carboxylate A suspension of ethyl 3-bromo-4-methyl-5-(trifluoromethyl)-1H-pyrrole-2-carboxylate (6.26 g, 20.86 mmol), $K_2CO_3$ (5.77 g, 41.7 mmol) and benzyl bromide (2.73 mL, 22.95 mmol) in MeCN (100 mL) was stirred at 80° C. for 2 h. Benzyl bromide (1.241 mL, 10.43 mmol) was added and the mixture was stirred for 1 h at 80° C. The reaction mixture was allowed to cool to RT and the solvents were removed under reduced pressure. The residue was partitioned between EtOAc (200 mL) and $H_2O$ (200 mL). The aqueous layer was extracted with EtOAc (2×200 mL) and the combined organics were dried over $Na_2SO_4$ and concentrated under reduced pressure. The crude product was coated onto silica and purified using flash cc (silica, gradient, heptane/$CH_2Cl_2$, 1:0→7:3) to give a pure and an impure batch. The impure batch was coated onto silica and purified further using flash cc (silica, gradient heptane/$CH_2Cl_2$, 1:0→7:3) to give a pure and an impure batch. The pure batches were combined to give 6.03 g (74%) of the desired product.

55d): 1-Benzyl-3-bromo-4-methyl-5-(trifluoromethyl)-1H-pyrrole-2-carboxylic acid NaOH (1.236 g, 30.9 mmol) was added to a cooled (0° C.) solution of ethyl 1-benzyl-3-bromo-4-methyl-5-(trifluoromethyl)-1H-pyrrole-2-carboxylate (6.03 g, 15.45 mmol) in DMSO (60 mL) while stirring. After 5 min, the reaction mixture was allowed to warm to RT. The flask was put in a water bath at 40° C. for a few seconds which made the mixture better stirrable. The reaction mixture was stirred for 18 h at RT. Aqueous 1M $KHSO_4$ (100 mL) was added and stirred for 5 min. The mixture was partitioned between brine (100 mL) and EtOAc (100 mL). The aqueous layer was diluted with $H_2O$ (50 mL) and extracted with EtOAc (2×100 mL). The combined organics were washed with brine (3×100 mL) and dried over $Na_2SO_4$ to give 5.43 g (97%) of the desired product.

55e): 1-Benzyl-3-bromo-N-isopropyl-N,4-dimethyl-5-(trifluoromethyl)-1H-pyrrole-2-carboxamide BOP-Cl (2.81 g, 11.05 mmol) was added to a solution of 1-benzyl-3-bromo-4-methyl-5-(trifluoromethyl)-1H-pyrrole-2-carboxylic acid (2 g, 5.52 mmol) and DIPEA (2.89 mL, 16.57 mmol) in DME (40 mL). The suspension was stirred for 5 min. N-methylpropan-2-amine (1.140 mL, 11.05 mmol) was added and the reaction mixture was stirred for 30 min. DIPEA (2.89 mL, 16.57 mmol) and BOP-Cl (2.81 g, 11.05 mmol) were added and the reaction mixture was stirred for 5 min. N-methylpropan-2-amine (1.140 mL, 11.05 mmol) was added and the reaction mixture was stirred for 30 min. BOP-Cl (1.406 g, 5.52 mmol) and DIPEA (0.965 mL, 5.52 mmol) were added and the reaction mixture was stirred for 5 min followed by the addition of N-methylpropan-2-amine (0.570 mL, 5.52 mmol). The reaction mixture was stirred for 30 min and quenched with a few drops of $H_2O$. The solvent was removed under reduced pressure and the residue was partitioned between half saturated aqueous $NaHCO_3$ (100 mL) and EtOAc (100 mL). The organic layer was washed with half saturated aqueous $NaHCO_3$ (100 mL) and brine (100 mL). The organic layer was separated and dried over $Na_2SO_4$. The solvent was removed under reduced pressure. The product was coated on silica and purified using flash cc (silica, gradient heptane/i-$Pr_2O$, 1:0→3:1) to give 2.27 g (89%) of the desired product.

55f): 1-Benzyl-N-isopropyl-N,4-dimethyl-3-(4,4,5,5-tetramethyl-1,3,2-dioxaborolan-2-yl)-5-(trifluoromethyl)-1H-pyrrole-2-carboxamide To a cooled (−78° C., acetone/dry ice) solution of 1-benzyl-3-bromo-N-isopropyl-N,4-dimethyl-5-(trifluoromethyl)-1H-pyrrole-2-carboxamide (500 mg, 1.078 mmol) in dry THF (5 mL) under Ar, 1.6 M n-BuLi in hexanes (0.9 mL, 1.440 mmol) was added. The mixture was stirred for 10 min, 4,4,5,5-tetramethyl-1,3,2-dioxaborolane (0.9 mL, 6.20 mmol) was added and the reaction mixture was stirred for 1.5 h at −78° C. The reaction mixture was quenched with half saturated aqueous $NH_4Cl$ (4 mL) and stored at −20 C. for 18 h. The reaction mixture was partitioned between $H_2O$ (100 mL) and EtOAc (100 mL). The organics were washed with brine (100 mL) and dried over $Na_2SO_4$. The solvent was removed under reduced pressure and diluted with DMSO (2 mL). The product was purified using reversed phase cc (C18, $H_2O$/MeCN/$HCO_2H$) to give 238 mg (47%) of the desired product.

55g): 1-Benzyl-3-(5-cyclopropyl-pyrazin-2-yl)-N-isopropyl-N,4-dimethyl-5-(trifluoromethyl)-1H-pyrrole-2-carboxylic acid amide According to general procedure E [described below] 1-benzyl-N-isopropyl-N,4-dimethyl-3-(4,4,5,5-tetramethyl-1,3,2-dioxaborolan-2-yl)-5-(trifluoromethyl)-1H-pyrrole-2-carboxamide (88 mg, 0.190 mmol) was converted with 2-bromo-5-cyclopropylpyrazine (57 mg, 0.284 mmol) to give desired 1-benzyl-3-(5-cyclopropyl-pyrazin-2-yl)-N-isopropyl-N,4-dimethyl-5-(trifluoromethyl)-1H-pyrrole-2-carboxylic acid amide (97 mg, 83%).

General Procedure E for Suzuki Cross Coupling:

$PdCl_2$(dppf) (0.1 eq) was added to a 30 min Ar degassed solution of the corresponding boronic ester (1 eq), the corresponding bromide (1.5 eq) and $Cs_2CO_3$ (3 eq) in DME:$H_2O$ (4:1). The vial was placed in a pre-heated oil bath at 100° C. and was stirred for 2-3 h under Ar. The reaction mixture was then filtered over silica. The filtrate was concentrated under reduced pressure and diluted with DCM. The crude product was purified using flash cc (silica).

Example 56

1-Benzyl-3-(5-cyclopropyl-pyrimidin-2-yl)-N-isopropyl-N,4-dimethyl-5-(trifluoromethyl)-1H-pyrrole-2-carboxylic acid amide According to general procedure E [see 55g)] 1-benzyl-N-isopropyl-N,4-dimethyl-3-(4,4,5,5-tetramethyl-1,3,2-dioxaborolan-2-yl)-5-(trifluoromethyl)-1H-pyrrole-2-carboxamide [see 55f)] (119 mg, 0.256 mmol) was converted with 2-chloro-5-cyclopropylpyrimidine (59 mg, 0.384 mmol) to give desired 1-benzyl-3-(5-cyclopropyl-pyrimidin-2-yl)-N-isopropyl-N,4-dimethyl-5-(trifluoromethyl)-1H-pyrrole-2-carboxylic acid amide (86 mg, 74%).

Example 59

1-Benzyl-N-isopropyl-N,4-dimethyl-3-(1-methyl-1H-imidazol-2-yl)-5-(trifluoromethyl)-1H-pyrrole-2-carboxamide The desired compound was synthesized following general synthetic route 1 (see 01).

Example 60

According to general procedure E [see 55g)] 1-benzyl-N-isopropyl-N,4-dimethyl-3-(4,4,5,5-tetramethyl-1,3,2-dioxaborolan-2-yl)-5-(trifluoromethyl)-1H-pyrrole-2-carboxamide [see 55f)] (315 mg, 0.678 mmol) was converted with 2-bromo-5-chloro-3-(methylsulfinyl)pyridine [see section B] (259 mg, 1.018 mmol) to give desired SC-60 (270 mg, 78%).

Example 61

According to general procedure E [see 55g)] 1-benzyl-N-isopropyl-N,4-dimethyl-3-(4,4,5,5-tetramethyl-1,3,2-dioxaborolan-2-yl)-5-(trifluoromethyl)-1H-pyrrole-2-carboxamide [see 55f)] (80 mg, 0.172 mmol) was converted with 2-bromo-5-(methylsulfinyl)pyridine (57 mg, 0.258 mmol) to give desired SC-61 (68 mg, 66%).

Section (B)
N,2,2-Trimethylpropan-1-amine hydrochloride

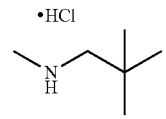

a): tert-Butyl neopentylcarbamate

To a solution of 2,2-dimethylpropan-1-amine (17.90 g, 205 mmol) in DCM (150 mL) was dropwise added a solution of $Boc_2O$ (44.8 g, 205 mmol) in DCM (50 mL) at 0° C. After complete addition, stirring was continued at RT overnight. The solvent was removed under reduced pressure and the residue co-evaporated with DCM (3×). EtOAc (250 mL) was added and the mixture was washed with $H_2O$ (2×250 mL). The organic layer was dried ($Na_2SO_4$) and evaporated under reduced pressure, to give 36.98 g (96%) of the desired product.

b): tert-Butyl methyl(neopentyl)carbamate

A solution of tert-butyl neopentylcarbamate (37.0 g, 198 mmol) in dry DMF (100 mL) was added to a suspension of 60% NaH in mineral oil (15.8 g, 395 mmol) in dry DMF (200 mL) under $N_2$ in 10 min and the reaction mixture was stirred for 1 h. To the reaction mixture was added MeI (30.9 mL, 494 mmol) in 10 min while cooling with an icebath and the reaction mixture was stirred at RT overnight. The reaction mixture was quenched with ice/$H_2O$ (600 mL) and extracted with $Et_2O$ (1 L). The organic layer was washed with brine, dried ($Na_2SO_4$) and concentrated to result in the desired product (45.6 g, '115%').

c): N,2,2-Trimethylpropan-1-amine hydrochloride

To a solution of tert-butyl methyl(neopentyl)carbamate (45.6 g, max. 198 mmol) in dry 1,4-dioxane (200 mL) was dropwise added 4M HCl in dioxane (200 mL, 800 mmol) and the reaction mixture was stirred overnight. The reaction mixture was concentrated and stirred in $Et_2O$ for 1 d. The product was filtered under $N_2$ stream, washed with a small amount of $Et_2O$ (2×) and dried on filter for 10 min yielding the desired product (26.0 g, 95% over two steps).

2,2-Dimethyl-3-(methylamino)propanamide hydrochloride

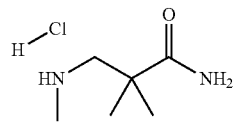

a): Ethyl 3-((tert-butoxycarbonyl)amino)-2,2-dimethylpropanoate

At 0° C., ethyl 3-amino-2,2-dimethylpropanoate hydrochloride (4.5 g, 24.77 mmol) was dissolved in a mixture of DCM (150 mL) and pentane (150 mL). $Et_3N$ (4.14 mL, 29.7 mmol) was added, followed by $Boc_2O$ (5.41 g, 24.77 mmol) and the white suspension was stirred at RT for 20 h. The reaction mixture was concentrated in vacuo and the residue was partitioned between $H_2O$ (100 mL) and i-$Pr_2O$ (100 mL). The aqueous layer was extracted with i-$Pr_2O$ (100 mL) and the combined organic layers were washed with $H_2O$ (2×50 mL) and brine (2×50 mL) before drying on $Na_2SO_4$ and concentration in vacuo to give the desired product (6.05 g, 100%) as a yellow oil.

b): Ethyl 3-((tert-butoxycarbonyl)(methyl)amino)-2,2-dimethylpropanoate

To a cooled (0° C.) solution of ethyl 3-((tert-butoxycarbonyl)amino)-2,2-dimethylpropanoate (6.05 g, 24.66 mmol) in dry DMF (40 mL) was added 60% NaH in mineral oil (1.085 g, 27.1 mmol). The mixture was stirred for 5 min at 0° C., then warmed up to RT over 15 min. The mixture was cooled to 0° C. again and MeI (3.1 mL, 49.6 mmol) was added via a syringe over 2 min. The mixture was stirred at RT for 3 h. The reaction mixture was poured out in aqueous 1M $KHSO_4$ (100 mL) with vigorous stirring and the product was extracted with i-$Pr_2O$/EtOAc (1:1, v/v, 250 mL). The organic layer was washed with aqueous 1M $KHSO_4$ (2×50 mL), saturated aqueous $NaHCO_3$ (2×50 mL) and aqueous 1M $Na_2S_2O_3$ (2×50 mL) before washing with brine (2×50 mL) and drying on $Na_2SO_4$. The solvent was removed in vacuo to give the desired product (5.72 g, 89%) as a colorless oil.

c): 3-((tert-Butoxycarbonyl)(methyl)amino)-2,2-dimethylpropanoic acid

A suspension of LiOH.$H_2O$ (9 g, 216 mmol) in $H_2O$ (25 mL) was added to a solution of ethyl 3-((tert-butoxycarbonyl)(methyl)amino)-2,2-dimethylpropanoate (5.6 g, 21.59 mmol) in a mixture of THF (25 mL) and EtOH (25 mL). The mixture was stirred at 60° C. for 3 h. The volatiles were removed in vacuo and the aqueous mixture was cooled in an ice bath. Aqueous 1M $KHSO_4$ (250 mL) was added. The product was extracted with EtOAc (3×75 mL) and the combined organic layers were washed with aqueous 1M $KHSO_4$ (2×50 mL) and brine (2×50 mL) before drying on $Na_2SO_4$ and concentration in vacuo to give the desired product (4.9 g, 98%) as a yellow oil which crystallised on standing.

d): tert-Butyl (3-amino-2,2-dimethyl-3-oxopropyl)(methyl)carbamate

To a solution of 3-((tert-butoxycarbonyl)(methyl)amino)-2,2-dimethylpropanoic acid (4.22 g, 18.25 mmol) in EtOAc (200 mL) was added CDI (3.55 g, 21.89 mmol). The mixture was stirred at RT for 1.5 h. The reaction mixture was cooled in an ice bath and aqueous 25% $NH_4OH$ (34 mL, 219 mmol) was added and the resulting suspension was stirred at RT for 2 h. The reaction mixture was concentrated in vacuo to approximately 200 mL. The residue was washed with saturated aqueous $NaHCO_3$ (3×50 mL), aqueous 1M $KHSO_4$ (2×50 mL) and brine (2×50 mL) before drying on $Na_2SO_4$ and concentration in vacuo to give a white solid. The product was crystallised from hot EtOH and dried on air to give the desired product (2.8 g, 66%) as colorless crystals.

e): 2,2-Dimethyl-3-(methylamino)propanamide hydrochloride

To a solution of tert-butyl (3-amino-2,2-dimethyl-3-oxopropyl)(methyl)carbamate (1.8 g, 7.82 mmol) in DCM (40 mL) was added 4 M HCl in dioxane (39 mL, 156 mmol). The mixture was stirred at RT for 3 h. The reaction mixture was concentrated in vacuo to give the desired product (1.27 g, 98%) as a white solid.

2,2-Dimethyl-3-(methylamino)propanenitrile hydrochloride

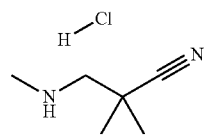

a): tert-Butyl (2-cyano-2-methylpropyl)(methyl)carbamate

A solution of tert-butyl (3-amino-2,2-dimethyl-3-oxopropyl)(methyl)carbamate [see step d) synthesis of 2,2-dimethyl-3-(methylamino)propanamide hydrochloride] (1 g, 4.34 mmol) in pyridine (10 mL) was cooled in an ice bath. POCl$_3$ (405 µL, 4.34 mmol) was added via a syringe and the resulting white suspension was stirred at 0° C. for 30 min. The reaction mixture was poured out in aqueous 5M HCl (26 mL) and the product was extracted with EtOAc (1×50 mL, 1×25 mL). The combined organic layers were washed with aqueous 1M HCl (2×20 mL), saturated aqueous NaHCO$_3$ (2×20 mL) and brine (2×20 mL) before drying on Na$_2$SO$_4$ and concentration in vacuo to give the desired product (689 mg, 74%) as a colorless oil.

b): 2,2-Dimethyl-3-(methylamino)propanenitrile hydrochloride

To a solution of tert-butyl (2-cyano-2-methylpropyl)(methyl)carbamate (0.689 g, 3.25 mmol) in DCM (16 mL) was added 4M HCl in dioxane (16.2 mL, 64.9 mmol) and the solution was stirred at RT for 1 h. The reaction mixture was concentrated in vacuo to give a white solid. The product was crystallised from hot EtOH to give the desired product (287 mg, 59%) as colorless crystals.

N,2,2-Trimethyl-3-(methylamino)propanamide hydrochloride

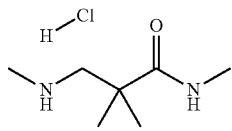

a): Ethyl 3-((tert-butoxycarbonyl)amino)-2,2-dimethylpropanoate

To a cooled solution of 3-((tert-butoxycarbonyl)(methyl)amino)-2,2-dimethylpropanoic acid [see above] (4.98 g, 27.4 mmol) and Et$_3$N (4.59 mL, 32.9 mmol) in DCM (200 mL) was added Boc$_2$O (5.98 g, 27.4 mmol) under N$_2$. The mixture was stirred at RT for 1 h. The reaction mixture was concentrated in vacuo and the residue was suspended in i-Pr$_2$O (100 mL) and filtered off. The residue was washed with i-Pr$_2$O (2×25 mL) and the filtrate was washed with brine/H$_2$O (1:1, 2×20 mL) and brine (2×20 mL) before drying on Na$_2$SO$_4$ and concentration in vacuo to give the desired product (6.23 g, 93%).

b): Ethyl 3-((tert-butoxycarbonyl)(methyl)amino)-2,2-dimethylpropanoate and Methyl 3-((tert-butoxycarbonyl)(methyl)amino)-2,2-dimethylpropanoate To a cooled solution of ethyl 3-((tert-butoxycarbonyl)amino)-2,2-dimethylpropanoate (6.23 g, 25.4 mmol) in dry DMF (40 mL) was added NaH; 60 wt % in mineral oil (7 g, 175 mmol). The white suspension was warmed to RT over 45 min. The mixture was cooled to 0° C. and MeI (3.16 mL, 50.8 mmol) was added. The mixture was stirred at 0° C. for 30 min. The mixture was warmed to RT and stirred for 2 h. The mixture was very carefully poured out in a cooled solution of aqueous 1 M KHSO$_4$ (150 mL) in ice water (150 mL) under a fast stream of N$_2$. The product was extracted with i-Pr$_2$O (200 mL) and EtOAc (200 mL) and the combined organic layers were washed with aqueous 1 M KHSO$_4$ (2×50 mL), aqueous saturated NaHCO$_3$ (2×50 mL) and brine (2×50 mL) before drying on Na$_2$SO$_4$ and concentration in vacuo. At 0° C., the product was dissolved in dry DMF (40 mL) and NaH; 60 wt % in mineral oil (0.508 g, 12.70 mmol) was added. The mixture was stirred for 30 min. MeI (0.79 mL, 12.70 mmol) was added and the stirring was continued at RT for 3 h. The mixture was poured out in aqueous 1 M KHSO$_4$ (15 mL) and the product was extracted with i-Pr$_2$O/EtOAc (1:1, 2×100 mL). The combined organic layers were washed with aqueous 1 M KHSO$_4$ (2×20 mL), aqueous saturated NaHCO$_3$ (2×20 mL) and brine (2×20 mL) before drying on Na$_2$SO$_4$ and concentration in vacuo. The product was purified using flash cc (silica, heptane/EtOAc 1:0→6:4) to give a mixture of the desired products (5.2 g, 80%).

c): 3-((tert-Butoxycarbonyl)(methyl)amino)-2,2-dimethylpropanoic acid

To a solution of ethyl 3-((tert-butoxycarbonyl)(methyl)amino)-2,2-dimethylpropanoate (5.21 g, 12.46 mmol, 62%) and methyl 3-((tert-butoxycarbonyl)(methyl)amino)-2,2-dimethylpropanoate (5.21 g, 8.07 mmol, 38%) in THF/EtOH (1:1, 50 mL) was added LiOH.H$_2$O (8.39 g, 200 mmol) and H$_2$O (25 mL). The solution was heated to 60° C. for 1.5 h. The heating was continued at 70° C. for 1 h. The volatiles were removed in vacuo. The residue was cooled in an ice bath and acidified using aqueous 1 M KHSO$_4$ (200 mL). The product was extracted with EtOAc (2×100 mL) and the combined organic layers were washed with aqueous 1 M KHSO$_4$ (2×20 mL) and brine (2×20 mL) before drying on Na$_2$SO$_4$ and concentration in vacuo to give the desired product (4.57 g, 96%).

d): tert-Butyl (2,2-dimethyl-3-(methylamino)-3-oxopropyl)(methyl)carbamate

To a solution of 3-((tert-butoxycarbonyl)(methyl)amino)-2,2-dimethylpropanoic acid (1.0 g, 4.32 mmol) and BOP-Cl (1.321 g, 5.19 mmol) in dry DME (10 mL) was added DIPEA (0.995 mL, 5.62 mmol) and the resulting white suspension was stirred at RT for 5 min. MeNH$_2$.HCl (0.438 g, 6.49 mmol) was added, followed by DiPEA (1.531 mL, 8.65 mmol) and the suspension was stirred RT for 30 min. More MeNH$_2$—HCl (0.584 g, 8.65 mmol) and DiPEA (1.53 mL, 8.65 mmol) were added and the stirring was continued at RT for 20 h. More DIPEA (1.15 mL, 6.49 mmol) and MeNH$_2$.HCl (438 mg, 6.49 mmol) were added and the stirring was continued at RT for 1 h. The reaction mixture was poured out in aqueous 1 M KHSO$_4$ (50 mL) and the product was extracted with EtOAc (2×50 mL). The combined organic layers were washed with aqueous 1 M KHSO$_4$ (2×20 mL), aqueous saturated NaHCO$_3$ (2×20 mL) and brine (2×20 mL) before drying on Na$_2$SO$_4$ and concentration in vacuo to give the desired product (823 mg, 78%).

e): N,2,2-Trimethyl-3-(methylamino)propanamide hydrochloride

At RT, 4 M HCl in dioxane (16.84 mL, 67.4 mmol) was slowly added to a solution of tert-butyl (2,2-dimethyl-3-(methylamino)-3-oxopropyl)(methyl)carbamate (0.823 g, 3.37 mmol) in DCM (17 mL). The mixture was stirred at RT

N,2,2-Trimethyl-3-(methylamino)propanamide hydrochloride

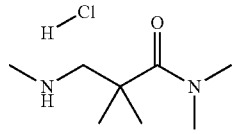

a): tert-Butyl (3-(dimethylamino)-2,2-dimethyl-3-oxopropyl)(methyl)carbamate To a solution of 3-((tert-butoxycarbonyl)(methyl)amino)-2,2-dimethylpropanoic acid [see above] (1.0 g, 4.32 mmol) in dry DME (15 mL) was added BOP-Cl (1.321 g, 5.19 mmol), followed by dimethylamine; 2 M in THF (7.8 mL, 15.60 mmol) and the reaction mixture was stirred at RT for 3 h. More dimethylamine; 2 M in THF (1 mL, 2 mmol) was added and the stirring was continued for 20 h. The reaction mixture was poured out in aqueous 1 M $KHSO_4$ (20 mL) and the product was extracted with i-$Pr_2O$ (2×50 mL). The combined organic layers were washed with aqueous 1 M $KHSO_4$ (2×25 mL), aqueous 1 M NaOH (2×25 mL) and brine (2×25 mL) before drying on $Na_2SO_4$ and concentration in vacuo to give the desired product (764 mg, 68%).

b): N,2,2-Trimethyl-3-(methylamino)propanamide hydrochloride

To a solution of tert-butyl (3-(dimethylamino)-2,2-dimethyl-3-oxopropyl)(methyl)carbamate (0.764 g, 2.96 mmol) in DCM (17 mL) was added 4 M HCl in dioxane (14.79 mL, 59.1 mmol) and the reaction mixture was stirred at RT for 1 h. The reaction mixture was concentrated in vacuo to give the desired product (670 mg, '116%').

for 3 h. The reaction mixture was concentrated in vacuo to give the desired product (642 mg, '105%').

2-Bromo-5-chloro-3-(methylsulfinyl)pyridine

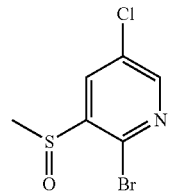

b): 2-Bromo-5-chloro-3-(methylsulfinyl)pyridine

Aqueous 30% $H_2O_2$ (0.257 mL, 2.52 mmol) was added to a solution of 2-bromo-5-chloro-3-(methylthio)pyridine (500 mg, 2.096 mmol) in 1,1,1,3,3,3-hexafluoro-2-propanol (5 mL). The reaction mixture was stirred for 18 h at RT. The reaction was quenched with aqueous 1 M $Na_2S_2O_3$ (3 mL, 3 mmol) and the solvent was removed under reduced pressure. The residue was co-evaporated with EtOH (30 mL). The product was taken up in EtOAc (30 mL), filtered over cotton wool and the filtrate was evaporated. The product was coated on silica and purified using flash cc (silica, gradient heptane/EtOAc, 1:0→1:1) to afford 481 mg (90%) of the desired product.

Analytical Data:

Material and Methods for LC/MS Analytics: Hardware: Coupled Agilent 1290 Infinity UHPLC-TOF System; LC-Module: MTP-Handler: Agilent, Model BenchCel 2R; Themostatic Control Autoinjector: Agilent, Modell G4226A; Column oven: Agilent, Model G1316C; DAD: Agilent, Model G4212A; Binary Pump: Agilent, Model G4220A; Time Of Fliqht Mass Spectrometer: Agilent 6224; Ion source: Dual ESI; Column: Supplier: Waters; Type: Acquity UPLC HSS T3 1.8 µm (Part No. 186003538); Dimensions: 2.1×50 mm; Eluents: Eluent A: Water from Millipore Ultra-pure water System: Milli-Q Integral 3+0.1% Formic acid; Eluent B: MeCN, Merck KGaA: LiChrosolv Hypergrade for LC-MS (1.00029.9010)+0.1% Formic acid; Formic acid: Merck KGaA: Suprapure 98-100% (1.11670.1000); LC-Method: Flow: 2.5 mL/min; Runtime: 1.2 min; Gradient: Start 2% B, 1 min 100% B, 1.09 min 100% B, 1.11 min 2% B, 1.2 min 2% B Stop; Column temperature: 80° C.; UV: 190-400 nm; MS-Method: Ion Polarity: Positive; Gas Temperature: 325° C.; Gas Flow: 10 mL/min

| Ex. No. | $R^1, R^2, R^3$ | m, n | $R^4$ | $R^5$ | Het | $N(R^9)(R^{10})$ | Mass | Mass Found | UV254-purity |
|---|---|---|---|---|---|---|---|---|---|
| 01 | H, H, H | 0, 1 | $CF_3$ | $CH_3$ | pyrazine-OCH₃ | neopentyl-N | 474.52 | Yes | 100 |
| 02 | H, H, H | 0, 1 | $CF_3$ | $CH_3$ | pyridine-OCH₃ | neopentyl-N | 473.53 | Yes | 100 |
| 03 | H, H, H | 0, 1 | $CF_3$ | $CH_3$ | pyridine-OH | neopentyl-N | 459.50 | Yes | 100 |

| Ex. No. | R¹, R², R³ | m, n | R⁴ | R⁵ | Het | N(R⁹)(R¹⁰) | Mass | Mass Found | UV254-purity |
|---|---|---|---|---|---|---|---|---|---|
| 04 | H, H, H | 0, 1 | CF$_3$ | CH$_3$ | 1-methyl-pyrazol-4-yl | N-methyl-neopentylamine | 446.51 | Yes | 94 |
| 05 | H, H, H | 0, 1 | CF$_3$ | CH$_3$ | 3-methoxy-pyrazin-5-yl | morpholino | 460.45 | Yes | 100 |
| 06 | H, H, H | 0, 1 | CF$_3$ | CH$_3$ | 2-methoxy-pyridin-5-yl | morpholino | 459.46 | Yes | 98 |
| 07 | H, H, H | 0, 1 | CF$_3$ | CH$_3$ | 2-hydroxy-pyridin-5-yl | morpholino | 445.43 | Yes | 100 |
| 08 | H, H, H | 0, 1 | CF$_3$ | CH$_3$ | 1-methyl-pyrazol-4-yl | morpholino | 432.44 | Yes | 99 |
| 09 | H, H, H | 0, 1 | CF$_3$ | CH$_3$ | 1H-pyrazol-4-yl | N-methyl-neopentylamine | 432.48 | Yes | 95 |
| 10 | H, H, H | 0, 1 | CF$_3$ | CH$_3$ | 1H-pyrazol-4-yl | morpholino | 418.41 | Yes | 96 |
| 11 | H, H, H | 0, 1 | CF$_3$ | CH$_3$ | pyrimidin-5-yl | N-methyl-neopentylamine | 444.49 | Yes | 94 |
| 12 | H, H, H | 0, 1 | CF$_3$ | CH$_3$ | 2-methoxy-pyrimidin-5-yl | N-methyl-neopentylamine | 474.52 | Yes | 96 |
| 13 | H, H, H | 0, 1 | CF$_3$ | CH$_3$ | 5-chloro-thiophen-2-yl | N-methyl-neopentylamine | 482.99 | Yes | 100 |
| 14 | H, H, H | 0, 1 | CF$_3$ | CH$_3$ | 2-methoxy-pyrimidin-5-yl | morpholino | 460.45 | Yes | 100 |
| 15 | H, H, H | 0, 1 | CF$_3$ | CH$_3$ | pyrimidin-5-yl | morpholino | 430.42 | Yes | 100 |
| 16 | H, H, H | 0, 1 | CF$_3$ | CH$_3$ | 3,5-dimethyl-isoxazol-4-yl | N-methyl-neopentylamine | 461.52 | Yes | 98 |

-continued

| Ex. No. | R¹, R², R³ | m, n | R⁴ | R⁵ | Het | N(R⁹)(R¹⁰) | Mass | Mass Found | UV254-purity |
|---|---|---|---|---|---|---|---|---|---|
| 17 | H, H, H | 0, 1 | CF₃ | CH₃ | 3-F, 5-CF₃ pyridin-2-yl | N-methyl-neopentyl | 529.49 | Yes | 100 |
| 18 | H, H, H | 0, 1 | CF₃ | CH₃ | 5-Cl-pyrimidin-2-yl | N-methyl-neopentyl | 478.94 | Yes | 100 |
| 19 | H, H, H | 0, 1 | CF₃ | CH₃ | 6-CN-pyridin-3-yl | N-methyl-neopentyl | 482.54 | Yes | 100 |
| 20 | H, H, H | 0, 1 | CF₃ | CH₃ | 6-Cl-pyridin-3-yl | N-methyl-neopentyl | 491.98 | Yes | 100 |
| 21 | H, H, H | 0, 1 | CF₃ | CH₃ | 6-OCH₃-pyridin-3-yl | N-methyl-neopentyl | 487.56 | Yes | 100 |
| 22 | H, H, H | 0, 1 | CF₃ | CH₃ | 6-Cl-pyridazin-3-yl | N-methyl-neopentyl | 478.94 | Yes | 100 |
| 23 | H, H, H | 0, 1 | CF₃ | CH₃ | 3,5-dimethyl-isoxazol-4-yl | morpholino | 447.45 | Yes | 100 |
| 24 | H, H, H | 0, 1 | CF₃ | CH₃ | 3-F, 5-CF₃ pyridin-2-yl | morpholino | 515.42 | Yes | 100 |
| 25 | H, H, H | 0, 1 | CF₃ | CH₃ | 5-Cl-pyrimidin-2-yl | morpholino | 464.87 | Yes | 99 |
| 26 | H, H, H | 0, 1 | CF₃ | CH₃ | 6-CN-pyridin-3-yl | morpholino | 468.47 | Yes | 100 |
| 27 | H, H, H | 0, 1 | CF₃ | CH₃ | 6-Cl-pyridin-3-yl | morpholino | 477.91 | Yes | 100 |

| Ex. No. | R¹, R², R³ | m, n | R⁴ | R⁵ | Het | N(R⁹)(R¹⁰) | Mass | Mass Found | UV254-purity |
|---|---|---|---|---|---|---|---|---|---|
| 28 | H, H, H | 0, 1 | CF$_3$ | CH$_3$ | 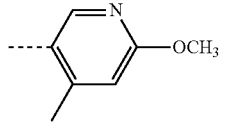 |  | 473.49 | Yes | 100 |
| 29 | H, H, H | 0, 1 | CF$_3$ | CH$_3$ | 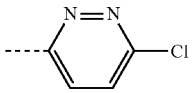 | 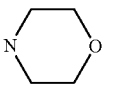 | 464.87 | Yes | 97 |
| 30 | H, H, H | 0, 1 | CF$_3$ | CH$_3$ | 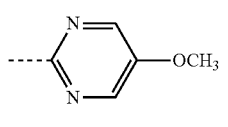 | 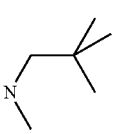 | 474.52 | Yes | 98 |
| 31 | H, H, H | 0, 1 | CF$_3$ | CH$_3$ | 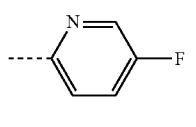 | 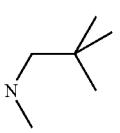 | 461.50 | Yes | 98 |
| 32 | H, H, H | 0, 1 | CF$_3$ | CH$_3$ | 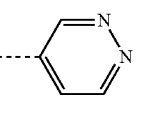 | 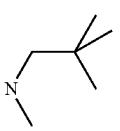 | 444.49 | Yes | 97 |
| 33 | H, H, H | 0, 1 | CF$_3$ | CH$_3$ | 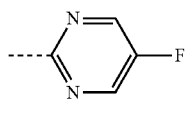 | 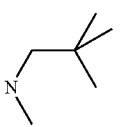 | 462.48 | Yes | 98 |
| 34 | H, H, H | 0, 1 | CF$_3$ | CH$_3$ | 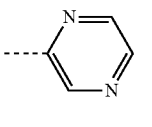 | 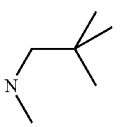 | 444.49 | Yes | 97 |
| 35 | H, H, H | 0, 1 | CF$_3$ | CH$_3$ | 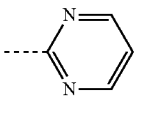 | 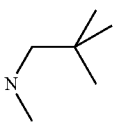 | 444.49 | Yes | 98 |
| 36 | H, H, H | 0, 1 | CF$_3$ | CH$_3$ | 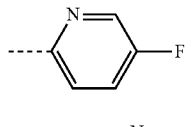 | 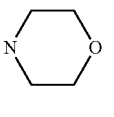 | 447.43 | Yes | 98 |
| 37 | H, H, H | 0, 1 | CF$_3$ | CH$_3$ | 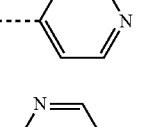 | 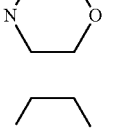 | 430.42 | Yes | 97 |
| 38 | H, H, H | 0, 1 | CF$_3$ | CH$_3$ | 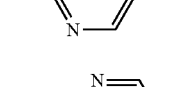 | 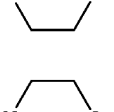 | 448.41 | Yes | 98 |
| 39 | H, H, H | 0, 1 | CF$_3$ | CH$_3$ | 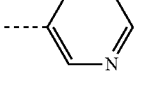 | 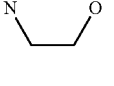 | 430.42 | Yes | 97 |

-continued
| Ex. No. | R¹, R², R³ | m, n | R⁴ | R⁵ | Het | N(R⁹)(R¹⁰) | Mass | Mass Found | UV254-purity |
|---|---|---|---|---|---|---|---|---|---|
| 40 | H, H, H | 0, 1 | CF₃ | CH₃ | 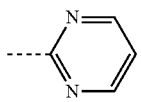 | 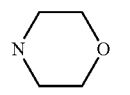 | 430.42 | Yes | 98 |
| 41 | H, H, H | 0, 1 | CF₃ | CH₃ | 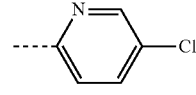 | 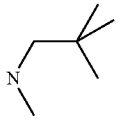 | 477.95 | Yes | 100 |
| 42 | H, H, H | 0, 1 | CF₃ | CH₃ | 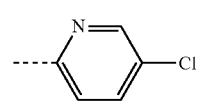 | 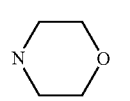 | 463.88 | Yes | 96 |
| 43 | H, H, H | 0, 1 | CF₃ | CH₃ | 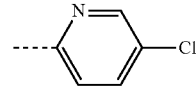 | 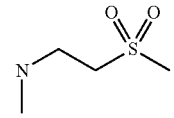 | 513.96 | Yes | 99 |
| 44 | H, H, H | 0, 1 | CF₃ | CH₃ | 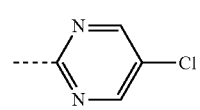 | 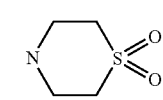 | 512.93 | Yes | 100 |
| 45 | H, H, H | 0, 1 | CF₃ | CH₃ | 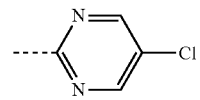 | 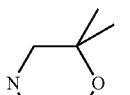 | 492.92 | Yes | 100 |
| 46 | H, H, H | 0, 1 | CF₃ | CH₃ | 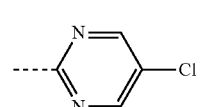 | 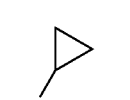 | 434.84 | Yes | 100 |
| 47 | H, H, H | 0, 1 | CF₃ | CH₃ | 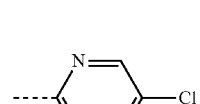 | 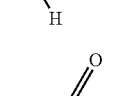 | 477.87 | Yes | 98 |
| 48 | H, H, H | 0, 1 | CF₃ | CH₃ | 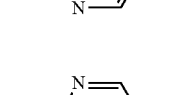 | 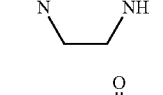 | 507.94 | Yes | 98 |
| 49 | H, H, H | 0, 1 | CF₃ | CH₃ | 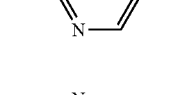 |  | 489.92 | Yes | 100 |
| 50 | H, H, H | 0, 1 | CF₃ | CH₃ | 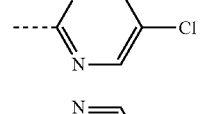 |  | 449.90 | Yes | 100 |
| 51 | H, H, H | 0, 1 | CF₃ | CH₃ | 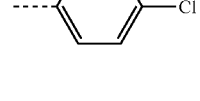 | 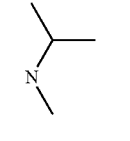 | 418.46 | Yes | 97 |

-continued

| Ex. No. | R¹, R², R³ | m, n | R⁴ | R⁵ | Het | N(R⁹)(R¹⁰) | Mass | Mass Found | UV254-purity |
|---|---|---|---|---|---|---|---|---|---|
| 52 | H, H, H | 0, 1 | CF₃ | CH₃ | pyrimidine-Cl | isopropyl-NH | 436.86 | Yes | 98 |
| 53 | H, H, H | 0, 1 | CF₃ | CH₃ | pyridine-Cl | isopropyl-NH | 435.87 | Yes | 100 |
| 54 | H, H, H | 0, 1 | CF₃ | CH₃ | pyrimidine-Cl | N(iPr)(Me) | 450.88 | Yes | 93 |
| 55 | H, H, H | 0, 1 | CF₃ | CH₃ | pyrazine-cyclopropyl | N(iPr)(Me) | 456.50 | Yes | 100 |
| 56 | H, H, H | 0, 1 | CF₃ | CH₃ | pyrimidine-cyclopropyl | N(iPr)(Me) | 456.50 | Yes | 100 |
| 57 | H, H, H | 0, 1 | CF₃ | CH₃ | pyrimidine-Cl | CH₂C(Me)₂C(O)NHMe, NMe | 521.96 | Yes | 100 |
| 58 | H, H, H | 0, 1 | CF₃ | CH₃ | pyrimidine-Cl | CH₂C(Me)₂C(O)NMe₂, NMe | 535.99 | Yes | 100 |
| 59 | H, H, H | 0, 1 | CF₃ | CH₃ | N-methylimidazole | N(iPr)(Me) | 418.20 | Yes | >98 |
| 60 | H, H, H | 0, 1 | CF₃ | CH₃ | pyridine-S(O)Me | N(iPr)(Me) | 477.17 | Yes | >98 |
| 61 | H, H, H | 0, 1 | CF₃ | CH₃ | pyridine-S(O)Me-Cl | N(iPr)(Me) | 511.13 | Yes | |

2. Assay Descriptions and Biological Data:

2.1 Fluorescent Assay for CaV2.2 Channels Using Potassium Depolarization to Induce Channel Opening Human CaV2.2 channels were stably expressed in HEK293 cells together with alpha2-delta and beta subunits of voltage gated calcium channels. In addition, an inwardly rectifying potassium channel (Kir2.3) was stably expressed in these cells to augment control of the cell membrane potential by the concentration of extracellular potassium ions. Raise of the extracellular potassium concentration leads to depolarization of the membrane potential and thus regulates the voltage dependent state of CaV2.2 channels.

For preparation, cells were seeded in black poly-D-lysine coated 96-well plates (Becton Dickinson, Biocoat 4640) in 100 µL medium [500 mL DMEM/F-12 plus Glutamax (Invitrogen 31331-093) plus 5.5 mL MEM NEAA 100× (Invitrogen 11140-035) plus 50 mL FBS decomplemented (Invitrogen 10270-106) plus 200 µg/mL Geneticin (Invitrogen 10131-027) plus 50 µg/mL Hygromycin B (Invitrogen 10687-010) plus 2 µg/mL Blasticidin (anti-bl5b Invivo-Gen) plus 0.2 µg/mL Puromycin (A 11138-03)] at a cell density of 30.000 cells per well. Plates were incubated at 37° C. (5% $CO_2$) for 20 to 23 h. On the day of experiment medium was discarded and cells were loaded with Fluo 4 by addition of 100 µL of basic assay buffer (10 mM HEPES, 1 mM KCl, 149 mM NaCl, 0.8 mM $CaC_2$, 1.7 mM $MgCl_2$, 10 mM Glucose, 0.1% BSA. pH 7.4) containing 2 µM Fluo 4 (Molecular Probes; F-14201), 0.01% pluronic acid (Molecular Probes; P-6866) and 2.5 mM probenecid (Molecular Probes; P36400). Cells were incubated in the dark at 25° C. for 60 min. Then dye containing buffer was discarded and 100 µL basic (1 mM KCl) or alternative (30 mM KCl) assay buffer was added. The alternative assay buffer contained altered concentrations of KCl (30 mM) and NaCl (120 mM) and was used in order to promote the inactivated channel state. After that 25 µL of basic or alternative assay buffer with or without test compound were added and cells were incubated again in the dark at 25° C. for 15 min. Fluorescence intensity was measured on a FLIPR 3 instrument (Molecular Devices Corp., Sunnyvale, Calif.) with excitation at 480 nm and emission at 535 nm. After continuously reading fluorescence for 30 sec, 50 µL of basic assay buffer containing 210 mM KCl (NaCl omitted) were added for depolarization. Peak fluorescent signal intensity was determined and the amplitude of the peak signal, normalized to base line, was used to measure channel inhibition by test compounds.

The following table summarizes the inhibitory activity of exemplified compounds according to the present invention.

| Example No. | Activity * |
|---|---|
| 01 | B |
| 02 | C |
| 03 | C |
| 04 | A |
| 05 | C |
| 06 | B |
| 08 | C |
| 09 | B |
| 10 | C |
| 11 | B |
| 12 | B |
| 13 | B |
| 14 | C |
| 15 | C |
| 16 | B |
| 17 | B |
| 18 | A |
| 19 | B |
| 20 | B |
| 21 | B |
| 22 | A |
| 23 | B |
| 24 | A |
| 25 | A |
| 26 | B |
| 27 | B |
| 28 | B |
| 29 | C |
| 30 | B |
| 31 | A |
| 32 | B |
| 33 | A |
| 34 | B |
| 35 | B |
| 36 | B |
| 37 | C |
| 38 | C |
| 39 | C |
| 40 | C |
| 41 | A |
| 42 | A |
| 43 | A |
| 44 | B |
| 45 | A |
| 46 | C |
| 47 | C |
| 48 | A |
| 49 | A |
| 50 | A |
| 51 | B |
| 52 | C |
| 53 | B |
| 54 | A |
| 56 | A |
| 58 | A |
| 61 | B |

* %-Inhib (CaV2.2) @3 µM @30 mM KCl: "A": %-Inhibition >95%; "B": %-Inhibition >75% up to ≤95%; "C": %-Inhibition >40% up to ≤75%, "D": %-Inhibition >30% up to ≤40%.

2.2 Electrophysiological Assessment of Calcium Channel Activity

Patch-clamp recordings were performed using HEK293 cells stably expressing human Cav2.2. Cells were plated in T150 flasks and grown a humidified incubator at 37° C. and under 5% $CO_2$ to approximately 50-60% confluency. Cells were maintained at 30° C. for 48 hrs prior to recording. On the day of the experiment, cells were harvested with TrypLE cell detachment solution (Invitrogen) diluted to 25% with phosphate buffered saline and maintained in 50% cell culture media, 50% NaCl based external saline (in mM, 140 NaCl, 4 KCl, 1 $MgCl_2$, 2 $CaCl_2$, 5 Glucose, 10 HEPES, pH 7.4) up to several hours prior to experiment.

Currents were recorded at room temperature (21-23° C.) using the Patchliner planar array technology (Nanion). Patchliner is a multi-well whole-cell automated patch clamp device that operates asynchronously with fully integrated fluidics. Capacitance and series resistance compensation was automated and no correction for liquid junction potential was employed. Leak was subtracted on-line. Whole-cell patch-clamp recordings were obtained using extracellular saline consisting of (mM): 145 TEA-Cl, 10 $BaCl_2$, 10 HEPES, 10 Glucose. The pH was adjusted to 7.35 with NaOH and the osmolarity was adjusted to 310 mOsm with sucrose. Intracellular solution consisted of (mM): 50 CsCl, 60 CsF, 10 NaCl, 20 EGTA, 5 BAPTA, 10 HEPES. Prior to an experiment, 5 mM MgATP and 0.3 NaGTP were added, the pH was adjusted to 7.2 with CsOH and the osmolarity was adjusted to 290 mOsm with sucrose.

A voltage pulse protocol was utilised to assess compound inhibition. Cells were held at a holding potential of −60 mV and channels were activated using a 10 ms test pulse to +30 mV activated every 10 seconds (0.1 Hz). Increasing concentrations of compound were applied to individual cells with 5 minutes at each test concentration. Compounds were prepared in DMSO as 10 mM stock solutions and subsequent 1:3 serial dilutions performed. Final dilution 1:1000 in external solution resulted in a final DMSO concentration of 0.1%. For each cell, current responses were normalised to dimethyl sulfoxide vehicle control to generate concentration-response curves. When multiple doses were achieved per cell, IC50 values were calculated from the fits of the Hill equation to the data. The form of the Hill equation used was: Relative current=(100/(1+(IC50/conc)^Slope)). A selection of the foregoing exemplified compounds was tested under these conditions: Several compounds are potent inhibitors (IC50<5 μM) or even very potent inhibitors (IC50<2 μM).

The invention claimed is:

1. A compound of general formula (I), wherein n represents 0, 1 or 2;

m represents 0 or 1 with the proviso that n≥m;

X is selected from the group consisting of O, S, NH and N—$C_{1-6}$-alkyl;

$R^1$, $R^2$ and $R^3$, are each independently of one another selected from the group consisting of H; F; Cl; Br; I; $NO_2$; CN; $C_{1-6}$-alkyl; $CF_3$; $CF_2H$; $CFH_2$; $CF_2Cl$; $CFCl_2$; C(=O)—H; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—$NH_2$; O—S(=O)$_2$—N(H)($C_{1-6}$-alkyl); O—S(=O)$_2$—N($C_{1-6}$-alkyl)$_2$; $NH_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—$NH_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—$NH_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—$NH_2$; N(H)—S(=O)$_2$—N(H)($C_{1-6}$-alkyl); N(H)—S(=O)$_2$N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—$NH_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$; $C_{3-10}$-cycloalkyl; 3 to 7 membered heterocyclyl; O—$C_{3-10}$-cycloalkyl and O-(3 to 7 membered heterocyclyl);

$R^4$ represents $CH_2F$; $CHF_2$, or $CF_3$;

$R^5$ represents H, $C_{1-6}$-alkyl, branched or unbranched, unsubstituted or mono- or poly-substituted, a $C_{3-10}$-cycloalkyl or a 3 to 7 membered heterocyclyl, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl);

Het represents 5-, 6-, 8-, 9- or 10-membered heteroaryl, each substituted by zero or one or two or three substituents of the group consisting of $R^6$, $R^7$ and $R^8$, wherein $R^6$, $R^7$ and $R^8$, are each independently of one another selected from the group consisting of F; Cl; Br; I; $NO_2$; CN; $C_{1-6}$-alkyl; $CF_3$; $CF_2H$; $CFH_2$; $CF_2Cl$; $CFCl_2$; C(=O)—H; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—$NH_2$; O—S(=O)$_2$—N(H)($C_{1-6}$-alkyl); O—S(=O)$_2$—N($C_{1-6}$-alkyl)$_2$; $NH_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—$NH_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—$NH_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—$NH_2$; N(H)—S(=O)$_2$—N(H)($C_{1-6}$-alkyl); N(H)—S(=O)$_2$N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—$NH_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); or S(=O)$_2$—N($C_{1-6}$-alkyl)$_2$; $C_{3-10}$-cycloalkyl; 3 to 7 membered heterocyclyl; O—$C_{3-10}$-cycloalkyl or O-(3 to 7 membered heterocyclyl);

$R^9$ represents H, $C_{1-10}$-alkyl, branched or unbranched, unsubstituted or mono- or poly-substituted; $C_{3-10}$-cycloalkyl or 3 to 10 membered heterocyclyl, wherein said $C_{3-10}$-cycloalkyl or 3 to 10 membered heterocyclyl in each case may be unsubstituted or mono- or poly-substituted and wherein said $C_{3-10}$-cycloalkyl or 3 to 10 membered heterocyclyl may be in each case connected via a $C_{1-8}$-alkylene group, which in turn may be branched or unbranched and may be unsubstituted or mono- or polysubstituted;

$R^{10}$ represents H, $C_{1-10}$-alkyl; $C_{3-10}$-cycloalkyl, 3 to 10 membered heterocyclyl or heteroaryl, wherein said $C_{3-10}$-cycloalkyl, 3 to 10 membered heterocyclyl or heteroaryl in each case may be unsubstituted or mono- or poly-substituted and wherein said $C_{3-10}$-cycloalkyl, 3 to 10 membered heterocyclyl or heteroaryl may be in each case connected via a $C_{1-8}$-alkylene group, which in turn may be branched or unbranched and may be unsubstituted or mono- or polysubstituted;

or

R⁹ and R¹⁰ together with the nitrogen atom connecting them form a 3 to 10 membered heterocyclyl;

wherein in each case said $C_{1-6}$-alkyl and $C_{1-10}$-alkyl may be branched or unbranched; unsubstituted or mono- or polysubstituted; and wherein in each case said $C_{3-10}$-cycloalkyl, 3 to 7 membered heterocyclyl, 3 to 10 membered heterocyclyl or heteroaryl may be unsubstituted or mono- or polysubstituted;

in form of the free compound and/or a physiologically acceptable salt and/or a physiologically acceptable solvate thereof.

2. A compound according to claim 1, wherein n represents 1 and m represents 0; and R¹, R² and R³, are each independently of one another selected from the group consisting of H; F; Cl; CN; $C_{1-6}$-alkyl; $CF_3$; $CF_2H$; $CFH_2$; OH; $OCF_3$; $OCF_2H$; $OCFH_2$; O—$C_{1-6}$-alkyl; O—C(=O)—$C_{1-6}$-alkyl; $NH_2$; N(H)($C_{1-6}$-alkyl); N($C_{1-6}$-alkyl)₂; $SCF_3$; S(=O)—$C_{1-6}$-alkyl; S(=O)₂—$C_{1-6}$-alkyl; S(=O)₂—OH; S(=O)₂—O—$C_{1-6}$-alkyl; S(=O)₂—$NH_2$; S(=O)₂—N(H)($C_{1-6}$-alkyl); or S(=O)₂—N($C_{1-6}$-alkyl)₂, wherein in each case $C_{1-6}$-alkyl may be branched or unbranched.

3. A compound according to claim 1, wherein R⁴ represents $CHF_2$ or $CF_3$.

4. A compound according to claim 1, wherein R⁵ is selected from the group consisting of H, methyl, ethyl, n-propyl, iso-propyl, n-butyl, sec-butyl, iso-butyl, tert-butyl, cyclopropyl, methoxy, ethoxy, methylsulfonyl, 2-oxetyl, 3-oxetyl, 2-tetrahydrofuranyl and 3-tetrahydrofuranyl.

5. A compound according to claim 1, wherein the compound of general formula (I) is a compound according to general formula (Ia) or (Ib),

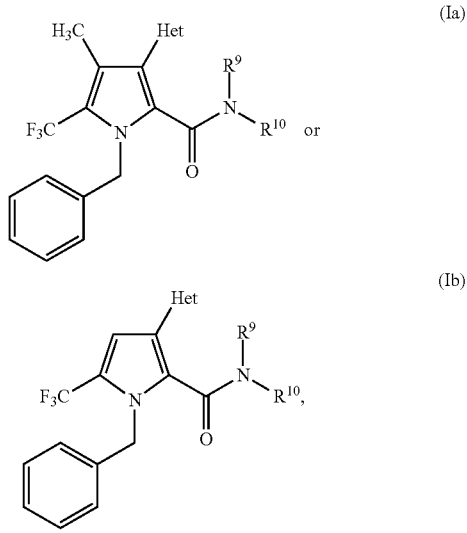

wherein Het, R⁹ and R¹⁰ are defined according to claim 1.

6. A compound according to claim 1, wherein

Het is selected from pyrrol, furanyl, thienyl, pyrazolyl, imidazolyl, isoxazolyl, isothiazolyl, oxazolyl, thiazolyl, triazolyl, oxadiazolyl, thiadiazolyl, tetrazolyl, indolyl, benzofuranyl, benzothienyl, indazolyl, benzimidazolyl, benzoxazolyl, benzothiazolyl, benzotriazolyl, pyridinyl, pyrazinyl, pyrimidinyl, pyridazinyl, triazinyl, quinolinyl, isoquinolinyl, quinoxalinyl, quinazolinyl, cinnolinyl, 1,5-naphthyridinyl, 1,6-naphthyridinyl, 1,7-naphthyridinyl, 1,8-naphthyridinyl, 2,3-naphthyridinyl, 2,6-naphthyridinyl and 2,7-naphthyridinyl.

7. A compound according to claim 1, wherein

R⁶, R⁷ and R⁸ are each independently of one another selected from the group consisting of F; Cl; CN; $C_{1-6}$-alkyl; $CF_3$; $CF_2H$; $CFH_2$; OH; $OCF_3$; $OCF_2H$; $OCFH_2$; O—$C_{1-6}$-alkyl; O—C(=O)—$C_{1-6}$-alkyl; $NH_2$; N(H)($C_{1-6}$-alkyl); N($C_{1-6}$-alkyl)₂; $SCF_3$; S(=O)—$C_{1-6}$-alkyl; S(=O)₂—$C_{1-6}$-alkyl; S(=O)₂—OH; S(=O)₂—O—$C_{1-6}$-alkyl; S(=O)₂—$NH_2$; S(=O)₂—N(H)($C_{1-6}$-alkyl); S(=O)₂—N($C_{1-6}$-alkyl)₂; $C_{3-6}$-cycloalkyl and O—$C_{3-6}$-cycloalkyl;

wherein in each case said $C_{1-6}$-alkyl may be branched or unbranched and wherein in each case said $C_{3-6}$-cycloalkyl may be unsubstituted or mono- or polysubstituted.

8. A compound according to claim 1, wherein

R⁹ represents

H or $C_{1-6}$-alkyl, branched or unbranched, unsubstituted or substituted with 1, 2, 3, 4 or 5 substituents independently from one another selected from the group consisting of OH, =O, O—$C_{1-6}$-alkyl, S(=O)—$C_{1-6}$-alkyl, S(=O)₂—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)₂—$C_{1-6}$-alkyl, N($C_{1-6}$-alkyl)-S(=O)₂—$C_{1-6}$-alkyl, C(=O)—$NH_2$, C(=O)—N(H)($C_{1-6}$-alkyl), C(=O)—N($C_{1-6}$-alkyl)₂, C(=O)—O—$C_{1-6}$-alkyl; N(H)—C(=O)—$C_{1-6}$-alkyl, and N($C_{1-6}$-alkyl)-C(=O)—$C_{1-6}$-alkyl;

and

R¹⁰ represents

H; or $C_{1-6}$-alkyl, branched or unbranched, unsubstituted or substituted with 1, 2, 3, 4 or 5 substituents independently from one another selected from the group consisting of F, Cl, $CF_3$, CN, OH, =O, $OCF_3$, O—$C_{1-6}$-alkyl, O—(C=O)$C_{1-6}$-alkyl, S(=O)—$C_{1-6}$-alkyl, S(=O)₂—$C_{1-6}$-alkyl, S(=O)₂—$NH_2$, S(=O)₂—N(H)$C_{1-6}$-alkyl, S(=O)₂—N($C_{1-6}$-alkyl)₂, $NH_2$, NH($C_{1-6}$-alkyl), N($C_{1-6}$-alkyl)₂, N(H)—S(=O)—$C_{1-6}$-alkyl, N($C_{1-6}$-alkyl)-S(=O)—$C_{1-6}$-alkyl, N(H)—S(=O)₂—$C_{1-6}$-alkyl, N($C_{1-6}$-alkyl)-S(=O)₂—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)₂, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)₂, C(=O)—$NH_2$, C(=O)—N(H)($C_{1-6}$-alkyl), C(=O)—N($C_{1-6}$-alkyl)₂, C(=O)—O—$C_{1-6}$-alkyl; N(H)—C(=O)—$C_{1-6}$-alkyl, and N($C_{1-6}$-alkyl)-C(=O)—$C_{1-6}$-alkyl; or $C_{3-6}$-cycloalkyl, unsubstituted or substituted with 1, 2, 3, 4 or 5 substituents independently from one another selected from the group consisting of F, Cl, CN, $CF_3$, =O, $OCF_3$, $C_{1-6}$-alkylen-OH, $C_{1-6}$-alkyl, OH, O—$C_{1-6}$-alkyl, O—(C=O)$C_{1-6}$-alkyl, S(=O)—$C_{1-6}$-alkyl, S(=O)₂—$C_{1-6}$-alkyl, S(=O)₂—$NH_2$, S(=O)₂—N(H)$C_{1-6}$-alkyl, S(=O)₂—N($C_{1-6}$-alkyl)₂, $NH_2$, NH($C_{1-6}$-alkyl), N($C_{1-6}$-alkyl)₂, N(H)—S(=O)—$C_{1-6}$-alkyl, N($C_{1-6}$-alkyl)-S(=O)—$C_{1-6}$-alkyl, N(H)—S(=O)₂—$C_{1-6}$-alkyl, N($C_{1-6}$-alkyl)-S(=O)₂—$C_{1-6}$-alkyl, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)₂, N(H)—C(=O)—

NH$_2$, N(H)—C(=O)—N(H)(C$_{1-6}$-alkyl), N(H)—C(=O)—N(C$_{1-6}$-alkyl)$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl, and N(C$_{1-6}$-alkyl)-C(=O)—C$_{1-6}$-alkyl; wherein said C$_{3-6}$-cycloalkyl is optionally connected via C$_{1-6}$-alkylene, branched or unbranched, which in turn may be unsubstituted or substituted with 1, 2, 3, 4 or 5 substituents independently from one another selected from the group consisting of F, Cl, CF$_3$, =O, OCF$_3$, OH, O—C$_{1-6}$-alkyl and C$_{1-6}$-alkylen-OH; or 3-7-membered heterocyclyl, which is unsubstituted or substituted with 1, 2, 3, 4 or 5 substituents independently from one another selected from the group consisting of F, Cl, CN, CF$_3$, =O, OCF$_3$, C$_{1-6}$-alkylen-OH, C$_{1-6}$ alkyl, OH, O—C$_{1-6}$-alkyl, O—(C=O)C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, N(H)—C(=O)—O—C$_{1-6}$-alkyl; O—C(=O)—NH$_2$, O—C(=O)—N(H)(C$_{1-6}$-alkyl), O—C(=O)—N(C$_{1-6}$-alkyl)$_2$, N(H)—C(=O)—NH$_2$, N(H)—C(=O)—N(H)(C$_{1-6}$-alkyl), N(H)—C(=O)—N(C$_{1-6}$-alkyl)$_2$, (C=O)C$_{1-6}$-alkyl, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl, and N(C$_{1-6}$-alkyl)-C(=O)—C$_{1-6}$-alkyl, wherein said 3-7-membered heterocyclyl is optionally connected via C$_{1-6}$-alkylene, branched or unbranched, which in turn may be unsubstituted or substituted with 1, 2, 3, 4 or 5 substituents independently from one another selected from the group consisting of F, Cl, CF$_3$, =O, OCF$_3$, OH, O—C$_{1-6}$-alkyl and C$_{1-6}$-alkylen-OH;

or heteroaryl, which is unsubstituted or substituted with 1, 2, 3, 4 or 5 substituents independently from one another selected from the group consisting of F, Cl, CN, CF$_3$, OCF$_3$, C$_{1-6}$-alkylen-OH, C$_{1-6}$-alkyl, OH, O—C$_{1-6}$-alkyl, O—(C=O)C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, N(H)—C(=O)—O—C$_{1-6}$-alkyl; O—C(=O)—NH$_2$, O—C(=O)—N(H)(C$_{1-6}$-alkyl), O—C(=O)—N(C$_{1-6}$-alkyl)$_2$, N(H)—C(=O)—NH$_2$, N(H)—C(=O)—N(H)(C$_{1-6}$-alkyl), N(H)—C(=O)—N(C$_{1-6}$-alkyl)$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl, and N(C$_{1-6}$-alkyl)-C(=O)—C$_{1-6}$-alkyl, wherein said heteroaryl is optionally connected via C$_{1-6}$-alkylene, branched or unbranched, which in turn may be unsubstituted or substituted with 1, 2, 3, 4 or 5 substituents independently from one another selected from the group consisting of F, Cl, CF$_3$, =O, OCF$_3$, OH, O—C$_{1-6}$-alkyl and C$_{1-6}$-alkylen-OH.

9. A compound according to claim 1, wherein R$^9$ and R$^{10}$ together with the nitrogen atom connecting them form a 3 to 7-membered heterocyclyl, unsubstituted or substituted with 1, 2, 3, 4 or 5 substituents selected from the group consisting of F, Cl, CN, CF$_3$, =O, OH, O—C$_{1-6}$-alkyl, O—C$_{1-6}$-alkyl, C$_{1-6}$-alkylen-OH, OCF$_3$, SO$_2$(C$_{1-6}$-alkyl), SO$_2$NH$_2$, SO$_2$N(H)C$_{1-6}$-alkyl, SO$_2$N(C$_{1-6}$-alkyl)$_2$, C$_{1-6}$-alkylen-SO$_2$(C$_{1-6}$-alkyl), NH$_2$, NH(C$_{1-6}$-alkyl), N(C$_{1-6}$-alkyl)$_2$, (C=O)C$_{1-6}$-alkyl, C$_{3-6}$-cycloalkyl or 3 to 7 membered heterocyclyl, in each case unsubstituted or mono- or polysubstituted.

10. A compound according to claim 1, wherein
R$^9$ represents H or C$_{1-6}$-alkyl; and
R$^{10}$ represents C$_{3-6}$-cycloalkyl, which is unsubstituted or substituted with 1, 2, 3, 4 or 5 substituents independently from one another selected from the group consisting of F, Cl, CF$_3$, =O, OCF$_3$, OH, O—C$_{1-6}$-alkyl, C$_{1-6}$-alkylen-OH and C$_{1-6}$-alkyl; or 3-7-membered heterocyclyl, which contains 1 or 2 heteroatoms or heteroatom groups independently from one another selected from the group consisting of O, S, S(=O), S(=O)$_2$, NH and N—C$_{1-6}$-alkyl, and which is unsubstituted or substituted with 1, 2, 3, 4 or 5 substituents independently from one another selected from the group consisting of F, Cl, CF$_3$, OCF$_3$, CN, C$_{1-6}$-alkyl, C$_{1-6}$-alkylen-OH and O—C$_{1-6}$-alkyl; or heteroaryl, which contains at least one nitrogen atom and which is unsubstituted or substituted with 1, 2 or 3 substituents independently from one another selected from the group consisting of F, Cl, CN, CF$_3$, OCF$_3$, C$_{1-6}$-alkylen-OH, C$_{1-6}$-alkyl, OH, O—C$_{1-6}$-alkyl, S(=O)$_2$—C$_{1-6}$-alkyl, S(=O)$_2$—NH$_2$, NH$_2$, NH(C$_{1-6}$-alkyl), N(C$_{1-6}$-alkyl)$_2$, O—C(=O)—NH$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl;

or a part structure of general formula SF-III

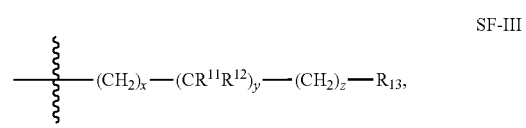

wherein
x represents 0, 1 or 2;
y represents 0, 1 or 2;
z represents 0, 1 or 2;
on the condition that the sum of x, y and z is 1, 2, 3, 4, 5 or 6;
R$^{11}$ and R$^{12}$ are independently from one another selected from H or C$_{1-6}$-alkyl; or
R$^{11}$ and R$^{12}$ together with the carbon atom connecting them form a C$_{3-6}$-cycloalkyl or a 3-7-membered heterocyclyl, which contains 1 or 2 heteroatoms or heteroatom groups independently from one another selected from the group consisting of O, S, S(=O), S(=O)$_2$, NH and N—C$_{1-6}$-alkyl, wherein said C$_{3-6}$-cycloalkyl or 3-7-membered heterocyclyl may be unsubstituted or substituted with 1, 2, 3, 4 or 5 substituents independently from one another selected from the group consisting of F, Cl, CF$_3$, OCF$_3$, CN, C$_{1-6}$-alkyl and O—C$_{1-6}$-alkyl;
R$^{13}$ is selected from the group consisting of
H, F, Cl, CN, CF$_3$, OCF$_3$, C$_{1-8}$-alkylen-OH, OH, O—C$_{1-6}$-alkyl, O—(C=O)C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—C(=O)—C$_{1-6}$-alkyl, N(C$_{1-6}$-alkyl)-C(=O)—C$_{1-6}$-alkyl, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl, N(H)—C(=O)—NH$_2$, N(H)—C (=O)—N(H)(C$_{1-6}$-alkyl), N(H)—C(=O)—N(C$_{1-6}$-alkyl)$_2$, N(H)—C(=O)—O—C$_{1-6}$-alkyl; O—C(=O)—NH$_2$, O—C(=O)—N(H)(C$_{1-6}$-alkyl), O—C(=O)—N(C$_{1-6}$-alkyl)$_2$; or represents C$_{3-6}$-cycloalkyl, which is unsubstituted or substituted with 1, 2, 3, 4, or 5 substituents independently from one another selected from the group consisting of F, Cl, CF$_3$, =O, OCF$_3$, OH, O—C$_{1-6}$-alkyl, C$_{1-6}$-alkylen-OH and C$_{1-6}$-alkyl; or 3-7-membered heterocyclyl, which contains 1 or 2 heteroatoms or heteroatom groups independently from one another selected from the group consisting of O, S, S(=O), S(=O)$_2$, NH and N—C$_{1-6}$-alkyl, and which is unsubstituted or substituted with 1, 2, 3, 4 or 5 substituents independently from one another selected from the group consisting of F, Cl, CF$_3$, OCF$_3$, CN, C$_{1-6}$-alkyl and O—C$_{1-6}$-alkyl; or heteroaryl, which contains at least one nitrogen atom and which is unsubstituted or substituted with 1, 2 or 3 substituents independently from one another selected from the group consisting of F, Cl, CN, CF$_3$, OCF$_3$, C$_{1-6}$-alkylen-OH, C$_{1-6}$-alkyl, OH, O—C$_{1-6}$-alkyl, S(=O)$_2$—C$_{1-6}$-alkyl, S(=O)$_2$—NH$_2$, NH$_2$, NH(C$_{1-6}$-alkyl), N(C$_{1-6}$-alkyl)$_2$, O—C(=O)—NH$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl;

or

R$^9$ and R$^{10}$ together with the nitrogen atom connecting them form a heterocyclyl, selected from the group consisting of

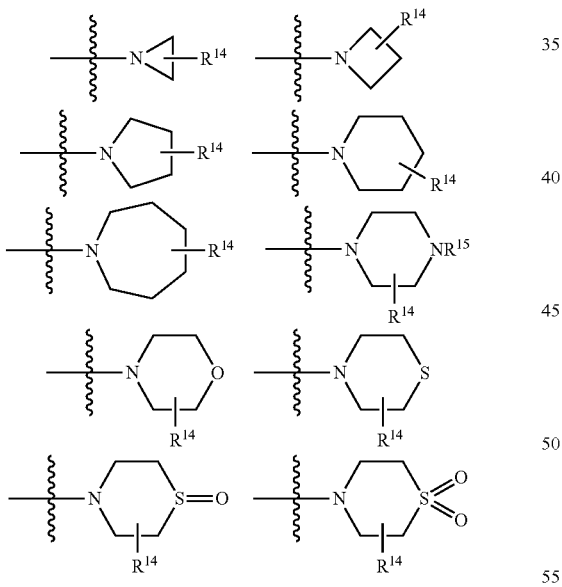

wherein

R$^{14}$ denotes 0, 1, 2, 3 or 4 substituents which are in each case independently of each other selected from the group consisting of F, Cl, CF$_3$, =O, OCF$_3$, OH, O—C$_{1-6}$-alkyl, C$_{1-6}$-alkylen-OH, C$_{1-6}$-alkylen-SO$_2$(C$_{1-6}$-alkyl), SO$_2$(C$_{1-6}$-alkyl) and C$_{1-6}$-alkyl;

or

R$^{14}$ denotes at least two substituents, wherein two substituents R$^{14}$ stand together for a C$_{1-6}$-alkylen-group, substituted or unsubstituted, wherein optionally one or more C-atoms of the C$_{1-6}$-alkylen-group is replaced by a heteroatom or heteroatom group, selected of O, N—R$^{15}$, S, S(O) and S(O)$_2$, and wherein these two substituents R$^{14}$ are positioned at different carbon atoms of the heterocyclyl, so the C$_{1-6}$-alkylen-group represents a bridge to form a bicyclic heterocyclyl;

or

R$^{14}$ denotes at least two substituents, wherein two substituents R$^{14}$ stand together for a C$_{2-6}$-alkylen-group, substituted or unsubstituted, wherein optionally one or more C-atoms of the C$_{2-6}$-alkylen-group is replaced by a heteroatom or heteroatom group, selected of O, N—R$^{15}$, S, S(O) and S(O)$_2$, and wherein these two substituents R$^{14}$ are positioned at the same carbon atom of the heterocyclyl, so the C$_{2-6}$-alkylen-group forms a spiro-heterocyclyl; and R$^{15}$ represents H, C$_{1-6}$-alkyl or (C=O)C$_{1-6}$-alkyl.

11. A compound according to claim 1, wherein the compound of general formula (I) is a compound according to general formula (Ia) or (Ib),

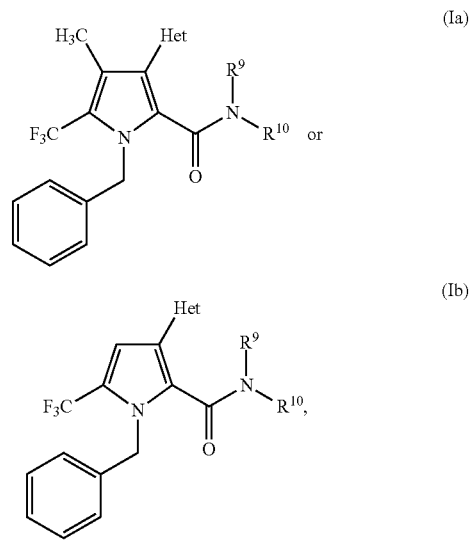

wherein

Het is select from group consisting of pyrrol, thienyl, pyrazolyl, imidazolyl, isoxazolyl, oxazolyl, thiazolyl, pyridinyl, pyrazinyl, pyrimidinyl and pyridazinyl, each substituted by zero or one or two substituents of the group consisting of R$^6$ and R$^7$, wherein R$^6$ and R$^7$ are each independently of one another selected from the group consisting of F; Cl; CN; C$_{1-6}$-alkyl; CF$_3$; CF$_2$H; CFH$_2$; OH; OCF$_3$; OCF$_2$H; OCFH$_2$; O—C$_{1-6}$-alkyl; S(=O)—C$_{1-6}$-alkyl; S(=O)$_2$—C$_{1-6}$-alkyl; cyclopropyl or O-cyclopropyl;

R$^9$ represents H or C$_{1-6}$-alkyl; and

R$^{10}$ represents

C$_{3-6}$-cycloalkyl, which is unsubstituted or substituted with 1, 2 or 3 substituents independently from one another selected from the group consisting of F, Cl, CF$_3$, =O, OCF$_3$, OH, O—C$_{1-6}$-alkyl, C$_{1-6}$-alkylen-OH and C$_{1-6}$-alkyl;

or
represents a part structure of general formula SF-III

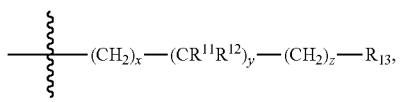

wherein
x represents 0, 1 or 2;
y represents 0, 1 or 2;
z represents 0, 1 or 2;
on the condition that the sum of x, y and z is 1, 2, 3, 4, 5 or 6;
$R^{11}$ and $R^{12}$ are independently from one another selected from H or $C_{1-6}$-alkyl;
$R^{13}$ is selected from the group consisting of
H, F, Cl, CN, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—C(=O)—$C_{1-6}$-alkyl, N($C_{1-6}$-alkyl)-C(=O)—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—NH$_2$, C(=O)—N(H)($C_{1-6}$-alkyl), C(=O)—N($C_{1-6}$-alkyl)$_2$, C(=O)—O—$C_{1-6}$-alkyl, N(H)—C(=O)—NH$_2$, N(H)—C(=O)—N(H)($C_{1-6}$-alkyl), N(H)—C(=O)—N($C_{1-6}$-alkyl)$_2$;
or
$R^9$ and $R^{10}$ together with the nitrogen atom connecting them form a heterocyclyl, selected from the group consisting of

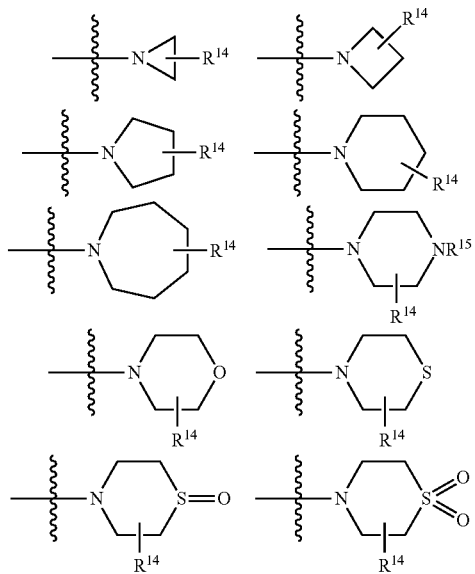

wherein
$R^{14}$ denotes 0, 1 or 2 substituents which are in each case independently of each other selected from the group consisting of F, Cl, CF$_3$, =O, OCF$_3$, OH, O—$C_{1-6}$-alkyl, $C_{1-6}$-alkylen-OH, $C_{1-6}$-alkylen-SO$_2$($C_{1-6}$-alkyl), SO$_2$($C_{1-6}$-alkyl) and $C_{1-6}$-alkyl;
and
$R^{15}$ represents H, $C_{1-6}$-alkyl or (C=O)$C_{1-6}$-alkyl.

12. The compound according to claim 1, which is selected from the group consisting of
01 1-Benzyl-N-(2,2-dimethyl-propyl)-3-[3-fluoro-5-(trifluoromethyl)-pyridin-2-yl]-N,4-dimethyl-5-(trifluoromethyl)-1H-pyrrole-2-carboxylic acid amide;
02 [1-Benzyl-3-[3-fluoro-5-(trifluoromethyl)-pyridin-2-yl]-4-methyl-5-(trifluoromethyl)-1H-pyrrol-2-yl]-morpholin-4-yl-methanone;
03 1-Benzyl-3-(3,5-dimethyl-isoxazol-4-yl)-N-(2,2-dimethyl-propyl)-N,4-dimethyl-5-(trifluoromethyl)-1H-pyrrole-2-carboxylic acid amide;
04 [1-Benzyl-3-(3,5-dimethyl-isoxazol-4-yl)-4-methyl-5-(trifluoromethyl)-1H-pyrrol-2-yl]-morpholin-4-yl-methanone;
05 1-Benzyl-3-(6-cyano-4-methyl-pyridin-3-yl)-N-(2,2-dimethyl-propyl)-N,4-dimethyl-5-(trifluoromethyl)-1H-pyrrole-2-carboxylic acid amide;
06 5-[1-Benzyl-4-methyl-2-(morpholine-4-carbonyl)-5-(trifluoromethyl)-1H-pyrrol-3-yl]-4-methyl-pyridine-2-carbonitrile;
07 1-Benzyl-3-(6-chloro-4-methyl-pyridin-3-yl)-N-(2,2-dimethyl-propyl)-N,4-dimethyl-5-(trifluoromethyl)-1H-pyrrole-2-carboxylic acid amide;
08 [1-Benzyl-3-(6-chloro-4-methyl-pyridin-3-yl)-4-methyl-5-(trifluoromethyl)-1H-pyrrol-2-yl]-morpholin-4-yl-methanone;
09 1-Benzyl-N-(2,2-dimethyl-propyl)-3-(6-methoxy-4-methyl-pyridin-3-yl)-N,4-dimethyl-5-(trifluoromethyl)-1H-pyrrole-2-carboxylic acid amide;
10 [1-Benzyl-3-(6-methoxy-4-methyl-pyridin-3-yl)-4-methyl-5-(trifluoromethyl)-1H-pyrrol-2-yl]-morpholin-4-yl-methanone;
11 1-Benzyl-N-(2,2-dimethyl-propyl)-N,4-dimethyl-3-pyrazin-2-yl-5-(trifluoromethyl)-1H-pyrrole-2-carboxylic acid amide;
12 [1-Benzyl-4-methyl-3-pyrazin-2-yl-5-(trifluoromethyl)-1H-pyrrol-2-yl]-morpholin-4-yl-methanone;
13 1-Benzyl-N-(2,2-dimethyl-propyl)-N,4-dimethyl-3-pyridazin-4-yl-5-(trifluoromethyl)-1H-pyrrole-2-carboxylic acid amide;
14 [1-Benzyl-4-methyl-3-pyridazin-4-yl-5-(trifluoromethyl)-1H-pyrrol-2-yl]-morpholin-4-yl-methanone;
15 1-Benzyl-N-(2,2-dimethyl-propyl)-3-(5-fluoro-pyridin-2-yl)-N,4-dimethyl-5-(trifluoromethyl)-1H-pyrrole-2-carboxylic acid amide;
16 [1-Benzyl-3-(5-fluoro-pyridin-2-yl)-4-methyl-5-(trifluoromethyl)-1H-pyrrol-2-yl]-morpholin-4-yl-methanone;
17 1-Benzyl-3-(5-chloro-pyrimidin-2-yl)-N-(2,2-dimethyl-propyl)-N,4-dimethyl-5-(trifluoromethyl)-1H-pyrrole-2-carboxylic acid amide;
18 [1-Benzyl-3-(5-chloro-pyrimidin-2-yl)-4-methyl-5-(trifluoromethyl)-1H-pyrrol-2-yl]-morpholin-4-yl-methanone;
19 1-Benzyl-N-(2,2-dimethyl-propyl)-3-(5-fluoro-pyrimidin-2-yl)-N,4-dimethyl-5-(trifluoromethyl)-1H-pyrrole-2-carboxylic acid amide;
20 [1-Benzyl-3-(5-fluoro-pyrimidin-2-yl)-4-methyl-5-(trifluoromethyl)-1H-pyrrol-2-yl]-morpholin-4-yl-methanone;
21 1-Benzyl-N-(2,2-dimethyl-propyl)-3-(5-methoxy-pyrimidin-2-yl)-N,4-dimethyl-5-(trifluoromethyl)-1H-pyrrole-2-carboxylic acid amide;
22 1-Benzyl-N-(2,2-dimethyl-propyl)-N,4-dimethyl-3-pyrimidin-2-yl-5-(trifluoromethyl)-1H-pyrrole-2-carboxylic acid amide;

23 [1-Benzyl-4-methyl-3-pyrimidin-2-yl-5-(trifluoromethyl)-1H-pyrrol-2-yl]-morpholin-4-yl-methanone;
24 1-Benzyl-3-(6-chloro-pyridazin-3-yl)-N-(2,2-dimethyl-propyl)-N,4-dimethyl-5-(trifluoromethyl)-1H-pyrrole-2-carboxylic acid amide;
25 [1-Benzyl-3-(6-chloro-pyridazin-3-yl)-4-methyl-5-(trifluoromethyl)-1H-pyrrol-2-yl]-morpholin-4-yl-methanone;
26 [1-Benzyl-4-methyl-3-(1H-pyrazol-4-yl)-5-(trifluoromethyl)-1H-pyrrol-2-yl]-morpholin-4-yl-methanone;
27 [1-Benzyl-4-methyl-3-(1-methyl-1H-pyrazol-4-yl)-5-(trifluoromethyl)-1H-pyrrol-2-yl]-morpholin-4-yl-methanone;
28 1-Benzyl-3-(5-chloro-pyridin-2-yl)-N-(2,2-dimethyl-propyl)-N,4-dimethyl-5-(trifluoromethyl)-1H-pyrrole-2-carboxylic acid amide;
29 1-Benzyl-3-(5-chloro-pyridin-2-yl)-N,4-dimethyl-N-(2-methylsulfonyl-ethyl)-5-(trifluoromethyl)-1H-pyrrole-2-carboxylic acid amide;
30 [1-Benzyl-3-(5-chloro-pyridin-2-yl)-4-methyl-5-(trifluoromethyl)-1H-pyrrol-2-yl]-morpholin-4-yl-methanone;
31 1-Benzyl-3-(5-chloro-pyrimidin-2-yl)-N-(2-cyano-2-methyl-propyl)-N,4-dimethyl-5-(trifluoromethyl)-1H-pyrrole-2-carboxylic acid amide;
32 1-Benzyl-N-(2-carbamoyl-2-methyl-propyl)-3-(5-chloro-pyrimidin-2-yl)-N,4-dimethyl-5-(trifluoromethyl)-1H-pyrrole-2-carboxylic acid amide;
33 4-[1-Benzyl-3-(5-chloro-pyrimidin-2-yl)-4-methyl-5-(trifluoromethyl)-1H-pyrrole-2-carbonyl]-piperazin-2-one;
34 [1-Benzyl-3-(5-chloro-pyrimidin-2-yl)-4-methyl-5-(trifluoromethyl)-1H-pyrrol-2-yl]-(2,2-dimethyl-morpholin-4-yl)-methanone;
35 [1-Benzyl-3-(5-chloro-pyrimidin-2-yl)-4-methyl-5-(trifluoromethyl)-1H-pyrrol-2-yl]-(1,1-dioxo-[1,4]thiazinan-4-yl)-methanone;
36 1-Benzyl-3-(5-chloro-pyrimidin-2-yl)-N-cyclopropyl-4-methyl-5-(trifluoromethyl)-1H-pyrrole-2-carboxylic acid amide;
37 1-Benzyl-N-(2,2-dimethyl-propyl)-3-(2-methoxy-pyrimidin-5-yl)-N,4-dimethyl-5-(trifluoromethyl)-1H-pyrrole-2-carboxylic acid amide;
38 [1-Benzyl-3-(2-methoxy-pyrimidin-5-yl)-4-methyl-5-(trifluoromethyl)-1H-pyrrol-2-yl]-morpholin-4-yl-methanone;
39 1-Benzyl-N-(2,2-dimethyl-propyl)-N,4-dimethyl-3-pyrimidin-5-yl-5-(trifluoromethyl)-1H-pyrrole-2-carboxylic acid amide;
40 [1-Benzyl-4-methyl-3-pyrimidin-5-yl-5-(trifluoromethyl)-1H-pyrrol-2-yl]-morpholin-4-yl-methanone;
41 1-Benzyl-3-(5-chloro-thiophen-2-yl)-N-(2,2-dimethyl-propyl)-N,4-dimethyl-5-(trifluoromethyl)-1H-pyrrole-2-carboxylic acid amide;
42 1-Benzyl-N-(2,2-dimethyl-propyl)-N,4-dimethyl-3-(1H-pyrazol-4-yl)-5-(trifluoromethyl)-1H-pyrrole-2-carboxylic acid amide;
43 1-Benzyl-N-(2,2-dimethyl-propyl)-3-(6-hydroxy-pyridin-3-yl)-N,4-dimethyl-5-(trifluoromethyl)-1H-pyrrole-2-carboxylic acid amide;
44 [1-Benzyl-3-(6-hydroxy-pyridin-3-yl)-4-methyl-5-(trifluoromethyl)-1H-pyrrol-2-yl]-morpholin-4-yl-methanone;
45 1-Benzyl-N-(2,2-dimethyl-propyl)-3-(6-methoxy-pyridin-3-yl)-N,4-dimethyl-5-(trifluoromethyl)-1H-pyrrole-2-carboxylic acid amide;
46 [1-Benzyl-3-(6-methoxy-pyridin-3-yl)-4-methyl-5-(trifluoromethyl)-1H-pyrrol-2-yl]-morpholin-4-yl-methanone;
47 1-Benzyl-N-(2,2-dimethyl-propyl)-3-(5-methoxy-pyrazin-2-yl)-N,4-dimethyl-5-(trifluoromethyl)-1H-pyrrole-2-carboxylic acid amide;
48 [1-Benzyl-3-(5-methoxy-pyrazin-2-yl)-4-methyl-5-(trifluoromethyl)-1H-pyrrol-2-yl]-morpholin-4-yl-methanone;
49 1-Benzyl-N-(2,2-dimethyl-propyl)-N,4-dimethyl-3-(1-methyl-1H-pyrazol-4-yl)-5-(trifluoromethyl)-1H-pyrrole-2-carboxylic acid amide;
50 1-Benzyl-3-(5-chloro-pyridin-2-yl)-N-isopropyl-N,4-dimethyl-5-(trifluoromethyl)-1H-pyrrole-2-carboxylic acid amide;
51 1-Benzyl-N-isopropyl-N,4-dimethyl-3-(1-methyl-1H-pyrazol-3-yl)-5-(trifluoromethyl)-1H-pyrrole-2-carboxylic acid amide;
52 1-Benzyl-3-(5-chloro-pyrimidin-2-yl)-N-isopropyl-4-methyl-5-(trifluoromethyl)-1H-pyrrole-2-carboxylic acid amide;
53 1-Benzyl-3-(5-chloro-pyrimidin-2-yl)-N-isopropyl-4-methyl-5-(trifluoromethyl)-1H-pyrrole-2-carboxylic acid amide;
54 1-Benzyl-3-(5-chloro-pyrimidin-2-yl)-N-isopropyl-N,4-dimethyl-5-(trifluoromethyl)-1H-pyrrole-2-carboxylic acid amide;
55 1-Benzyl-3-(5-cyclopropyl-pyrazin-2-yl)-N-isopropyl-N,4-dimethyl-5-(trifluoromethyl)-1H-pyrrole-2-carboxylic acid amide;
56 1-Benzyl-3-(5-cyclopropyl-pyrimidin-2-yl)-N-isopropyl-N,4-dimethyl-5-(trifluoromethyl)-1H-pyrrole-2-carboxylic acid amide;
57 1-Benzyl-3-(5-chloro-pyrimidin-2-yl)-N,4-dimethyl-N-[2-methyl-2-(methylcarbamoyl)-propyl]-5-(trifluoromethyl)-1H-pyrrole-2-carboxylic acid amide;
58 1-Benzyl-3-(5-chloro-pyrimidin-2-yl)-N-[2-(dimethyl-carbamoyl)-2-methyl-propyl]-N,4-dimethyl-5-(trifluoromethyl)-1H-pyrrole-2-carboxylic acid amide;
59 1-Benzyl-N-isopropyl-N,4-dimethyl-3-(1-methyl-1H-imidazol-2-yl)-5-(trifluoromethyl)-1H-pyrrole-2-carboxamide;
60 1-Benzyl-N-isopropyl-N,4-dimethyl-3-[5-(methylsulfinyl)-pyridin-2-yl]-5-(trifluoromethyl)-1H-pyrrole-2-carboxylic acid amide; and
61 1-Benzyl-3-[5-chloro-3-(methylsulfinyl)-pyridin-2-yl]-N-isopropyl-N,4-dimethyl-5-(trifluoromethyl)-1H-pyrrole-2-carboxylic acid amide;

in the form of the free compound and/or a physiologically acceptable salt or solvate thereof.

13. A pharmaceutical composition comprising at least one compound according to claim 1.

14. A method for the treatment of pain, said method comprising administering to a patient in need thereof an effective amount therefor of at least one compound according to claim 1.

15. The method according to claim 14, which is carried out for the treatment of pain, wherein the pain is one or more of acute pain and/or chronic pain and/or visceral pain and/or headache pain and/or inflammatory pain and/or mixed pain.

* * * * *